(12) United States Patent
Macoska

(10) Patent No.: US 7,598,028 B2
(45) Date of Patent: Oct. 6, 2009

(54) COMPOSITIONS AND METHODS FOR DETECTING AND TREATING PROSTATE DISORDERS

(75) Inventor: Jill A. Macoska, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 48 days.

(21) Appl. No.: 11/946,676

(22) Filed: Nov. 28, 2007

(65) Prior Publication Data

US 2008/0206766 A1  Aug. 28, 2008

Related U.S. Application Data

(60) Provisional application No. 60/861,346, filed on Nov. 28, 2006, provisional application No. 60/949,452, filed on Jul. 12, 2007.

(51) Int. Cl.
*C12Q 1/00* (2006.01)
*C12Q 33/567* (2006.01)
*G01N 33/563* (2006.01)

(52) U.S. Cl. .......................... 435/4; 435/7.1; 435/7.23; 436/513; 436/64

(58) Field of Classification Search ........................ None
See application file for complete search history.

(56) References Cited

OTHER PUBLICATIONS

Adamson Ed et al., "Egr1 transcription factor: muitiple roles in prostate tumor cell growth and survival." Tumour Biol. 2002 vol. 23:93-102.
Ao M et al., "Cross-talk between paracrine-acting cytokine and chemokine pathways promotes malignancy in benign human prostatic epithelium." Cancer Res. 2007 67(9) pp. 4244-53.
Arenas MI et al., "Morphometric evaluation of the human prostate." Int. J. Andrology 2001 vol. 24 pp. 37-47.
Begley L, "Concordant copy No. and transcriptional activity of genes mapping to derivative chromosomes 8 during cellular immortalization in vitro." Genes Chromosomes Cancer. 2006 45(2) pp. 136-146.
Begley L. et al., "CXCL12 overexpression and secretion by aging fibroblasts enhance human prostate epithelial proliferation in vitro." Aging Cell 2005 vol. 4(6):291-8.
Begley LA et al., "CXCL12 activates a robust transcriptional response in human prostate epithelial cells." J Biol Chem 2007 vol. 282(37):26767-74.
Berger AP et al., "Impact of age on complexed PSA levels in men with total PSA levels of up to 20 ng/mL." Urology 2003 vol. 62 pp. 840-4.
Berger AP et al.: "Large-scale study of clinical impact of PSA velocity: long-term PSA kinetics as method of differentiating men with from those without prostate cancer." Urology 2007 vol. 69 pp. 134-138.
Berges RR et al., "Implication of cell kinetic changes during the progression of human prostatic cancer." Clin. Cancer Res. 1995 vol. 1 pp. 473-480.
Burns JM et al., "A novel chemokine receptor for SDF-1 and I-TAC involved in cell survival, cell adhesion, and tumor development." J. Exp. Med. 2006 203(9):2201-13.
Cunha GR et al., "Smooth muscle-epithelial interactions in normal and neoplastic prostatic development" Acta Anat. 1996 vol. 155 pp. 63-72.
Darash-Yahana M. et al., "Role of high expression levels of CXCR4 in tumor growth, vascularization, and metastasis." FASEB J. 2004 vol. 18(11).
Gilbert SM et al., "Evidence suggesting PSA cutpoint of 2.5 ng/mL for prompting prostate biopsy: review of 36,316 biopsies" Urology 2005 vol. 65 pp. 549-553.
Hayward SW et al., "Interactions between adult human prostatic epithelium and rat urogenital sinus mesenchyme in a tissue recombination model". Differentiation 1998 vol. 63 pp. 131-140.
Inahara M. et al., "Improved prostate cancer detection using systematic 14-core biopsy for large prostate glands with normal digital rectal examination findings." Urology 2006 vol. 68 pp. 815-819.
Kravchick S. et al., "Predictive criteria for prostate cancer detection in men with serum PSA concentration of 2.0 to 4.0 ng/mL," Urology 2005 vol. 66 pp. 542-546.
Kukreja P. et al., "Up-regulation of CXCR4 expression in PC-3 cells by stromal-derived factor-1alpha (CXCL12) increases endothelial adhesion and transendothelial migration: role of MEK/ERK signaling pathway-dependent NF-kappaB activation." Cancer Res 2005 65(21) pp. 9891-9898.
Luciani LG et al., "Role of transperineal six-core prostate biopsy in patients with prostate-specific antigen level greater than 10 ng/mL and abnormal digital rectal examination findings" Urology 2006 vol. 67 pp. 555-558.
Macoska JA et al., Cancer Genet. Cytogenet. 2005 vol. 154 pp. 36-43.
Meigs JB et al, "Risk factors for clinical benign prostatic hyperplasia in a community-based population of healthy aging men" J. Clin. Epidemiol. vol. 54 pp. 935-944 (2001).
Mochizuki H. at al., "Interaction of ligand-receptor system between stromal-cell-derived factor-1 and CXC chemokine receptor 4 in human prostate cancer: a possible predictor of metastasis" Biochem Biophys Res Commun. 2004 vol. 320(3):656-63.
Neuhouser ML et al., "Steroid hormones and hormone-related genetic and lifestyle characteristics as risk factors for benign prostatic hyperplasia: review of epidemiologic literature" Urology 2004 vol. 64 pp. 201-211.
Olumi AF et al., "A novel coculture technique demonstrates that normal human prostatic fibroblasts contribute to tumor formation of LNCaP cells by retarding cell death" Cancer Res. 1998 vol. 58 pp. 4525-4530.

(Continued)

*Primary Examiner*—Larry R. Helms
*Assistant Examiner*—Lei Yao
(74) *Attorney, Agent, or Firm*—Casimir Jones SC

(57) ABSTRACT

The present invention relates to compositions and methods for the detecting, treating, and empirically investigating cellular proliferation disorders and cellular motility disorders. In particular, the present invention provides compositions and methods for using CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK ½, ELK-1) in the diagnosis, treatment, and empirical investigation of prostate disorders (e.g., prostate cancer, benign prostatic hypertrophy, prostatitis).

6 Claims, 39 Drawing Sheets

OTHER PUBLICATIONS

Pelzer AE et al., "Detection rates and biologic significance of prostate cancer with PSA less than 4.0 ng/mL: observation and clinical implications from Tyrol screening project" Urology 2005 vol. 66 pp: 1029-1033.

Pinsky PF et al., "Prostate volume and prostate-specific antigen levels in men enrolled in a large screening trial" Urology 2006 vol. 68 pp. 352-6v.

Wright EJ et al., J. Urol. 2002 vol. 167 pp. 2484-2487.

Simardi L.H et al., "Influence of asymptomatic histologic prostatitis on serum prostate-specific antigen: a prospective study" Urology 2004 vol. 64 pp. 1098-1101.

Singh S. et al., "CXCL12-CXCR4 interactions modulate prostate cancer cell migration, metalloproteinase expression and invasion" Lab Invest. 2004 vol. 84(12):1666-76.

Taichman RS et al., "Use of the stromal cell-derived factor-1/CXCR4 pathway in prostate cancer metastasis to bone" Cancer Res. 2002 62(6).

Thompson TC et al., "Multistage carcinogenesis induced by ras and myc oncogenes in a reconstituted organ" Cell 1989 vol. 56 pp. 917-930.

Wang J. et al., "Diverse signaling pathways through the SDF-1/CXCR4 chemokine axis in prostate cancer cell lines leads to altered patterns of cytokine secretion and angiogenesis" Cellular Signaling 17 2005 pp. 1578-1592.

COMPOSITIONS AND METHODS FOR DETECTING AND TREATING PROSTATE DISORDERS

The present application claims priority to U.S. Provisional Patent Application Ser. Nos. 60/861,346, filed Nov. 28, 2006, and 60/949,452, filed Jul. 12, 2007, each of which are herein incorporated by reference in their entireties.

This invention was made with government support under 1P50DK65313-03 awarded by the National Institute of Diabetes and Digestive And Kidney Diseases. The government has certain rights in the invention.

FIELD OF THE INVENTION

The present invention relates to compositions and methods for the detecting, treating, and empirically investigating cellular proliferation disorders and cellular motility disorders. In particular, the present invention provides compositions and methods for using CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK ½, ELK-1) in the diagnosis, treatment, and empirical investigation of prostate disorders (e.g., prostate cancer, benign prostatic hypertrophy, prostatitis).

BACKGROUND OF THE INVENTION

Prostate cancer is a disease in which cancer develops in the prostate, a gland in the male reproductive system. Cancer occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. It is least common in South and East Asia, more common in Europe—though the rates vary widely between countries—and most common in the United States. According to the American Cancer Society, prostate cancer is least common among Asian men and most common among black men with figures for European men in between. However, these high rates may be affected by increasing rates of detection.

Prostate cancer develops most frequently in men over fifty. This cancer can only occur in men; the prostate is exclusively of the male reproductive tract. It is the second most common type of cancer in men in the United States, where it is responsible for more male deaths than any other cancer except lung cancer. However, many men who develop prostate cancer never have symptoms, undergo no therapy, and eventually die of other causes. Many factors, including genetics and diet, have been implicated in the development of prostate cancer.

Prostate cancer is most often discovered by physical examination or by screening blood tests, such as the PSA (prostate specific antigen) test. There is some current concern about the accuracy of the PSA test and its usefulness. Suspected prostate cancer is typically confirmed by removing a piece of the prostate (biopsy) and examining it under a microscope. Further tests, such as X-rays and bone scans, may be performed to determine whether prostate cancer has spread.

Prostate cancer is currently treated with surgery, radiation therapy, hormone therapy, occasionally chemotherapy, or some combination of these. The age and underlying health of the man as well as the extent of spread, appearance under the microscope, and response of the cancer to initial treatment are important in determining the outcome of the disease. Since prostate cancer is commonly a disease of older men, many will die of other causes before the prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Prostate cancer is typically diagnosed with a digital rectal exam and/or prostate specific antigen (PSA) screening. An elevated PSA level can indicate the presence of PCA. PSA is used as a marker for prostate cancer because it is essentially restricted to prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, but PSA values within this range are just as likely the result of aging-associated increases in prostate volume due to benign prostatic hypertrophy (BPH) and/or prostate cancer. Serum PSA values above 10 are more reliably diagnostic of prostate cancer, and values above 50 may show that the tumor has spread elsewhere (e.g., metastasized) in the body.

The development of additional serum and tissue biomarkers specific to cancer (e.g., prostate) are needed to supplement currently available screening methods. In particular, additional serum and tissue biomarkers that might distinguish between benign prostatic hypertophy and prostate cancer among men with low ($\leq 10$ ng/ml) serum PSA would be useful for determining which patients are at higher risk for prostate cancer and require diagnostic needle biopsy from those patients at low risk who might benefit from a watchful waiting approach. In addition, new therapeutic treatments (e.g., targeted at newly identified biomarkers) are needed for the treatment of cancer (e.g., prostate cancer) and are of broad interest to the medical community, as well as to the pharmaceutical and biotech industries. The present invention addresses these issues.

SUMMARY OF THE INVENTION

The present invention relates to compositions and methods for the detecting, treating, and empirically investigating cellular proliferation disorders and cellular motility disorders. In particular, the present invention provides compositions and methods for using CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK ½, ELK-1) in the diagnosis, treatment, and empirical investigation of prostate disorders (e.g., prostate cancer, benign prostatic hypertrophy, prostatitis).

Experiments conducted during the development of embodiments for the present invention showed that CXCL1, CXCL5, CXCL6, and CXCL12 are expressed by aging human prostate stromal fibroblasts and promote epithelial and fibroblast cell proliferation. Experiments conducted during the development of embodiments for the present invention showed that CXCL12 and/or CXCL5 expression levels as low as the pM range for prostate epithelial cells stimulated cellular proliferation, and that higher CXCL12 and/or CXCL5 expression levels for such cells inhibited cellular proliferation. In addition, experiments conducted during the development of embodiments for the present invention showed that CXCL12 and/or CXCL5 expression levels in the nanomolar range induced prostate epithelial cell motility and invasiveness. Experiments conducted during development of embodiments for the present invention showed that a CXCL12-mediated proliferative response and/or a CXCL5-mediated proliferative response was ERK- and/or NF-kappaB-dependent. CXCL12 and/or CXCL5 was shown to initiate a complex, global transcriptional response in prostate epithelial cells that affected genes encoding proteins directly involved in the promotion of cellular proliferation and progression through the cell cycle, tumor metastasis, and cellular motility, or in the repression of genes encoding proteins involved in cell-cell adhesion resistance to apoptosis. Indeed, CXCL1, CXCL5, CXCL6, and CXCL12 were shown to influence expression of a proliferative and/or transformed cellular phenotype at many levels, and to perform, for example, a role in the etiology of benign and malignant prostatic diseases (e.g., prostate cancer, benign prostatic hypertrophy, prostatitis). Experiments conducted during the course of development of embodiments for the present invention showed that serum CXCL12 levels were significantly higher for patients exhibiting biopsy-verified cancer compared to men with who were biopsy-negative for cancer and histological prostatitis, and were significantly reduced or eliminated in the majority of men tested pre- and postprostatectomy. It was also shown that serum CXCL5 levels were progressively elevated in men with histological prostatitis and prostate cancer concurrent with BPH. Thus, it was shown that serum levels of CXCL5 and CXCL12 differentially distinguished between BPH, histological prostatitis, and prostate cancer.

Accordingly, in certain embodiments, the present invention provides methods for characterizing prostate tissue in a subject, comprising providing a prostate tissue sample from a subject suspected of having a prostatic disease, wherein the subject has a PSA level at or less than 10 ng/ml; and detecting the amount of expression of CXCL5 and CXCL12 in the prostate tissue sample, thereby characterizing the prostate tissue sample. The methods are not limited to a particular manner of detecting the amount of expression of CXCL5 and CXCL12. In some embodiments, detecting the amount of expression of CXCL5 and CXCL12 comprises detecting the amount of CXCL5 and CXCL12 mRNA and/or polypeptide. In some embodiments, detecting the amount of expression of a CXCL5 and CXCL12 polypeptide comprises exposing the CXCL5 and CXCL12 polypeptide to an antibody specific to the CXCL5 and CXCL12 polypeptide and detecting the amount of binding of the antibody to the CXCL5 and CXCL12 polypeptide. The methods are not limited to particular types of subjects (e.g., a human subject, a non-human subject). The methods are not limited to a particular type of prostatic disorder. In some embodiments, the prostatic disorder is prostate cancer and/or benign prostatic hypertrophy. The methods are not limited to a particular manner of characterizing the prostate tissue. In some embodiments, a higher amount of detected CXCL12 expression than CXCL5 expression is indicative of prostate cancer. In some embodiments, characterizing the prostate tissue comprises identifying a stage of prostate cancer in the prostate tissue. In some embodiments, a higher amount of detected CXCL5 expression than CXCL12 expression is indicative of benign prostatic hypertrophy. In some embodiments, the sample comprises tumor tissue. In some embodiments, the sample comprises a blood or blood component. In some embodiments, the method further includes providing a prognosis to the subject.

In certain embodiments, the present invention provides methods for treating a subject suffering from a prostate disorder, comprising administering to the subject a composition configured to reduce CXCL1, CXCL5, CXCL6, and/or CXCL12 activity within the subject. The composition is not limited to a particular manner of reducing CXCL1, CXCL5, CXCL6, and/or CXCL12 activity within the subject. In some embodiments, the composition reduces CXCL1, CXCL5, CXCL6, and/or CXCL12 activity through inhibition of at least one of the following components within the subject: CXCL1 protein, CXCL1 mRNA, CXCL1 nucleic acid, CXCL5 protein, CXCL5 mRNA, CXCL5 nucleic acid, CXCL6 protein, CXCL6 mRNA, CXCL6 nucleic acid, CXCL12 protein, CXCL12 mRNA, CXCL12 nucleic acid, CXCR1 protein, CXCR1 mRNA, CXCR1 nucleic acid, CXCR2 protein, CXCR2 mRNA, CXCR2 nucleic acid, CXCR4 protein, CXCR4 mRNA, CXCR4 nucleic acid, CXCR7 protein, CXCR7 mRNA, and CXCR7 nucleic acid. The composition is not limited to a particular manner of inhibiting such compounds. In some embodiments, the composition comprises antibodies specific for CXCL1, CXCL5, CXCL6, CXCL12, CXCR1, CXCR2, CXCR4, and CXCR7.

The method is not limited to treating a particular type of prostate disorder. In some embodiments, the prostate disorder is any type or kind or state of prostate cancer. In such embodiments, the amount of composition administered to the subject depends on what form of treatment is desired. For example, in some embodiments, the amount of the composition administered to the subject is sufficient to inhibit prostate epithelial cell proliferation. For example, in some embodiments, the amount of composition administered to the subject is sufficient to inhibit prostate epithelial cell metastasis. In some embodiments, the prostate disorder is prostate cancer, the method further comprises co-administering to the subject an anti-cancer agent. The method is not limited to a particular type or kind of anti-cancer agent, nor is it limited to the administration of a particular number of anti-cancer agents. In some embodiments, the-anti-cancer agent is select from at least one of the group consisting of Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl)retinamide; 13-cis retinoic acid; 3-Methyl TTNEB; 9-cis retinoic acid; fludarabine (2-F-ara-AMP); 2-chlorodeoxyadenosine (2-Cda), Antiproliferative agents, Piritrexim Isothionate, Antiprostatic hypertrophy agents, Sitogluside, Benign prostatic hypertrophy therapy agents, Tamsulosin Hydrochloride, Prostate growth inhibitor agents, Pentomone, and Radioactive agents, Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

In some embodiments, the prostate disorder is benign prostatic hypertrophy. In some embodiments, the method further comprises co-administration of an anti-benign prostatic hypertrophy agent. The method is not limited to a particular type or kind or number of anti-benign prostatic hypertrophy agents administered to the subject. In some embodiments, the anti-benign prostatic hypertrophy agent is selected from at least one of the group consisting of alpha-adrenergic blockers and 5-alpha-reductase inhibitors.

In some embodiments, the prostate disorder is prostatitis. In some embodiments, the method further comprises co-administration of an one or more anti-prostatitis agents. The method is not limited to a particular type or kind or number of anti-prostatitis agents administered to the subject. In some embodiments, the anti-prostatitis agent is selected from at least one of the group consisting of an antibiotic (e.g., Ofloxacin (Floxin), Ciprofloxacin (Cipro, Cipro XR), Levofloxacin (Levaquin), Gatifloxacin (Tequin), Ceftriaxone (Rocephin), Doxycycline (Bio-Tab, Doryx, Vibramycin)), Alpha-adrenergic agonists (e.g., Prazosin (Minipress)), benzodiazepines (e.g., Diazepam (Valium)).

In certain embodiments, the present invention provides methods for detecting prostate epithelial cell proliferation, comprising a) providing a sample comprising prostate epithelial cells; b) quantifying the amount of CXCL (e.g., CXCL1, CXCL5, CXCL6, and/or CXCL12) expression in the sample; and c) characterizing the quantified CXCL (e.g., CXCL1, CXCL5, CXCL6, and/or CXCL12) expression levels within a picomolar range as having prostate epithelial cell proliferation. In some embodiments, the CXCL is CXCL5 and/or CXCL12. In some embodiments, the sample is a prostate tumor sample and/or a prostate tissue sample. In some embodiments, the sample is selected from the group consisting of serum, plasma, blood, and urine.

In certain embodiments, the present invention provides methods for preventing the onset of a prostate disorder in a subject, comprising administering to the subject a composition configured to reduce CXCL1, CXCL5, CXCL6, and/or CXCL12 activity within the subject. In such embodiments, the composition reduces CXCL1, CXCL5, CXCL6, and/or CXCL12 activity through inhibition of at least one of the following targets within the subject: CXCL1 protein, CXCL1 mRNA, CXCL1 nucleic acid, CXCL5 protein, CXCL5 mRNA, CXCL5 nucleic acid, CXCL6 protein, CXCL6 mRNA, CXCL6 nucleic acid, CXCL12 protein, CXCL12 mRNA, CXCL12 nucleic acid, CXCR1 protein, CXCR1 mRNA, CXCR1 nucleic acid, CXCR2 protein, CXCR2 mRNA, CXCR2 nucleic acid, CXCR4 protein, CXCR4 mRNA, CXCR4 nucleic acid, CXCR7 protein, CXCR7 mRNA, and CXCR7 nucleic acid. In some embodiments, the composition comprises an antibody selected from the group consisting of CXCL1 antibody, CXCL5 antibody, CXCL6 antibody, CXCL12 antibody, CXCR1 antibody, CXCR2 antibody, CXCR4 antibody, and CXCR7 antibody. In some embodiments, the prostate disorder is selected from the group consisting of prostate cancer, prostatitis, and benign prostatic hypertrophy. In some embodiments, the amount of the composition administered to the subject is sufficient to inhibit prostate epithelial cell proliferation but not prostate epithelial cell metastasis. In some embodiments, the subject is at least sixty years old.

The present invention also provides a pharmaceutical composition comprising a pharmaceutically effective amount of an agent that inhibits CXCL1, CXCL5, CXCL6, and/or CXCL12 expression and/or activity, wherein the pharmaceutically effective amount is sufficient to inhibit prostate cancer growth and/or metastasis in a subject.

The present invention also provides a kit for characterizing prostate cancer in a subject, comprising: a reagent that specifically detects the presence or absence of expression of CXCL1, CXCL5, CXCL6, and/or CXCL12; and/or instructions for using the kit for characterizing prostate cancer in the subject. In some embodiments, the reagent comprises an antibody that specifically binds to CXCL1, CXCL5, CXCL6, and/or CXCL12 but does not specifically bind to the normal epithelium of prostate. In still further embodiments, the antibody specifically binds to CXCL1, CXCL5, CXCL6, and/or CXCL12 protein with low background binding. In yet other embodiments, the antibody binds to human and mouse CXCL1, CXCL5, CXCL6, and/or CXCL12. In some embodiments, the antibody is a monoclonal antibody. In some embodiments, the kit further comprises instructions. In some embodiments, the instructions comprise instructions required by the United States Food and Drug Administration for use in in vitro diagnostic products.

The present invention also provides a method of screening compounds, comprising providing a sample comprising prostate epithelial cells; and one or more test compounds; and contacting the prostate epithelial cell sample with the test compound; and detecting a change in CXCL1, CXCL5, CXCL6, and/or CXCL12 expression in the epithelial cell sample in the presence of the test compound relative to the absence of the test compound. In some embodiments, the epithelial cell sample is selected from the group consisting of high-grade prostatic intraepithelial neoplasia cells, benign prostatic hypertrophy cells, prostate carcinoma cells, and metastatic prostate carcinoma cells. In some embodiments, detecting comprises detecting CXCL1 mRNA, CXCL5 mRNA, CXCL6 mRNA, and/or CXCL12 mRNA. In other embodiments, detecting comprises detecting a CXCL1 polypeptide, a CXCL5 polypeptide, a CXCL6 polypeptide, and/or a CXCL12 polypeptide. In some embodiments, the cell is in vitro. In other embodiments, the cell is in vivo. In some embodiments, the test compound comprises an antisense compound. In other embodiments, the test compound comprises a drug. In some embodiments, the drug is an antibody. In other embodiments, the drug specifically binds to CXCL1, CXCL5, CXCL6, and/or CXCL12.

The present invention provides the use of a prostate disorder biomarker (e.g., CXCL1, CXCL5, CXCL6, CXCL12, CXCR1, CXCR2, CXCR4, CXCR7) as a marker to distinguish cancer cells and BPH cells from normal epithelial cells.

The present invention further provides use of a prostate disorder biomarker (e.g., CXCL1, CXCL5, CXCL6, CXCL12, CXCR1, CXCR2, CXCR4, CXCR7) as a marker to distinguish prostate cancer cells from normal prostate epithelium. The present invention additionally provides the use of an antibody that specifically binds to a prostate disorder biomarker (e.g., CXCL1, CXCL5, CXCL6, CXCL12, CXCR1, CXCR2, CXCR4, CXCR7) to distinguish cancer cells from normal epithelial cells.

In certain embodiments, the present invention provides methods for distinguishing (e.g., diagnosing, detecting) between BPH and PCa through measuring CXCL5 and CXCL12 serum levels in subjects presenting with low PSA.

In certain embodiments, the present invention provides methods for diagnosing BPH and PCa through measuring CXCL5 and CXCL12 serum levels in subjects presenting with low PSA, such that PCa is associated with higher CXCL12 serum levels than CXCL5 serum levels, and BPH is associated with higher CXCL5 serum levels than CXCL12 serum levels.

BRIEF DESCRIPTION OF THE DRAWINGS

FIG. 6A describes qRT-PCR data showing that older human prostate stromal fibroblasts (N=3) express 2-3× higher levels of CXCL1, CXCL5, CXCL6, and CXCL12 gene transcripts compared to younger fibroblasts (N=3). FIG. 6B describes ELISA data showing that older human prostate stromal fibroblasts (N=3) express 2-3× higher levels of CXCL1, CXCL5, CXCL6, and CXCL12 protein compared to younger fibroblasts (N=3). FIG. 6C describes how CXCL1, CXCL5, CXCL6, and CXCL12 stimulate N15C6 and LNCaP prostate epithelial cell proliferation and N1 prostate fibroblast cell proliferation compared to serum-free (SF HIE) media alone (* indicates growth significantly ($p<0.05$) higher than that achieved in SF HIE media). FIG. 6D describes how CXCL5 stimulates the phosphorylation and activation of ERK ½, p65 (the catalytic subunit of NfkappaB) and STAT3.

A. Benign glands demonstrating weak staining;
B. PCa (Gleason sum 3+3) demonstrating weak staining;
C. PCa (Gleason sum 4+4) demonstrating moderate to strong staining;
D. Hormone refractory METs demonstrating strong staining;
E. PCa demonstrating moderate to strong staining associated with stromal inflammatory component (yellow arrows point to areas of inflammation);
F. Benign glands demonstrating strongly staining luminal secretions (black arrows). All photomicrographs are at 100× magnification. Panel E has been further enlarged ×4 to illustrate area of inflammatory infiltrate concomitant with CXCL5 protein expression.
G. Boxplot depicting median product score distributions of protein expression levels for benign glands, malignant glands from primary prostate tumors (PCa) and malignant areas from prostate metastases (METs) and p-values associated with the statistical evaluation of these distributions.

Figure 21:
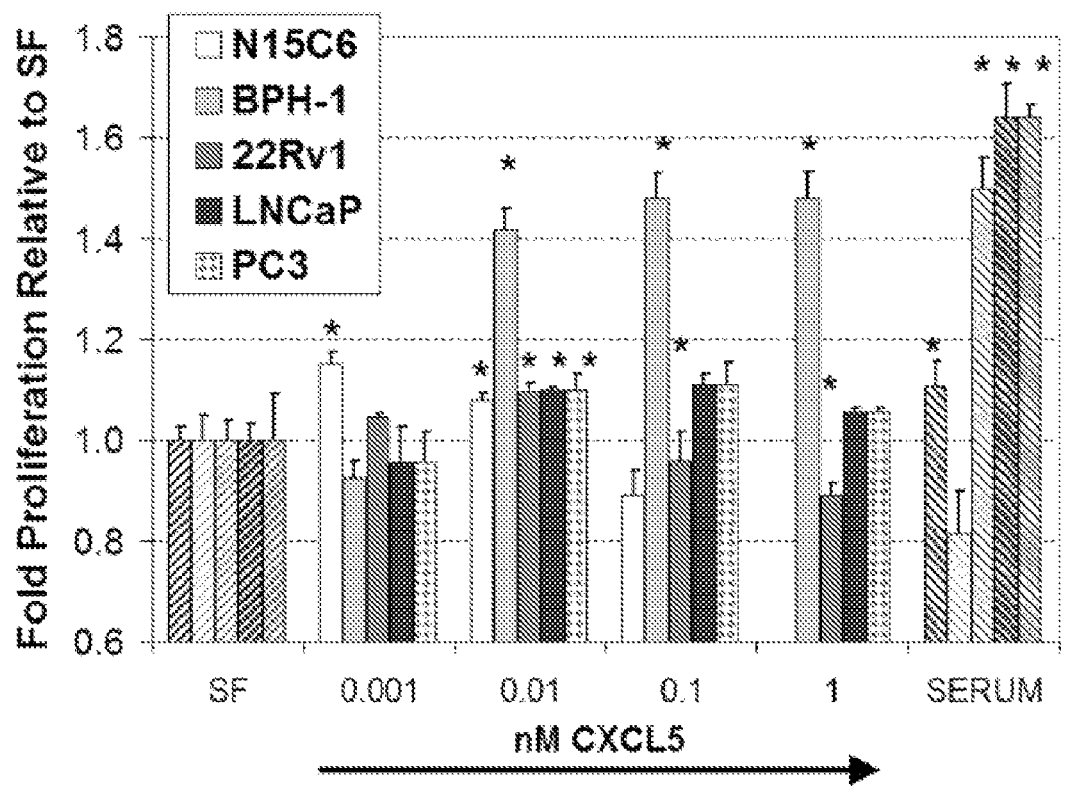

FIG. 21 shows that prostate epithelial cells proliferate in response to CXCL5. Non-transformed N15C6 (white bars) or BPH-1 (light gray bars), or transformed androgen-sensitive 22Rv1 (dark grey bars) or LNCaP (black bars) or androgen insensitive PC3 (white bars with gray diamonds) transformed prostate epithelial cells proliferated to significantly higher levels when grown in serum-free media (SF) supplemented as shown with 0.001-1 nM CXCL5 (*, $p<0.05$) than the same cells grown in SF media alone. Proliferation in complete media (SERUM) relative to SF media is shown for comparison and as a positive control. All data is shown normalized to growth in un-supplemented SF media, which was set at 1-fold.

Figure 22:
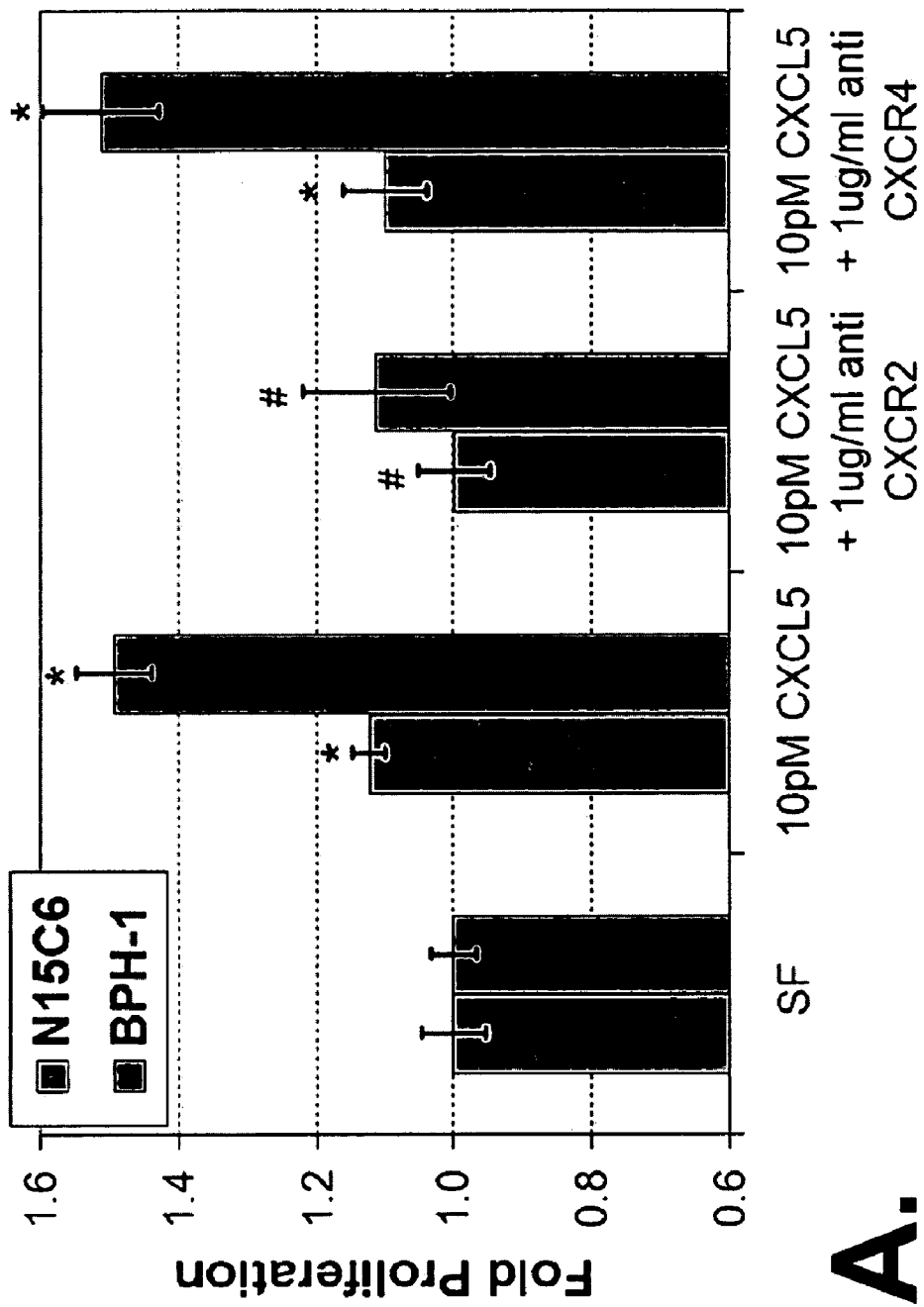
Figure 22:
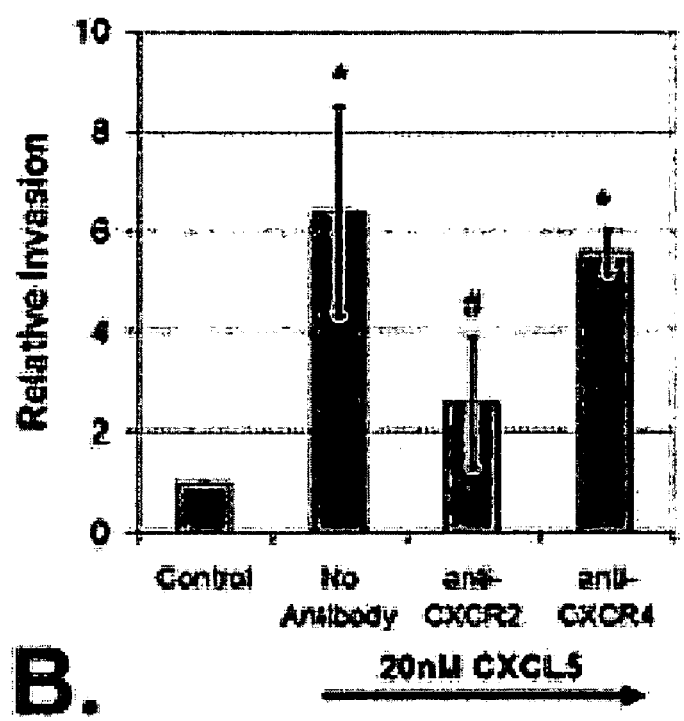

FIG. 22 shows specificity of CXCL5-stimulated proliferative and invasive responses. FIG. 22A. N15C6 (light gray bars) or BPH-1 (dark gray bars) non-transformed prostate epithelial cells proliferated to significantly higher levels when grown for 72 hours in serum-free HIE media (SF HIE) media supplemented with 10 pM CXCL5 than those grown in SF HIE alone (p<0.001, indicated by *). Pre-incubation of the cells for one hour with 1 ug/ml antibody against CXCR2, the receptor for CXCL5, followed by supplementation with CXCL5 and maintenance of growth in CXCL5+anti-CXCR2-containing media significantly ablated the proliferative response (p<0.001, indicated by #). In contrast, cellular growth following pre-incubation with an antibody against an unrelated chemokine receptor, CXCR4, followed by supplementation with CXCL5 and maintenance of growth in CXCL5+anti-CXCR4-containing media was similar to that observed for non-pre-treated cells grown in CXCL5-supplemented media, and was significantly higher than that in serum-free HIE media alone (p<0.001, indicated by *). All data is shown normalized to growth in un-supplemented SF HIE media, which was set at 1-fold. FIG. 22B. Significantly more PC3 cells migrated through the synthetic basement membrane, Matrigel, in response to 20 nM CXCL5 ("No antibody") than vehicle (control, set at 1-fold) (*p<0.05). Invasion through Matrigel was significantly inhibited by pre-treatment with 1 ug/ml blocking antibody (anti-CXCR2) (#p<0.05) but not by pre-treatment with non-specific antibody (anti-CXCR4) (*p<0.05).

Figure 23:
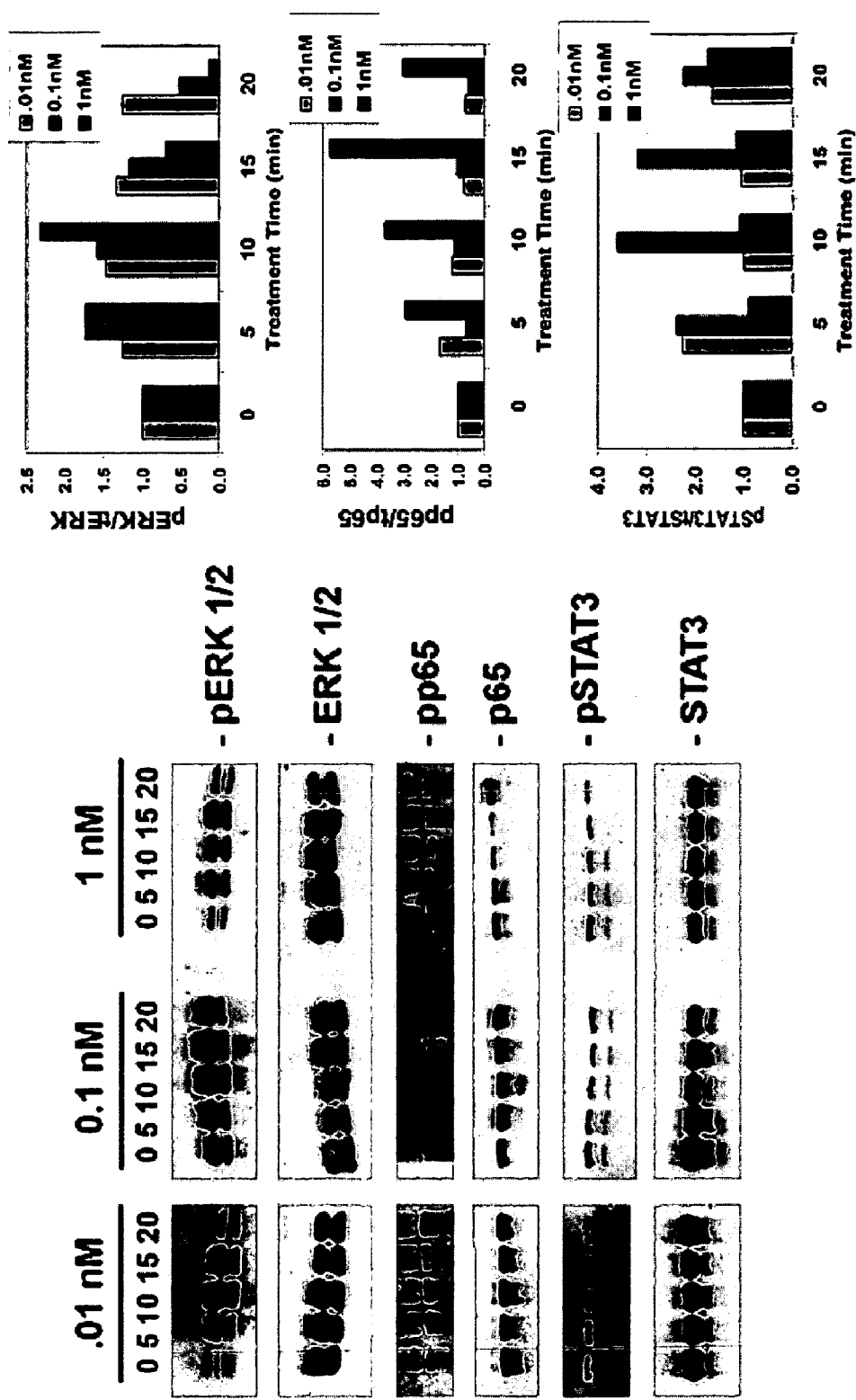

FIG. 23 shows that CXCL5 activates both MAPK and PI3K signaling in non-transformed N15C6 prostate epithelial cells. Non-transformed N15C6 cells rapidly and transiently phosphorylated ERK ½ and STAT3 when treated with either sub-nanomolar (10 pM or 100 pM) or nanomolar (1 nM) levels of CXCL5, whereas NFkappaB subunit activation was evident only after treatment with 1 nM CXCL5. Primary antibody concentrations used were 1:500 for phosphoERK, 1:500 for phosphop65 (NFkappaB), 1:1000 for phosphoS-TAT3, 1:1000 for total ERK, 1:1000 for total p65 and 1:2000 for total STAT3. Immunoblots are shown on the left, and corresponding densitometric evaluations of the same blots are shown on the right. Phosphorylation relative to total protein quantitated from the immunoblot is shown in the densitometry plots as phospho/total protein.

Figure 24:
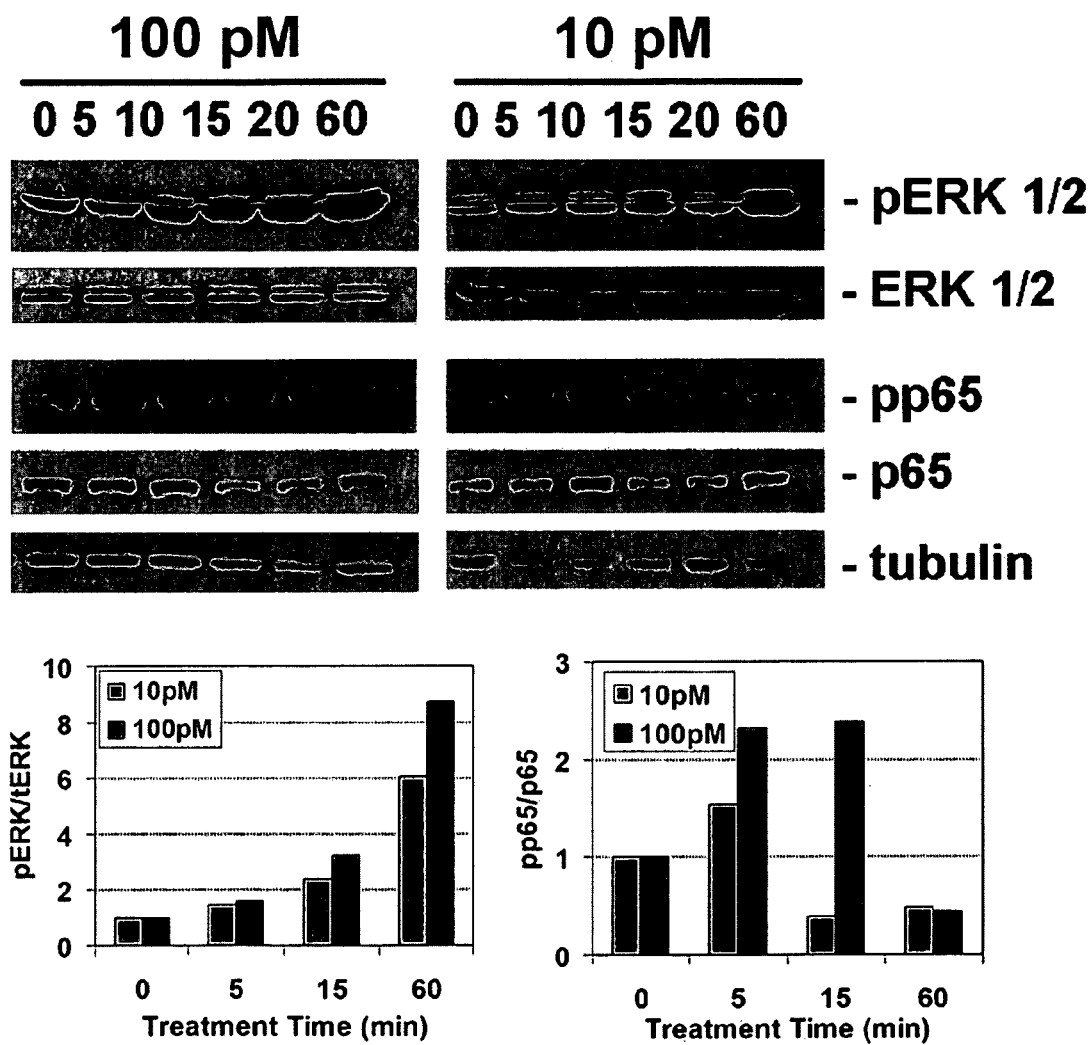

FIG. 24 shows that CXCL5 activates both MAPK and PI3K signaling in transformed LNCaP prostate epithelial cells. Transformed LNCaP cells rapidly and transiently phosphorylated both ERK ½ and the p65 subunit of NFkappaB upon treatment with sub-nanomolar (10 pM or 100 pM) levels of CXCL5. Immunoblots are shown in the top panel, and corresponding densitometric evaluations of the same blots are shown in the bottom panel. Phosphorylation relative to total protein quantitated from the immunoblot is shown in the densitometry plots as phospho/total protein.

Figure 25:
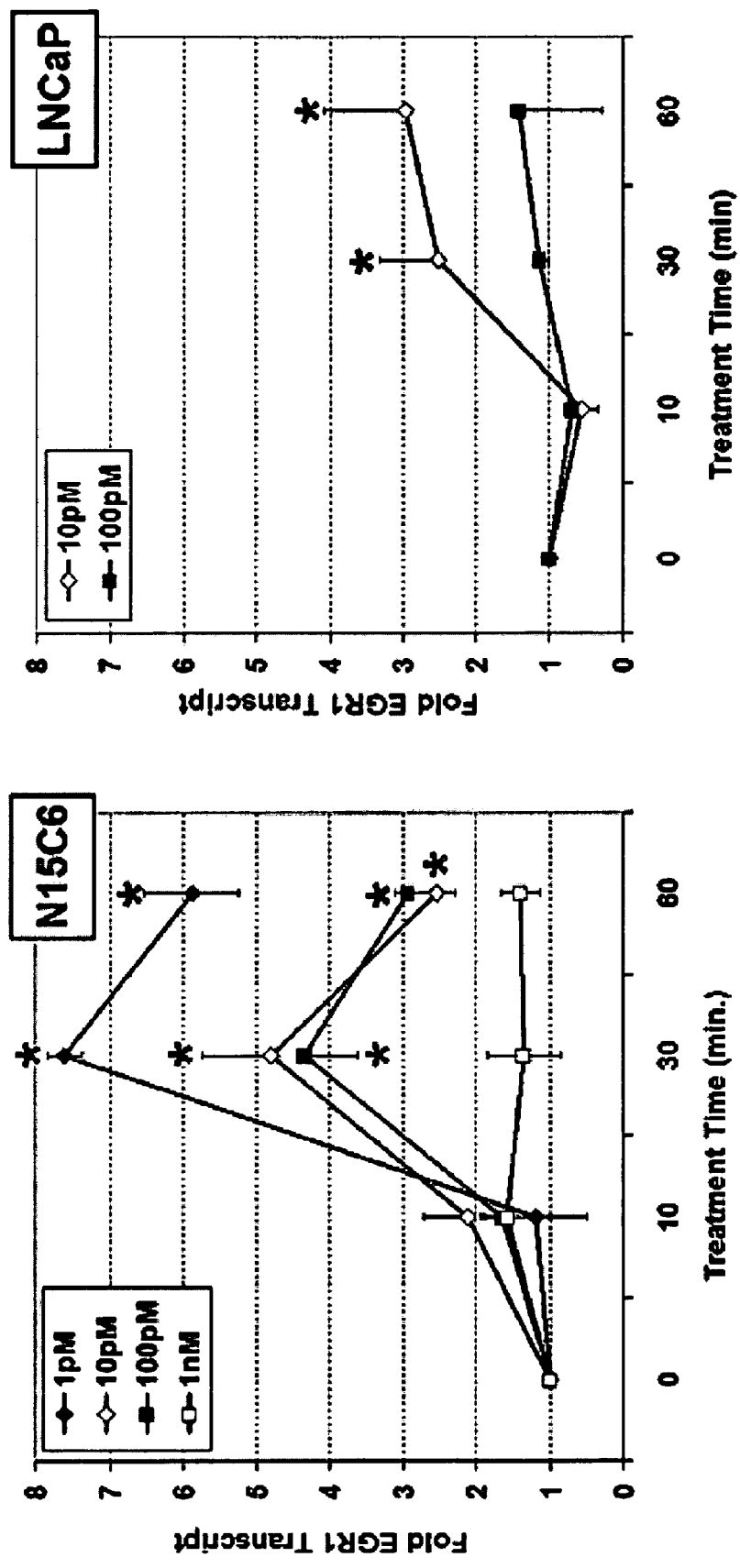

FIG. 25 shows that CXCL5 stimulates a transcriptional response in both non-transformed and transformed prostate epithelial cells. Quantitative real-time PCR of RNA purified from N15C6 cells (left) or LNCaP cells (right) treated with sub-nanomolar CXCL5 as shown demonstrates rapid and robust transcription of the EGR1 gene significantly higher than levels obtained at time 0 (set at 1-fold) (p<0.05, indicated by *). Data shown is averaged over three or more separate experiments per time point per concentration of CXCL5 examined.

Figure 26:
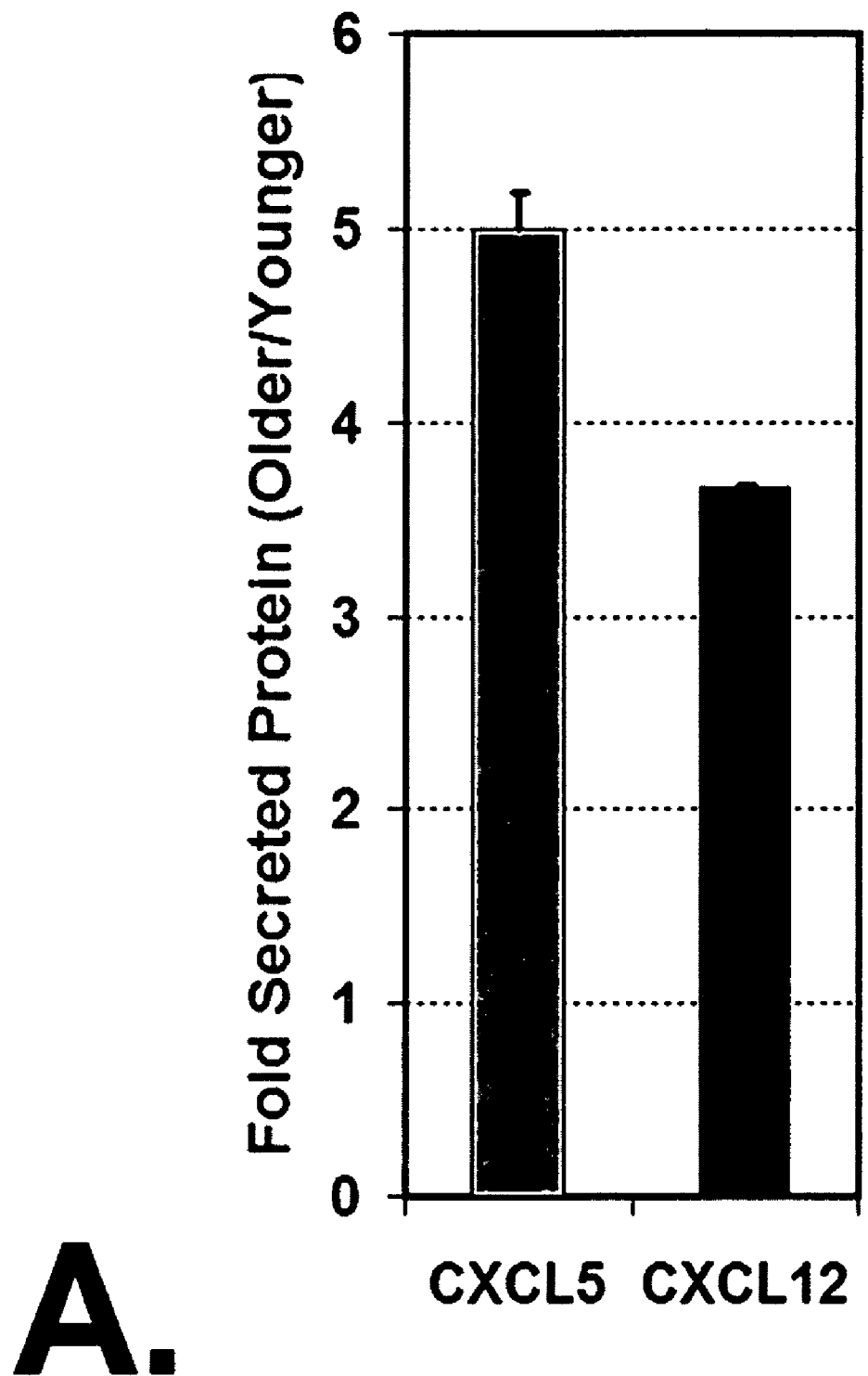

FIG. 26 shows prostate stromal fibroblasts cultured from older men secrete higher levels of CXCL5 and CXCL12 than those cultured from younger men. Primary stromal fibroblasts cultured from the peri-urethral area of the prostates from five younger (aged 40-52) or five older (aged 63-81) patients were grown as described, media collected and evaluated by ELISA for secreted CXCL5 and CXCL12. The graph shows the average secreted CXCL5 (grey bar) and CXCL12 (black bar) for older compared to younger primary prostate stromal fibroblasts.

Figure 27:
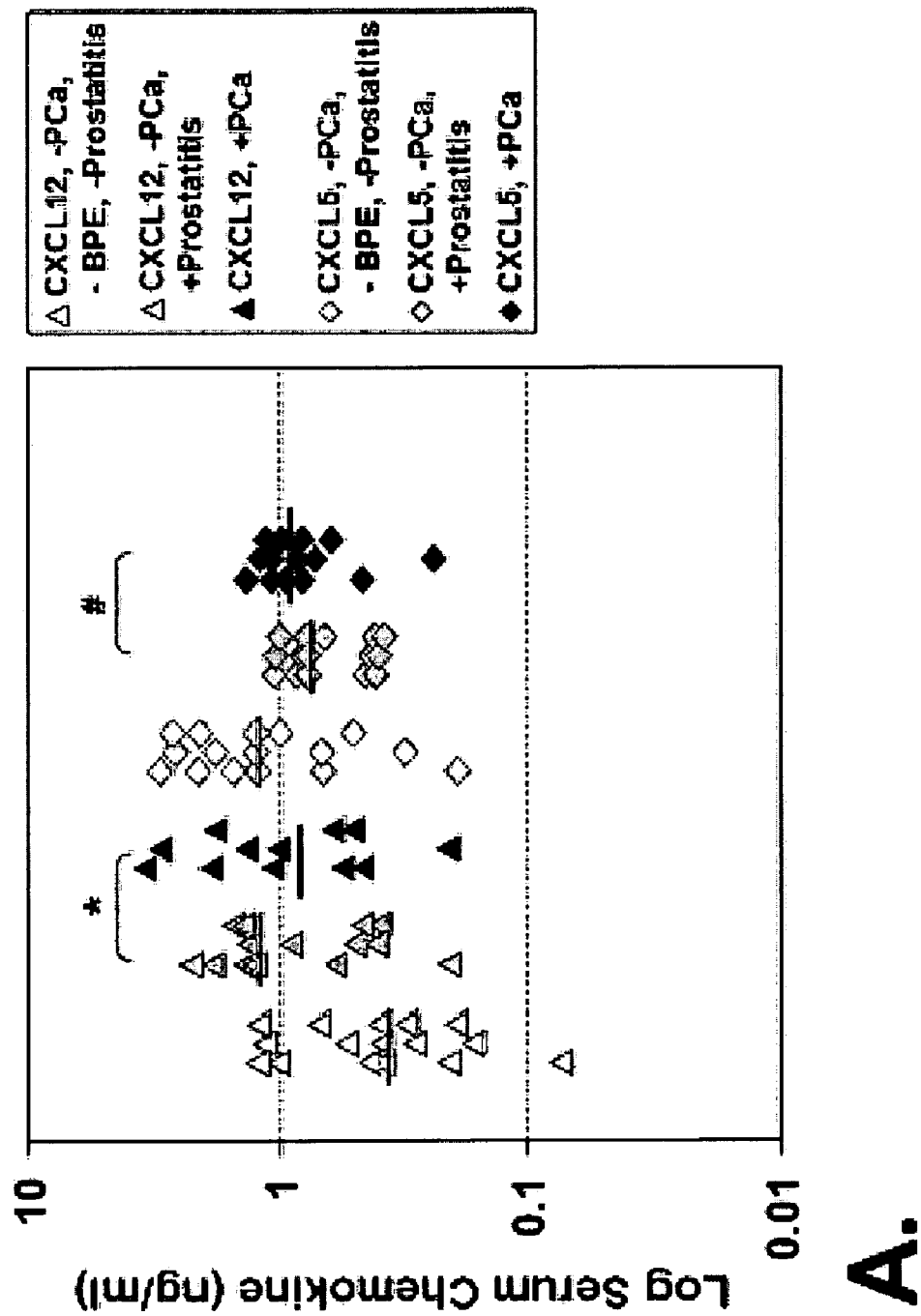
Figure 27:
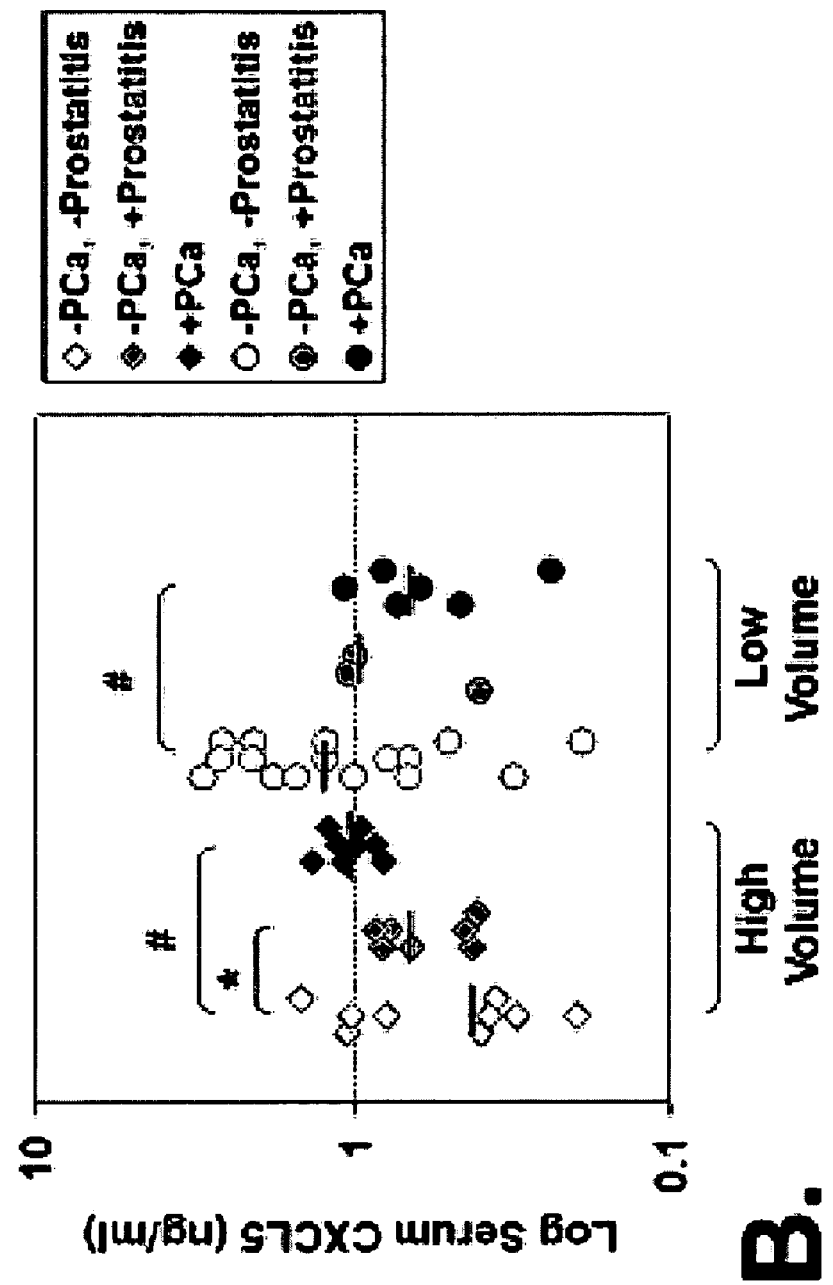
Figure 27:
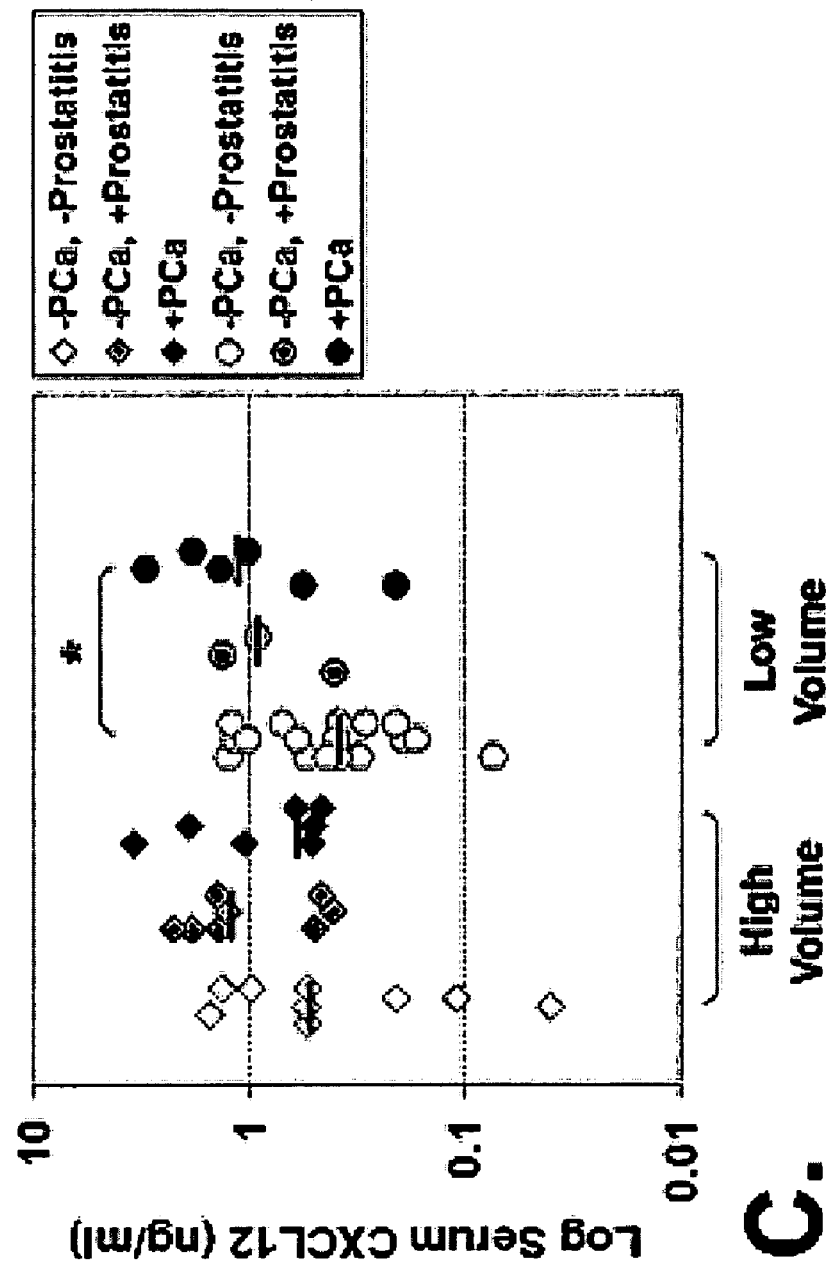
Figure 27:
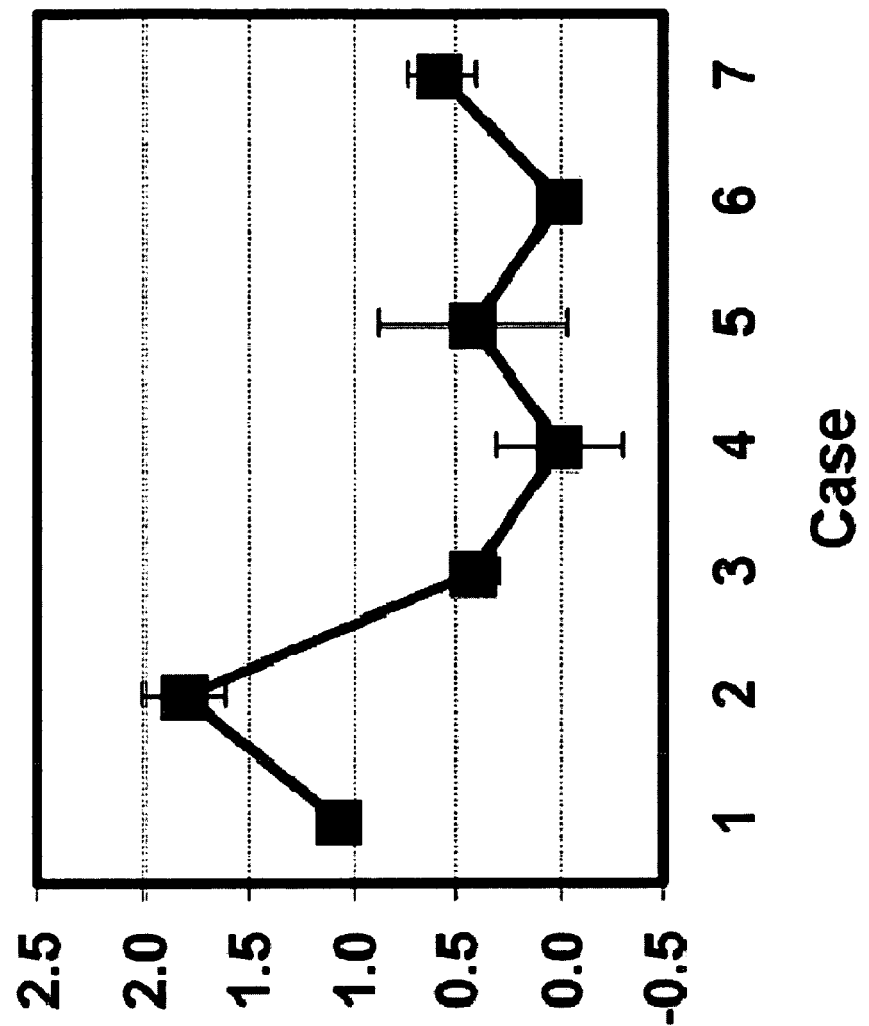

FIG. 27A shows that log serum CXCL5 or CXCL12 (ng/ml) differs depending on prostate disease status. ELISA-derived values for serum CXCL12 for men without evidence of prostatic disease (white triangles), men without cancer but with histological prostatitis (grey triangles) and men with prostate cancer (black triangles), as well as the log serum CXCL5 for men without evidence of prostatic disease (white diamonds), men without cancer but with histological prostatitis (grey diamonds) and men with prostate cancer (black diamonds) are shown on a logarithmic scale. Significant differences (p<0.050) are indicated by *, trends (0.065<p<0.050) by #.

FIG. 27B shows log serum CXCL5 (ng/ml) relevant to prostate volume. ELISA-derived values for serum CXCL5 for men with low volume (<37.5 g) (circles) or high volume (>37.5 g) (diamonds) prostates without cancer or histological prostatitis (white), without cancer but with histological prostatitis (grey), or with cancer (black) are shown on a logarithmic scale. Differences between groups that achieved statistical significance (p<0.05) is indicated by *; trends by #. The data represented here is drawn from Table V.

FIG. 27C shows log serum CXCL12 (ng/ml) relevant to prostate volume. ELISA-derived values for serum CXCL12 for men with low volume (<37.5 g) (circles) or high volume (>37.5 g) (diamonds) prostates without cancer or histological prostatitis (white), without cancer but with histological prostatitis (grey), or with cancer (black) are shown on a logarithmic scale. Differences between groups that achieved statistical significance (p<0.05) is indicated by *; trends by #. The data represented here is drawn from Table V.

FIG. 27D shows a comparison of serum CXCL12 at the time of prostate needle biopsy and post-prostatectomy. Shown is the ratio of serum CXCL12 values for seven patients obtained post-prostatectomy to those obtained at the time of prostate needle biopsy. Ratios equal to 1 signify equivalent serum CXCL12 values (case #1), >1 signify post-prostatectomy values greater than those obtained at needle biopsy (case #2), and <1 signify post-prostatectomy values less than those obtained at needle biopsy (cases 3-7).

Figure 28:
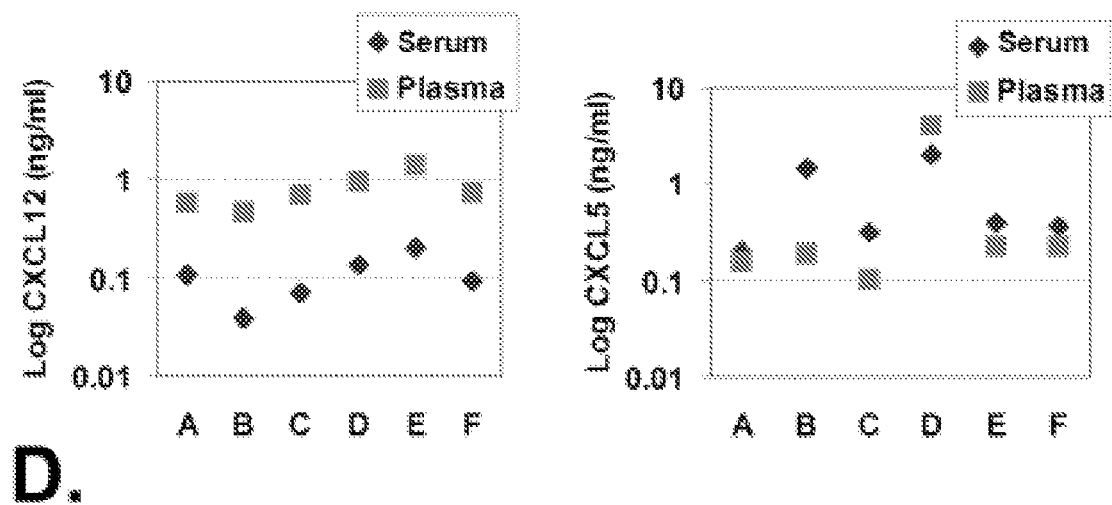

FIG. 28 shows log Chemokine Values in Serum and Plasma. ELISA-derived values for CXCL12 (LEFT) or CXCL5 (RIGHT) from serum (diamonds) or plasma (squares) are shown on a logarithmic scale for 6 of the 51 patients examined.

DEFINITIONS

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "specifically binding to CXCL1, CXCL5, CXCL6, and/or CXCL12 with low background binding" refers to an antibody that binds specifically to CXCL1, CXCL5, CXCL6, and/or CXCL12 protein (e.g., in an immunohistochemistry assay) but not to other proteins (e.g., lack of non-specific binding).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the terms "prostate disorder," "disorder of the prostate" or similar terms refers to a disease, disorder, or condition associated with prostatic function and/or activity. Examples include, but are not limited to, benign prostatic hypertrophy (BPH), prostatitis, prostate cancer—localized and metastatic (Pca), and prostatic intraepithelial neoplasi (PIN).

As used herein, the term "subject is suspected of having benign prostatic hypertrophy (BPH)" refers to a subject that presents one or more symptoms of BPH or is being screened for BPH. A subject suspected of having BPH may also have one or more risk factors associated with BPH (e.g., elevated CXCL1, CXCL5, CXCL6, and/or CXCL12 activity). A "subject suspected of having BPH" is sometimes diagnosed with BPH and is sometimes found to not have BPH.

As used herein, the term "subject is suspected of having prostatitis" refers to a subject that presents one or more symptoms of prostatitis or is being screened for prostatitis. A subject suspected of having prostatitis may also have one or more risk factors associated with prostatitis (e.g., elevated CXCL1, CXCL5, CXCL6, and/or CXCL12 activity). A "subject suspected of having prostatitis" is sometimes diagnosed with prostatitis and is sometimes found to not have prostatitis.

As used herein, the term "subject is suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a digital rectal exam revealing a prostatic nodule or a detectable serum PSA value) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with BPH" refers to a subject who has been tested and found to have prostatic cells suffering from BPH. BPH may be diagnosed using any suitable method, including but not limited to, evidence of urinary obstruction, difficulty in voiding, enlarged prostate, and the diagnostic methods of the present invention.

As used herein, the term "subject diagnosed with prostatitis" refers to a subject who has been tested and found to have prostatic cells suffering from prostatitis. Prostatitis may be diagnosed using any suitable method, including but not limited to detection of microorganisms in prostatic secretions, reports of pain localized to the prostate, biopsy, test, and the diagnostic methods of the present invention.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "initial diagnosis" refers to a test result of initial cancer, prostatitis, or BPH diagnosis that reveals the presence or absence of cancerous cells or cells suffering from prostatitis and/or BPH (e.g., using a biopsy and histology). An initial diagnosis does not include information about the stage of the disorder (e.g., cancer, BPH) or the risk of, for example, metastasis.

As used herein, the term "post surgical tumor tissue" refers to cancerous tissue (e.g., from a tissue or organ) that has been removed from a subject (e.g., during surgery).

As used herein, the terms "identifying the risk of said tumor metastasizing" and "identifying the risk of said cancer metastasizing" refer to the relative risk (e.g., the percent chance or a relative score) of a tumor (e.g., solid tumor tissue) or cancer (e.g., prostate cancer cells) metastasizing.

As used herein, the term "identifying the risk of said tumor recurring" refers to the relative risk (e.g., the percent chance or a relative score) of a tumor (e.g., tumor associated with prostate cancer) recurring in the same tissue or location (e.g., organ) as the original tumor (e.g., tissue or organ).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer. Cancers may be characterized by the identification of increased, decreased or static CXCL1, CXCL5, CXCL6, and/or CXCL12 expression levels in cancer cells and tissues.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression, or lack thereof, of CXCL5 and/or CXCL12.

As used herein, the term "reagent(s) capable of specifically detecting CXCL chemokine expression, CXCL receptor expression, and/or pathway related compound expression" refers to reagents used to detect the expression of CXCL chemokine expression (e.g., CXCL1, CXCL5, CXCL6, and/or CXCL12), CXCL receptor expression (e.g., CXCR1, CXCR2, CXCR4, CXCR7), and/or related compound expression (e.g., NF-kappaB, ERK ½, ELK-1). Examples of suitable reagents include, but are not limited to, nucleic acid probes capable of specifically hybridizing to CXCL1, CXCL5, CXCL6, and/or CXCL12 mRNA or cDNA, CXCR1, CXCR2, CXCR4 and/or CXCR7 mRNA or cDNA, and NF-kappaB, ELK-1 and/or ERK ½ mRNA or cDNA, and related antibodies (e.g., monoclonal antibodies of the present invention). (e.g., CXCR1 Ab (Abcam #Ab13018), CXCR4 Ab (Abcam #Ab10403), CXCR2 Ab (Abcam #24963), CXCR7 Ab (Abcam #Ab12870, Abcam #Ab12871, Abcam #38089)).

As used herein, the term "instructions for using said kit for detecting cancer in said subject" includes instructions for using the reagents contained in the kit for the detection and characterization of cancer in a sample from a subject.

As used herein, the term "providing a prognosis" refers to providing information regarding the impact of the presence of a prostate disorder (e.g., BPH, prostatitis, prostate cancer) (e.g., as determined by the diagnostic methods of the present invention) on a subject's future health (e.g., expected morbidity or mortality, the likelihood of getting cancer, the likelihood of getting BPH, prostatitis, and/or PCa, and the risk of metastasis).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "effective amount" refers to the amount of a composition (e.g., inhibitor of CXCL1, CXCL5, CXCL6, and/or CXCL12) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) (e.g., CXCL5 siRNAs or antibodies and one or more other agents—e.g., an anti-cancer agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., CXCL5 antibody) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference in its entirety).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethane-sulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "gene transfer system" refers to any means of delivering a composition comprising a nucleic acid sequence (e.g., CXCL5 siRNA) to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., prostate cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

DETAILED DESCRIPTION OF THE INVENTION

The direct relationship between the aging process and the incidence and prevalence of both prostate cancer (PCa) and benign prostatic hypertrophy (BPH) indicates that certain risk factors associated with the development of both diseases increase with the aging process. BPH, or noncancerous enlargement of the prostate, is a common condition associated with aging in men (Meigs J B, et al., (2001) J. Clin. Epidemiol. 54, 935-944; Verhamme K M, et al., (2002) Eur. Urol. 42, 323-328; Neuhouser M L, et al., (2004) Urology 64, 201-211; incorporated herein by reference in their entireties). PCa is a particular form of cancer classified as an adenocarcinoma, or glandular cancer, that begins when, for example, normal semen-secreting prostate gland cells mutate into cancer cells.

PCa and BPH share an overly proliferative phenotype, indicating that the mechanisms normally acting to suppress cellular proliferation are disrupted or rendered dysfunctional as a consequence of the aging process. Studies both in vivo and in vitro report higher proliferative and lower apoptotic rates for epithelial cells from hyperplastic prostates compared with normal prostates, indicating that some proportion of increased prostate volume with age is attributable to increased epithelial cell densities (Berges R R, et al., (1995) Clin. Cancer Res. 1, 473-480; Colombel M, et al., (1998) Br. J. Urol. 82, 380-385; Arenas M I, et al., (2001) Int. J. Andrology 24, 37-47; incorporated herein by reference in their entireties). However, the molecular mechanisms responsible for increased epithelial cell proliferation in hyperplastic human prostates are not well described. Work accomplished using rodent and rodent/human in vivo and in vitro models indicate that paracrine interactions between glandular epithelial cells and adjacent fibroblastic stromal cells play a role in the development of prostate disorders such as BPH and PCa (Thompson T C, et al., (1989) Cell 56, 917-930; Merz V W, et al., (1991) Mol. Endocrinol. 5, 503-513; Cunha G R, et al., (1996) Acta Anat. 155, 63-72; Foster B A, et al., (1999) Cancer Metastasis Rev 17, 317-324; Hayward S W, et al., (1998) Differentiation 63, 131-140; Song Z, et al., (2002) Cancer Res. 62, 5096-5105; incorporated herein by reference in their entireties).

In order to create a human based system for the study of paracrine interactions during prostate tumorigenesis, an in vivo system using human in vitro models has been developed. Successful efforts have utilized cocultured normal human prostate-derived fibroblasts and the LNCaP prostate metastasis-derived cell line (Olumi A F, et al., (1998) Cancer Res. 58, 4525-4530; incorporated herein by reference in its entirety). These studies demonstrated that epithelial-stromal paracrine interactions were required for xenografted LNCaP cells to fully express the malignant phenotype and grow as tumors in athymic mice (Olumi A F, et al., (1998) Cancer Res. 58, 4525-4530; incorporated herein by reference in its entirety). The in vivo and in vitro studies described above show that epithelial-stromal interactions are crucial for the regulation of epithelial cell growth. However, because the etiologies of BPH and PCa are clearly associated with aging, the change in epithelial-stromal interactions in the human prostate change over time and how such changes contribute to the development of hypertrophy and cancer was investigated.

Experiments conducted during the course of the present invention examined the effects of an aging microenvironment on paracrine interactions and prostatic epithelial cell proliferation. For these experiments, a novel in vitro model system for benign prostatic hypertrophy was developed. The epithelial component of this model, N15C6 cells, was developed from immortalized primary normal prostate epithelial cells. The stromal component consisted of stromal fibroblastic cell populations cultured from the prostates of patients aged 40-52 years (younger) or 63-81 years (older) at the time of surgery. Experiments accomplished using this model indicated that stromal fibroblast cells cultured from the prostates of older men were less able to suppress epithelial cell proliferation than those cultured from the prostates of younger men. Moreover, older fibroblasts expressed and secreted higher levels of the CXCL chemokines (e.g., CXCL1, CXCL2, CXCL3, CXCL4, CXCL5, CXCL6, CXCL7, CXCL8, CXCL9, CXCL10, CXCL11, CXCL12, CXCL16) compared with younger fibroblasts, and the chemokine protein was mechanistically associated with enhanced epithelial cell proliferation. In particular, experiments conducted during the course of the present invention demonstrated that older fibroblasts expressed and secreted higher levels of the CXCL5 and/or CXCL12 compared with younger fibroblasts, and the CXCL5 and/or CXCL12 protein was mechanistically associated with enhanced epithelial cell proliferation. In addition, experiments conducted during the course of the present invention indicated that varying levels of the chemokine CXCL5 and/or CXCL12 are expressed in prostate cancer cells depending upon the status of the cells. For example, prostate cancer cells undergoing metastasis express higher levels of the chemokine CXCL5 and/or CXCL12 (e.g., in the nanomolar range) than prostate cancer cells undergoing proliferation (e.g., in the picomolar range). In particular, experiments conducted during the course of the present invention showed that CXCL12 expression levels as low as 1-5 pM for N15C6 and 50-500 pM for LNCaP prostate epithelial cells stimulated cellular proliferation, and that higher expression levels for such cells were inhibitory to cellular proliferation. In addition, experiments conducted during the course of the present invention showed that CXCL12 expression levels in the nanomolar range induced prostate epithelial cell motility and invasiveness.

Experiments conducted during the course of the present invention showed that a CXCL12-mediated proliferative response and/or CXCL12-mediated proliferative response is ERK-dependent. CXCL12 and CXCL5 were shown to initiate a complex, global transcriptional response in prostate epithelial cells that affected genes encoding proteins directly involved in the promotion of cellular proliferation and progression through the cell cycle, tumor metastasis, and cellular motility, or in the repression of genes encoding proteins involved in cell-cell adhesion resistance to apoptosis. CXCL12 and CXCL5 were shown to influence expression of a proliferative and/or transformed cellular phenotype at many levels, and to perform a role in the etiology of benign and malignant prostatic diseases.

Detection rates for prostate cancer in men demonstrating total serum PSA values greater than 10 ng/ml are typically 70% or higher when combined with findings of abnormal digital rectal exam (DRE) or with histological evidence based on >6 needle biopsy specimens (see, e.g., Luciani L G, et al., Urology 2006; 67:555-8; Inahara M, et al., Urology 2006; 68:815-9; each herein incorporated by reference in their entireties). These rates, however, are much lower for men demonstrating total serum PSA (tPSA) values of <10 ng/ml. For example, malignant glands were detected on needle biopsy for ~30% of men whose tPSA values were between 4-10 ng/ml, and tumor detection fell to 21-23% among men with detectable tPSA values of <4 ng/ml (see, e.g., Kravchick S, et al., Urology 2005; 66:542-6; Pelzer A E, et al., Urology 2005; 66:1029-33; Gilbert S M, et al., Urology 2005; 65:549-53; each herein incorporated by reference in its entirety). This suggests that factors other than cancer may contribute to the elevation in PSA in the serum. Indeed, elevated serum tPSA values correlate directly with histological evidence of inflammation on needle biopsy in patients asymptomatic for prostatitis (see, e.g., Simardi L H, et al., Urology 2004; 64:1098-101; herein incorporated by reference in its entirety). Total and other forms of serum PSA were shown to be elevated in men diagnosed with chronic prostatitis/chronic pelvic pain syndrome. Importantly, this study determined that total and other forms of serum PSA alone did not demonstrate sufficient sensitivity and specificity for use as diagnostic markers for chronic prostatitis/chronic pelvic pain syndrome (see, e.g., Nadler R B, et al., Urology 2006; 67:337-42; herein incorporated by reference in its entirety). Lastly, larger prostate volume may contribute to elevated tPSA values in the absence of cancer. It has been shown that a smaller prostate volume is a strong predictor of cancer detection in men exhibiting tPSA levels in the 2.0 to 9.0 ng/ml range, suggesting that tPSA is less useful for the prediction of cancer in men with concurrent BPH (see, e.g., Al-Azab R, et al., Urology 2007; 69:103-7; herein incorporated by reference in its entirety). It has been shown that serum tPSA values increase concomitantly with patient age in parallel with increased incidence of BPH (see, e.g., Roehrborn C G, et al., Nov. 5, 2007 In Press, The Prostate 19; Wright E J, et al., J. Urol. 2002; 167:2484-7; discussion 2487-8; Berger A P, et al., Urology 2003; 62:840-4; Berger A P, et al., Urology 2007; 69:134-8; Pinsky P F, et al., Urology 2006; 68:352-6; each herein incorporated by reference in their entireties).

Experiments conducted during the course of development of embodiments for the present invention, total serum CXCL12 levels were shown to be significantly higher for men who were biopsy-positive compared to those who were biopsy-negative for cancer and histological prostatitis (p=0.050), and were reduced or ablated in 5/7 (71%) men after removal of the cancerous prostate. Among men who were biopsy-negative for prostate cancer, total serum CXCL5 levels were inversely associated with prostate volume and were significantly higher in men with concomitant BPH and histological prostatitis compared to those without evidence of prostatic disease (p<0.003). As such, serum CXCL5 and CXCL12 levels were shown to differentially distinguish between BPH and PCa among patients presenting with low (<10 ng/ml) serum prostate specific antigen (PSA) and may potentially be used to facilitate decisions to perform diagnostic needle biopsy in this patient population.

Accordingly, the present invention relates to compositions and methods for the detecting, treating, and empirically investigating cellular proliferation disorders and cellular motility disorders. In particular, the present invention provides compositions and methods for using CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK ½, ELK-1) in the diagnosis, treatment, and empirical investigation of prostate disorders (e.g., prostate cancer, benign prostatic hypertrophy, prostatitis). Accordingly, the present invention provides methods for distinguishing (e.g., diagnosing, detecting) between BPH and PCa through measuring CXCL5 and CXCL12 serum levels in subjects presenting with low PSA. Accordingly, the present invention provides methods for diagnosing BPH and PCa through measuring CXCL5 and CXCL12 serum levels in subjects presenting with low PSA, such that PCa is associated with higher CXCL12 serum levels than CXCL5 serum levels, and BPH is associated with higher CXCL5 serum levels than CXCL12 serum levels.

Exemplary compositions and methods of the present invention are described in more detail in the following sections: I. CXCL Chemokines; II. Detection of Prostate Disorders; III. In vivo Imaging; IV. Antibodies; V. Therapeutics; VI. Pharmaceutical Compositions; VII. Drug Screening; and VIII. Kits.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is incorporated herein by reference in their entireties.

I. CXCL Chemokines

The chemokines are a superfamily of small molecules, produced by many different cell types of the body. To date, there are 45 known human chemokines and 18 receptors (Bacon K, et al., (2002) J Interferon Cytokine Res 22:1067-1068; incorporated herein by reference in its entirety). The chemokines typically include a conserved structure with four cysteines that form two disulfide bonds. The CXC subfamily of Chemokines (e.g., including CXCL1, CXCL5, CXCL6, and CXCL12) has an amino acid between the first two cysteines. Chemokines are characterized through their ability to chemoattract cells. Chemokines have also been implicated in a variety of fields including infectious disease such as HIV (e.g., the chemokine receptors CXCR4 and CCR5 are coreceptors for the AIDS virus), control of immune responses, and many other areas including organ development. Furthermore, they are produced by a variety of cells and organs in the body.

The genes for homeostatic chemokines (e.g., CXC chemokines) are located in discrete chromosomal locations, and they also tend to have a single ligand/receptor relationship. For example, CXCR1 is the receptor for CXCL1 (also known as GROα) and CXCL8 (also known as IL-8); CXCR2 is the receptor for CXCL1, CXCL2 (also known as GROβ), CXCL3 (also known as GROγ), CXCL5 (also known as ENA-78), CXCL6 (also known as GCP-2), and CXCL7 (also known as LDGF-PBP); CXCR3 is the receptor for CXCL9 (also known as Mig), CXCL10 (also known as IP-10) and CXCL11 (also known as I-TAC); CXCR4 and CXCR7 are receptors for CXCL12 (also known as SDF-1α and SDF-1β); CXCR5 is the receptor for CXCL13 (also known as BLC/BCA-1); CXCR6 is the receptor for CXCL16 (also known as BUNZO/STRC33); and the receptor for CXCL4 (also known as PF4) is unknown (see, e.g., Appendix IV of "Immunobiology: the immune system in health and disease" Fifth Edition (Janeway, Jr, et al, 2001); incorporated herein by reference in its entirety).

The expression of CXC chemokines and the respective receptors is increased in cancer cells (Muller A, et al., (2001) Nature 410:50-56; incorporated herein by reference in its entirety). In experiments conducted during the development of embodiments of the present invention, it was shown that stromal fibroblast cells cultured from the prostates of older men were less able to suppress epithelial cell proliferation than those cultured from the prostates of younger men. Moreover, older fibroblasts expressed and secreted higher levels of the CXC chemokines compared with younger fibroblasts, and the chemokine protein was mechanistically associated with enhanced epithelial cell proliferation. In addition, experiments conducted during the course of the present invention indicated that varying levels of the chemokine CXCL5 and/or CXCL12 are expressed in prostate cancer cells depending upon the status of the cells. For example, prostate cancer cells undergoing metastasis express higher levels of the chemokine CXCL5 and/or CXCL12 (e.g., in the nanomolar range) than prostate cancer cells undergoing proliferation (e.g., in the picomolar range).

Accordingly, as described in more detail below, the present invention provides methods for diagnosing and treating prostate disorders (e.g., BPH, PCa). In some embodiments, the diagnosing involves detecting and/or quantifying chemokine expression (e.g., CXCL1, CXCL5, CXCL6, CXCL12). In some embodiments, the treating involves altering (e.g., reducing, inhibiting) chemokine activity. The methods are not limited to a particular form or type of treatment. In some embodiments, the treatment is a medical form of treatment, while in other embodiments, the treatment is an empirical (e.g., research based) form of treatment. In some embodiments, the treatment involves the alteration (e.g., reduction, inhibition) of epithelial cell proliferation through alteration (e.g., reducing, inhibiting) of chemokine activity. In some embodiments, the treatment involves the alteration (e.g., reduction, inhibition) of epithelial cell proliferation through alteration of chemokine activity combined with an addition form of treatment (e.g., chemotherapeutic treatment). In some embodiments, the treatment involves the alteration (e.g., reduction, inhibition) of cancerous epithelial cell metastasis through alteration (e.g., reducing, inhibiting) of chemokine activity. In some embodiments, the treatment involves the alteration of cancerous epithelial cell metastasis through alteration of chemokine activity combined with an additional form of treatment (e.g., chemotherapeutic treatment).

The present invention is not limited to the alteration of particular chemokines. In some embodiments, the chemokines are CXC chemokines. In some embodiments, the CXC chemokines include CXCL5 and/or CXCL12. In some embodiments, the alteration of chemokines involves the alteration (e.g., reduction, inhibition) of CXC chemokine receptors (e.g., CXCR1, CXCR2, CXCR3, CXCR4, and CXCR5). In some embodiments, the alteration of chemokines involves the alteration (e.g., reduction, inhibition) of related pathways (e.g., NF-kappaB, ERK ½, ELK-1) involved in CXC chemokine (e.g., CXCL12, CXCL5) expression. In some embodiments, the alteration of chemokines involves the alteration (e.g., reduction, inhibition) of genes upregulated (e.g., EGFR, CD44, ANKRD12, SSBP1, CCNT1, JMJD1C, HNRPD, GOPC, STRAP, DYX1C1) or downregulated (e.g., CDH1, CTNNB1, CPSF1, EXOSC6, ITGB4, LOXL2, SORBS3, GSR, RANGAP1, NUMA1, RBM14, BMP1, ERBB2, MAPRE3, DOCK9, ARPC4, MARCKS) in response to CXC chemokine (e.g., CXCL12, CXCL5) expression.

II. Detection of Prostate Disorders

The present invention provides methods of detecting prostate disorders (e.g., BPH, prostatitis, prostatic intraepithelial neoplasi (PIN), localized prostate cancer (PCa), metastatic prostate cancer (metPCa), etc.) comprising detecting and quantifying specific chemokine (e.g., CXCL5 and/or CXCL12) expression.

Benign prostatic enlargement (BPH) is a common benign proliferative condition associated with aging in men. BPH is pathologically characterized by cellular proliferation of the epithelial and stromal elements in the prostate gland. Positive histologic evidence of such proliferation permits the assessment of BPH as benign prostatic hypertrophy (BPH); however, otherwise it is more proper to refer to prostatic enlargement based on prostate volume as BPH. Clinically, BPH is distinguished by progressive development of lower urinary tract symptoms (LUTS), which are variable and can include nocturia, incomplete emptying, urinary hesitancy, weak stream, frequency and urgency to the development of acute urinary retention (see, e.g., Wei J T, et al., J. Urol. 2005 April; 173(4):1256-61; herein incorporated by reference in its entirety). For example, in a survey of 1709 men without cancer reported by the Massachusetts Male Aging Study, the frequency of clinical BPH (defined in terms of frequency/difficulty with urinating and evidence of an enlarged/swollen prostate) rose from 8.4% in men 38-49 years of age to 33.5% in men aged 60-70 years (p<0.001) (see, e.g., Meigs J B, et al., J Clin Epidemiol. 2001 September; 54(9):935-44; herein incorporated by reference in its entirety). Lower urinary tract symptoms (LUTS) are typically used as a surrogate measure for BPH. Using LUTS as a surrogate measure for BPH, the Triumph project in the Netherlands reported a 2.7% prevalence rate for BPH in men 45-49 years of age, which increased to 24% in men 80 years of age (see, e.g., Verhamme K, et al., Eur Urol 42: 323-328, 2002; herein incorporated by reference in its entirety). As such, age is a profound risk factor associated with the development of BPH.

Prostatitis, or inflammation of the prostate gland, is characterized by a diverse symptomology and a lack of firm diagnostic criteria (see, e.g., McNaughton Collins M, et al., Ann Intern Med. 2000 Sep. 5; 133(5):367-81; herein incorporated by reference in its entirety). Bacterial prostatitis, either acute or chronic, accounts for only 5-10% of all cases of prostatitis, and more than 90% of cases of prostatitis are chronic abacterial prostatitis. Even though bacteria are not identifiable in prostatic fluids or urine samples examined from such patients, antimicrobial therapy is frequently prescribed to men with genitourinary symptoms and a diagnosis of chronic prostatitis (see, e.g., Collins M M, et al., J. Urol. 1998 April; 159(4): 1224-8; herein incorporated by reference in its entirety). It is unclear whether patient age is a risk factor for prostatitis. Data from the Olmsted County study suggests that, among men with a previous diagnosis of prostatitis (e.g., suffering from chronic prostatitis) the cumulative probability of subsequent episodes of prostatitis increased proportionately with age (20%, 38%, and 50% among men 40, 60, and 80 years old, respectively) (see, e.g., Roberts R O, et al., Urology. 1998 April; 51(4):578-84; herein incorporated by reference in its entirety). In contrast, Collins et al. (1999) reported that data from the National Ambulatory Medical Care Surveys of 1990 to 1996 showed that patient visits for chronic prostatitis were more frequent for younger than older men (see, e.g., Collins M M, et al., Urology. 1999 May; 53(5):921-5; herein incorporated by reference in its entirety).

Data extracted from a questionnaire compiled in 1992 from participants of the Health Professionals Follow-Up Study showed that 5,053 of 31,681 (16%) of male respondents reported a history of prostatitis. 57.2% of men with prostatitis also reported a history of BPH, and men with prostatitis were younger than those with BPH (mean age 57.4 versus 66.4, p<0.0001) (see, e.g., Collins M M, et al., J. Urol. 2002 March; 167(3): 1363-6; herein incorporated by reference in its entirety). Another study by this group showed that 20% of men seeking medical treatment for chronic prostatitis complained of pain, e.g., lower back pain, perianal pain, or pain upon urination (see, e.g., Collins M M, et al., Urology. 1999 May; 53(5):921-5; herein incorporated by reference in its entirety). 80% of men seeking medical treatment for chronic prostatitis did not complain of pain, and their symptoms overlapped considerably with those of men seeking treatment for BPH. Moreover, although significantly more men seeking treatment for BPH complained of urinary symptoms, a full 18% of men seeking treatment for prostatitis also complained of urinary symptoms. Taken together, these data suggest that overlapping symptomatic complaints make a differential diagnosis of prostatitis or BPH extremely difficult for many patients complaining of lower urinary tract symptoms.

A primary reason for accurate diagnosis of prostatitis or BPH is, for example, proper disease management. This, in turn, hinges on, for example, the use of appropriate interventional strategies, which are very different for the two diseases. In recent years, the standard of care for the management of BPH has moved away from surgical interventions (e.g., transurethral resection of the prostate, or TURP), and towards the use of chemotherapeutic agents, for example, alpha-blockers (e.g., doxazosin and tamsulosin) and 5-alpha-reductase inhibitors (e.g., finasteride) either alone or in combination (see, e.g., Wei J T, et al., J. Urol. 2005 April; 173(4); herein incorporated by reference in its entirety). Such therapeutics act to reduce prostate volume (5-alpha-reductase inhibitors) and/or improve LUTS and urinary flow (5-alpha-reductase inhibitors and alpha-blockers) (see, e.g., Untergasser G, et al., Exp Gerontol. 2005 March; 40(3): 121-8; herein incorporated by reference in its entirety). In contrast to the chemotherapeutic strategies used to treat BPH, both acute and chronic prostatitis are frequently treated with antimicrobial therapies (e.g., Trimethoprim-Sulfamethoxazole or fluoroquinolones) (see, e.g., Williams D H, et al., Minerva Urol Nefrol. 2004 March; 56(1):15-31; herein incorporated by reference in its entirety). As such, there is a need to accurately diagnose prostatitis and BPH in order to avoid, for example, the use of non-overlapping, inappropriate chemotherapeutics. An additional reason to accurately distinguish between prostatitis and BPH is the annual direct costs incurred to treat these diseases are not trivial. A recent study published by the Chronic Prostatitis Collaborative Research Network estimated that the average annual direct medical costs incurred to treat prostatitis in the United States is $3,817, and analysis of data from the Urologic Diseases in America BPH project estimates that the average annual direct medical costs incurred to treat BPH is $2,577 (see, e.g., Calhoun E A, et al., Arch Intern Med. 2004 Jun. 14; 164(11):1231-6; Wei J T, et al., J. Urol. 2005 April; 173(4):1256-61; each herein incorporated by reference in their entireties). As such, improved diagnostic criteria could ensure that dollars spent on medical costs to treat prostatitis and BPH are appropriately and well-spent.

Objective criteria that facilitate the differential diagnosis of prostatitis or BPH are needed. Such objective criteria might be defined through the use of biomarkers that could be utilized on biological specimens obtained through non-invasive and/or minimally invasive procedures, and could sensitively and specifically identify patients suffering from prostatitis, BPH, or both conditions concurrently. Such biomarkers, used alone or in combination with other validated biomarkers (e.g., prostate-specific antigen (PSA)), could distinguish between patients suffering from benign prostatic diseases (prostatitis or BPH), and those suffering from prostatic malignancies.

There has been intense interest in the potential role of inflammation in the etiology of prostatitis and BPH. The presence of inflammatory cells in acute and chronic cases of prostatitis that have clear evidence of bacterial infection is not unexpected. For example, Hochreiter et al. (2000) reported that IL-8 and CXCL5 levels were frequently elevated in the expressed prostatic secretions from men diagnosed with bacterial prostatitis, inflammatory chronic pelvic pain syndrome, and asymptomatic inflammatory prostatitis compared to normal controls (see, e.g., Hochreiter W W, et al., Urology. 2000 Dec. 20; 56(6):1025-9; herein incorporated by reference in its entirety). It was hypothesized that because these cytokines are direct mediators of leukocyte accumulation and activation at inflammatory sites, they may be responsible, in part, for the presence of inflammatory reactions in the prostate (see, e.g., Hochreiter W W, et al., Urology. 2000 Dec. 20; 56(6):1025-9; herein incorporated by reference in its entirety). However, several studies have now shown that inflammation is common in the prostate, even in the absence of infectious agents. For example, Nickel et al. (1999) examined sectioned transurethral resection of the prostate (TURP) specimens from 80 consecutive patients with a diagnosis of BPH, but no history or symptoms of prostatitis (see, e.g., Nickel J C, et al., BJU Int. 1999 December; 84(9):976-81; herein incorporated by reference in its entirety). The sections were immunostained for leukocyte common antigen to detect inflammatory cells, and the number of inflammatory cells was quantitated using an image-analysis system. Inflammatory cells were detected in 90% of specimens examined, regardless of whether the patient had been catheterized for urinary retention prior to TURP, or whether bacterial growth resulted from cultured specimens. It was concluded that prostatic inflammation is a common histological finding in patients with BPH who have no symptoms of prostatitis, though the clinical significance of asymptomatic chronic prostatitis associated with BPH had yet to be determined.

In another study, Gerstenbluth et al. (2002) identified pervasive chronic prostatitis in whole mount radical prostatectomy specimens from a series of 40 consecutive patients with clinically localized prostate cancer (see, e.g., Gerstenbluth R E, et al., J. Urol. 2002 May; 167(5):2267-70; herein incorporated by reference in its entirety). Although inflammation was associated with BPH and cancer, it was observed more frequently associated with BPH. It was concluded that these findings indirectly supported a potential role for prostatitis in the pathogenesis of BPH.

Data recently reported by Roherborn (2005) obtained from examining baseline prostate biopsies in a subgroup of 1197 randomly selected patients in the MTOPS study demonstrated chronic inflammatory infiltrate in 30-60% of men with BPH (see, e.g., Roehrborn C G, et al., AUA Meeting 2005, Abstract #1277; herein incorporated by reference in its entirety). Patients with chronic inflammatory infiltrate had larger prostate volumes and demonstrated significantly more clinical progression and acute urinary retention than those who had no inflammation. This study concluded that, "More work is needed to better understand the role of chronic inflammation in the prostate, not only in cancer and carcinogenesis, but also in prostatitis and the natural history and progression of LUTS and BPH."

In experiments conducted during the development of embodiments for the present invention, it was shown that paracrine interactions between human prostate epithelial cells and stromal fibroblasts were disrupted in aging prostate tissues. In particular, specific chemokines that function as inflammatory mediators were secreted at higher levels by aging prostate stromal fibroblasts. Moreover, at levels secreted by older prostate stromal fibroblasts, these chemokines—CXCL1, CXCL5, CXCL6 and CXCL12-stimulated gene transcription, and facilitated the proliferation of both prostate epithelial and stromal fibroblast cells. It was also shown that serum CXCL5 and CXCL12 levels distinguished between men suffering from BPH, prostatitis, and PCa. As such, the present invention demonstrates that levels of specific CXC-type chemokines in patient serum or plasma may, singly or in combination, distinguish between patients suffering from prostatitis, BPH, or cancer, and serve as biomarkers for disease status in the prostate. Accordingly, the present invention provides CXCL1, CXCL5, CXCL6 and/or CXCL12 as biomarkers for prostate disorders. The present invention further provides methods of using biomarkers (e.g., CXCL1, CXCL5, CXCL6 and CXCL12) for monitoring, detecting, diagnosing and treating prostate disorders.

In some embodiments, the present invention provides methods for detecting expression of biomarkers (e.g., CXCL1, CXCL5, CXCL6, and/or CXCL12). In some embodiments, expression is measured directly (e.g., at the nucleic acid level). In some embodiments, expression is detected in tissue samples (e.g., biopsy tumor tissue). In other embodiments, expression is detected in bodily fluids (e.g., including but not limited to, plasma, serum, whole blood, mucus, and urine). The present invention further provides panels and kits for the detection of biomarkers (e.g., CXCL1, CXCL5, CXCL6, and/or CXCL12). In preferred embodiments, the presence of a biomarker (e.g., CXCL1, CXCL5, CXCL6, and/or CXCL12) is used to provide a prognosis to a subject. For example, detection of CXCL5 and/or CXCL12 expression in tissues (e.g., prostatic stromal fibroblasts) above a certain threshold level may be indicative of a prostate disorder (e.g., a cancer cell that is or is not likely to metastasize). In addition, the quantity of CXCL1, CXCL5, CXCL6, and/or CXCL12 expression may be indicative of a transformed cell, a non-cancerous proliferating tissue, a proliferating cancerous tissue, or a cancer likely to metastasize (e.g., experiments conducted during the course of the present invention showed that CXCL12 expression levels as low as 1-5 pM for N15C6 and 50-500 pM for LNCaP prostate epithelial cells stimulated cellular proliferation, and that higher expression levels for such cells were inhibitory to cellular proliferation) (e.g., experiments conducted during the course of the present invention showed that CXCL12 expression levels in N15C6 and LNCaP prostate epithelial cells in the nanomolar range induced prostate epithelial cell motility and invasiveness).

In some embodiments, detection of the presence or absence of a prostate disorder or the characterization of a prostate disorder is accomplished through comparing expression levels of prostate disorder biomarkers (e.g., CXCL1, CXCL5, CXCL6, and/or CXCL12) over a period of time (e.g., between two time points, three time points, ten time points, etc.). In such embodiments, a change in expression level for a prostate disorder biomarker (e.g., CXCL1, CXCL5, CXCL6, and/or CXCL12) over a period of time indicates, for example, an increased risk for developing a prostate disorder, or a change in status for a subject already diagnosed with a prostate disorder (e.g., increased prostate epithelial cell proliferation; increased epithelial cell metastasis). In such embodiments, a change in expression level for a prostate disorder biomarker (e.g., CXCL1, CXCL5, CXCL6, and/or CXCL12) over a period of time indicates, for example, a decreased risk for developing a prostate disorder, or an improved status for a subject already diagnosed with a prostate disorder (e.g., decreased prostate epithelial cell proliferation; decreased epithelial cell metastasis). In some embodiments, comparing expression of prostate disorder biomarkers (e.g., CXCL1, CXCL5, CXCL6, and/or CXCL12) over a period of time may be used to test the efficacy of a treatment (e.g., drugs directed toward treating prostate disorders) and/or may be used to test the efficacy of a new form of treatment (e.g., new drugs directed toward treating prostate disorders).

In some embodiments, detection of the presence or absence of a prostate disorder or the characterization of a prostate disorder is accomplished through comparing expression levels of prostate disorder biomarkers (e.g., CXCL1, CXCL5, CXCL6, and/or CXCL12) to established thresholds. For example, in some embodiments, a subject's expression level for a prostate disorder biomarker detection of the presence or absence of a prostate disorder or the characterization of a prostate disorder is accomplished through comparing expression levels of prostate disorder biomarkers (e.g., CXCL1, CXCL5, CXCL6, and/or CXCL12) compared with established prostate disorder biomarker threshold levels (e.g., established threshold level for low risk for developing prostate disorder; established threshold level for medium risk for developing prostate disorder; established threshold level for high risk for developing prostate disorder; established threshold level for having prostate disorder versus not having prostate disorder; established threshold level for prostate epithelial cell proliferation; established threshold level for prostate epithelial cell metastasis). Established threshold levels may be generated from any number of sources, including but not limited to, groups of men having prostate disorders, groups of men not having prostate disorders, groups of men having prostate cancer, groups of men having prostate cancer and epithelial cell proliferation, groups of men having prostate cancer and prostate epithelial cell metastasis, groups of men having BPH, groups of men under 35 years of age, groups of men under 50 years of age, groups of men under 70 years of age, groups of men over 65 years of age, groups of men having a prostate disorder and a particular form of treatment, etc. Any number of men within a group may be used to generate an established threshold (e.g., 5 men, 10 men, 20, 30, 50, 500, 5000, 10,000, etc.). Threshold levels may be generated with any type or source of bodily sample from a subject (e.g., including but not limited to, plasma, serum, whole blood, mucus, and urine).

The information provided through detection of the biomarkers (e.g., CXCL1, CXCL5, CXCL6, and/or CXCL12) can also be used to direct a course of treatment. For example, if a subject is found to possess expression of a biomarker (e.g., CXCL1, CXCL5, CXCL6, and/or CXCL12) at an amount below a certain threshold (e.g., in the picomolar range for prostate epithelial cells), treatment may be directed to prevent (e.g., reduce, inhibit) cellular proliferation. If, a subject is found to possess expression of biomarker (e.g., CXCL1, CXCL5, CXCL6, and/or CXCL12) at an amount above a threshold (e.g., in the nanomolar range for prostate epithelial cells), treatment may be directed towards prevent (e.g., reduce, inhibit) cellular metastasis (in the case of a cancerous cell). Additionally, other agents (e.g., anti-cancer agents) can be administered to subjects that display elevated levels of the biomarkers (e.g., CXCL1, CXCL5, CXCL6, and/or CXCL12) of the present invention.

The present invention is not limited to the biomarkers described above. Any suitable marker that correlates with a prostate disorder or the progression of a prostate disorder may be utilized in combination with those of the present invention. For example, in some embodiments, biomarkers identified as being up or down-regulated in prostate cancer using the methods of the present invention are further characterized using microarray (e.g., nucleic acid or tissue microarray), immunohistochemistry, Northern blot analysis, siRNA or antisense RNA inhibition, mutation analysis, investigation of expression with clinical outcome, as well as other methods disclosed herein. Examples of suitable markers include, but are not limited to, CXCL chemokines (e.g., CXCL1, CXCL5, CXCL6, CXCL12), CXCL receptors (e.g., CXCR1, CXCR2, CXCR4, CXCR7), and pathway related compounds (e.g., NF-kappaB, ERK ½, ELK-1).

In some preferred embodiments, detection of prostate disorder biomarkers (e.g., including but not limited to, those disclosed herein) is accomplished, for example, by measuring the levels of CXCL chemokines (e.g., CXCL1, CXCL5, CXCL6, CXCL12), CXCL receptors (e.g., CXCR1, CXCR2, CXCR4, CXCR7), and/or pathway related compounds (e.g., NF-kappaB, ERK ½, ELK-1) in cells and tissue (e.g., prostate cells and tissues). For example, in some embodiments, CXCL5 and/or CXCL12 can be monitored using antibodies (e.g., antibodies generated according to methods described below). In some embodiments, detection is performed on cells or tissue after the cells or tissues are removed from the subject. In other embodiments, detection is performed by visualizing the biomarker (e.g., CXCL1, CXCL5, CXCL6, and/or CXCL12) in cells and tissues residing within the subject.

In some embodiments, detection of prostate disorder biomarkers (e.g., CXCL1, CXCL5, CXCL6, CXCL12, CXCR1, CXCR2, CXCR4, CXCR7, NF-kappaB, ELK-1, and ERK ½) is accomplished by measuring the accumulation of corresponding mRNA in a tissue sample (e.g., cancerous tissue). mRNA expression may be measured by any suitable method, including but not limited to, those disclosed below.

In some embodiments, RNA is detected by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, reverse-transcriptase PCR (RT-PCR) is used to detect the expression of RNA (e.g., CXCL1, CXCL5, CXCL6, CXCL12, CXCR1, CXCR2, CXCR4, CXCR7, NF-kappaB, ELK-1 and ERK ½). In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, detection of prostate disorder biomarkers (e.g., CXCL1, CXCL5, CXCL6, CXCL12, CXCR1, CXCR2, CXCR4, CXCR7, NF-kappaB, ELK-1 and ERK ½) is accomplished through protein expression. Protein expression may be detected by any suitable method. In some embodiments, proteins are detected by binding of an antibody specific for the protein. The present invention is not limited to a particular antibody. Any antibody (monoclonal or polyclonal) that specifically detects prostate disorder biomarkers (e.g., CXCL1, CXCL5, CXCL6, CXCL12, CXCR1, CXCR2, CXCR4, CXCR7, NF-kappaB, ELK-1 and ERK ½) may by utilized. In some embodiments, prostate disorder biomarkers (e.g., CXCL1, CXCL5, CXCL6, CXCL12, CXCR1, CXCR2, CXCR4, CXCR7, NF-kappaB, ELK-1 and ERK ½) are detected by immunohistochemistry. In other embodiments, prostate disorder biomarkers (e.g., CXCL1, CXCL5, CXCL6, CXCL12, CXCR1, CXCR2, CXCR4, CXCR7, NF-kappaB, ELK-1 and ERK ½) are detected by their binding to an antibody raised against prostate disorder biomarkers (e.g., CXCL1, CXCL5, CXCL6, CXCL12, CXCR1, CXCR2, CXCR4, CXCR7, NF-kappaB, ELK-1 and ERK ½). In some embodiments, commercial antibodies directed toward prostate disorder biomarkers (e.g., CXCL1, CXCL5, CXCL6, CXCL12, CXCR1, CXCR2, CXCR4, CXCR7, NF-kappaB, ELK-1 and ERK ½) are utilized. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated.

In other embodiments, the immunoassay is as described in U.S. Pat. Nos. 5,599,677 and 5,672,480; each of which is herein incorporated by reference.

In other embodiments, the present invention provides methods for distinguishing between (e.g., detecting, diagnosing) BPH and PCa through measuring CXCL5 and CXCL12 serum levels in subjects presenting with low PSA. Age is a major risk factor for both benign prostatic enlargement (BPH) and prostate cancer (PCA). BPH is one of the most common benign proliferative conditions associated with aging in men and is pathologically characterized by cellular proliferation of the epithelial and stromal elements in the prostate gland (see, e.g., Bierhoff E, et al., Eur. Urol. 1996; 29:345-54; herein incorporated by reference in its entirety). In a survey of 1709 men without cancer recently reported by the Massachusetts Male Aging Study, the frequency of clinical BPH (defined in terms of frequency/difficulty with urinating and evidence of an enlarged/swollen prostate) rose from 8.4% in men 38-49 years of age to 33.5% in men aged 60-70 years ($p<0.001$) (see, e.g., Meigs J B, et al., J Clin Epidemiol. 2001; 54:935-44; herein incorporated by reference in its entirety). Using lower urinary tract symptoms (LUTS) as a surrogate measure for BPH, the Triumph project in the Netherlands reported a 2.7% prevalence rate for BPH in men 45-49 years of age, which increased to 24% in men 80 years of age (see, e.g., Verhamme K, et al., Eur Urol 2002;42: 323-328; herein incorporated by reference in its entirety). For the year 2007, the American Cancer Society estimates that the probability of developing an invasive prostate cancer rises from 0.01% between birth and the fourth decade of life to 2.59% in the fifth decade, 7.03% in the sixth decade, 13.83% in the seventh decade and 17.12% in the eighth decade of life for American men (see, e.g., Jemal A, et al., Cancer Facts and FIGS. 2007. Atlanta, American Cancer Society, 2007. Cleary, age is a major risk factor for the development of both BPH and PCa.

The biological mechanisms responsible for the observed increased age-associated risk for the development of BPH and PCa are poorly understood. The finding that chemokine-type inflammatory mediators are secreted consequent to aging and promote proliferative responses from both non-transformed and transformed prostate epithelial cells suggests that inflammation and inflammatory responses might play a causal role in the development both BPH and PCa (see, e.g., Begley L, et al., Aging Cell. 2005;4:291-8; herein incorporated by reference in its entirety). Indeed, the frequent observation of inflammatory infiltrate in the prostate coincident with BPH or PCa has provoked intense interest in the potential role of inflammatory mediators in the etiology of both diseases. For example, Nickel et al. described studies that examined sectioned transurethral resection of the prostate (TURP) specimens from 80 consecutive patients with a diagnosis of BPH but no history or symptoms of prostatitis (see, e.g., Nickel J C, et al., BJU Int. 1999; 84:976-81; herein incorporated by reference in its entirety). Inflammatory cells were detected in 90% of specimens examined, regardless of whether the patient had been catheterized for urinary retention prior to transurethral resection of the prostate (TURP), or whether bacterial growth resulted from cultured specimens. They concluded that prostatic inflammation is an extremely common histological finding in patients with BPH who have no symptoms of prostatitis, though the clinical significance of asymptomatic chronic prostatitis associated with BPH had yet to be determined (see, e.g., Nickel J C, et al., BJU Int. 1999; 84:976-81; herein incorporated by reference in its entirety). In another study, Gerstenbluth et al. identified pervasive chronic prostatitis in whole mount radical prostatectomy specimens from a series of 40 consecutive patients with clinically localized prostate cancer (see, e.g., Gerstenbluth R E, et al., J. Urol. 2002; 167:2267-70; herein incorporated by reference in its entirety). Although inflammation was associated with both BPH and cancer, it was observed more frequently associated with BPH. They concluded that these findings indirectly supported a potential role for inflammation in the pathogenesis of BPH (see, e.g., Gerstenbluth R E, et al., J. Urol. 2002; 167:2267-70; herein incorporated by reference in its entirety). Data recently reported by Roherborn obtained from examining baseline prostate biopsies in a subgroup of 1197 randomly selected patients in the MTOPS study demonstrated chronic inflammatory infiltrate in 30-60% of men with BPH. Patients with chronic inflammatory infiltrate had larger prostate volumes and demonstrated significantly more clinical progression and acute urinary retention than those who had no inflammation (see, e.g. Roehrborn C G, et al., AUA Meeting 2005, Abstract #1277).

With regard to the role of inflammation in prostate tumorigenesis, De Marzo et al. have identified a type of hyperproliferative lesion in the prostate that is associated with inflammation and is morphologically similar to prostatic atrophy termed proliferative inflammatory atrophy, or PIA (see, e.g., De Marzo A M, et al., Am J. Pathol. 1999; 155:1985-92; herein incorporated by reference in its entirety). This group also showed that high-grade prostatic intraepithelial neoplasia (PIN) is often observed in proximity to PIA, and that morphologic transitions between high-grade PIN and PIA occur frequently within the same acinus/duct. It was concluded that these results are consistent with a model in which the proliferative epithelium in PIA may progress to PIN and/or adenocarcinoma (see, e.g., Putzi M J, et al., Urology 2000; 56: 828-32; Dennis L K, et al., Urology 2002; 60:78-83; each herein incorporated by reference in their entireties).

Epidemiological studies have also noted an increased risk for prostate cancer among men with a history of prostatic inflammation (see, e.g., Dennis L K, et al., Urology 2002; 60:78-83; incorporated herein by reference in its entirety). These studies are suggestive of a link between inflammatory processes and prostate tumorigenesis.

Detection rates for prostate cancer in men demonstrating total serum PSA values greater than 10 ng/ml are typically 70% or higher when combined with findings of abnormal digital rectal exam (DRE) or with histological evidence based on >6 needle biopsy specimens (see, e.g., Luciani L G, et al., Urology 2006; 67:555-8; Inahara M, et al., Urology 2006t; 68:815-9. JM draft of Jun. 21, 2007; each herein incorporated by reference in their entireties). These rates, however, are much lower for men demonstrating total serum PSA (tPSA) values of <10 ng/ml. For example, malignant glands were detected on needle biopsy for ~30% of men whose tPSA values were between 4-10 ng/ml, but tumor detection fell to 21-23% among men with detectable tPSA values of <4 ng/ml (see, e.g., Kravchick S, et al., Urology 2005; 66:542-6; Pelzer A E, et al., Urology 2005; 66:1029-33; Gilbert S M, et al., Urology 2005; 65:549-53; each herein incorporated by reference in their entireties). This suggests that factors other than cancer may contribute to the accumulation of PSA in the serum. Indeed, elevated serum tPSA values correlate directly with histologic evidence of inflammation on needle biopsy in patients asymptomatic for prostatitis (see, e.g., Simardi L H, et al., Urology 2004; 64:1098-101; herein incorporated by reference in its entirety). Another study evaluating patients enrolled in the Chronic Prostatitis Cohort Study and age-matched controls found that total and other forms of serum PSA was elevated in men diagnosed with chronic prostatitis/chronic pelvic pain syndrome (see, e.g., Nadler R B, et al., Urology 2006; 67:337-42; herein incorporated by reference in its entirety). Importantly, this study determined that total and other forms of serum PSA alone did not demonstrate sufficient sensitivity and specificity for use as diagnostic markers for chronic prostatitis/chronic pelvic pain syndrome (see, e.g., Nadler R B, et al., Urology 2006; 67:337-42; herein incorporated by reference in its entirety). Lastly, increased prostate volume may contribute to elevated tPSA values in the absence of cancer. A recent study showed that a smaller prostate volume is the strongest predictor of cancer detection in men exhibiting tPSA levels in the 2.0 to 9.0 ng/ml range, suggesting that tPSA is less useful for the prediction of cancer in men with concurrent BPH (see, e.g., Al-Azab R, et al., Urology 2007; 69:103-7; incorporated herein by reference in its entirety). Several studies have shown that serum tPSA values increase concomitantly with patient age in parallel with increased incidence of BPH (see, e.g., Roehrborn C G, et al., Urology 199953:581-9; Wright E J, et al., J. Urol. 2002; 167:2484-7; discussion 2487-8; Berger A P, et al., Urology 2003; 62:840-4; Berger A P, et al., Urology 2007; 69:134-8; Pinsky P F, et al., Urology 2006; 68:352-6; each herein incorporated by reference in their entireties).

Taken together, these studies indicate that additional serum biomarkers would be valuable to distinguish between prostatic diseases in men exhibiting serum PSA values of <10 ng/ml. The identification of elevated levels of CXC-type chemokines in culture media conditioned by aging normal, as well as carcinoma-associated, stromal fibroblasts, links these chemokines with the major types of disease found in the human prostate, e.g., BPH, PCa, and prostatitis. Based on these findings, studies were conducted to test the hypothesis that the serum concentrations of specific CXC-type chemokines may provide objective criteria to facilitate a differential diagnosis of BPH or PCa in men with low (<10 ng/ml) serum PSA.

In experiments conducted during the course of development of embodiments for the present invention, total serum CXCL12 levels were shown to be significantly higher for men who were biopsy-positive compared to those who were biopsy-negative for cancer and histological prostatitis ($p=0.050$), and were reduced or ablated in 5/7 (71%) men after removal of the cancerous prostate. Among men who were biopsy-negative for prostate cancer, total serum CXCL5 levels were inversely associated with prostate volume and were significantly higher in men with concomitant BPH and histological prostatitis compared to those without evidence of prostatic disease ($p<0.003$). As such, serum CXCL5 and CXCL12 levels can differentially distinguish between BPH and PCa among patients presenting with low (<10 ng/ml) serum prostate specific antigen (PSA) and may potentially be used to facilitate decisions to perform diagnostic needle biopsy in this patient population. Accordingly, the present invention provides methods for distinguishing (e.g., diagnosing, detecting) between BPH and PCa through measuring CXCL5 and CXCL12 serum levels in subjects presenting with low PSA. Accordingly, the present invention provides methods for diagnosing BPH and PCa through measuring CXCL5 and CXCL12 serum levels in subjects presenting with low PSA, such that PCa is associated with higher CXCL12 serum levels than CXCL5 serum levels, and BPH is associated with higher CXCL5 serum levels than CXCL12 serum levels.

III. In vivo Imaging

In some embodiments, in vivo imaging techniques are used to visualize and quantify the expression of prostate disorder biomarkers (e.g., CXCL1, CXCL5, CXCL6, CXCL12, CXCR1, CXCR2, CXCR4, CXCR7, NF-kappaB, ELK-1 and ERK ½) in an animal (e.g., a human or non-human mammal). For example, in some embodiments, prostate disorder biomarker mRNA or protein is labeled using a labeled antibody specific for the biomarker. Specifically bound and labeled antibodies can be quantified and detected in an individual using any in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the biomarkers of the present invention are described below.

The in vivo imaging methods of the present invention are useful in the research use and the diagnosis of prostate disorders (e.g., PCa, BPH) in cells that contain the biomarkers of the present invention (e.g., localized or metastatic cancerous cells or tissue). In vivo imaging is used to quantify and visualize the presence of a biomarker indicative of a prostate disorder. Such techniques allow for diagnosis without the use of a biopsy. In some embodiments, the in vivo imaging methods of the present invention are useful for providing prognoses to patients (e.g., cancer patients, patients suffering from BPH). For example, the presence of prostate disorder biomarkers (e.g., CXCL1, CXCL5, CXCL6, CXCL12, CXCR1, CXCR2, CXCR4, CXCR7, NF-kappaB, ELK-1 and ERK ½) expressed at an amount above a certain threshold may be indicative of a cancer likely or not likely to respond to certain treatments. The in vivo imaging methods of the present invention can further be used to detect replicating, neoplastic cells in other parts of the body (e.g., in lymph nodes).

In some embodiments, reagents (e.g., antibodies) specific for the biomarkers of the present invention are fluorescently labeled. The labeled antibodies can be introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 (1990) have described an optimized antibody-chelator for the radioimmunoscintographic imaging of tumors using Indium-111 as the label. Griffin et al., (J Clin One 9:631-640 (1991)) have described the use of this agent in detecting tumors in patients suspected of having recurrent colorectal cancer. The use of similar agents with paramagnetic ions as labels for magnetic resonance imaging is known in the art (See, e.g., Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies. In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific biomarker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a biomarker of the present invention). When active, it leads to a reaction that emits light. A CCD camera and software can be used to capture the image and analyze it.

IV. Antibodies

The present invention provides isolated antibodies. In preferred embodiments, the present invention provides monoclonal antibodies that specifically bind to the prostate disorder biomarkers (e.g., CXCL1, CXCL5, CXCL6, CXCL12, CXCR1, CXCR2, CXCR4, CXCR7, NF-kappaB, ELK-1 and ERK ½). Examples include, but are not limited to, monoclonal antibody against CXCR4 (Abcam #Ab10403) and/or CXCR7 (Abcam #Ab12870, Abcam #Ab12871, Abcam #38089) to block interactions with CXCL12, or monoclonal antibody against CXCR2 (Abcam #Ab24963) to block interactions with CXCL5. These antibodies, and others, find use in the diagnostic and therapeutic methods described herein.

An antibody against a biomarker of the present invention may be any monoclonal or polyclonal antibody, as long as it can recognize the biomarker. Antibodies can be produced by using a biomarker of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, biomarkers, as such, or together with a suitable carrier or diluent is administered to an animal (e.g., a mammal) under conditions that permit the production of antibodies. For enhancing the antibody production capability, complete or incomplete Freund's adjuvant may be administered. Normally, the biomarker is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a biomarker of the present invention). For example, a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a biomarker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a biomarker of the present invention (further including a gene having a nucleotide sequence partly altered) can be used as the immunogen. Further, fragments of the biomarker protein may be used. Fragments may be obtained by any method including, but not limited to expressing a fragment of the gene, enzymatic processing of the protein, chemical synthesis, and the like.

V. Therapeutics

In preferred embodiments, the present invention provides a method of treating or researching (e.g., inhibiting cellular proliferation, preventing metastasis, etc.) prostate disorders comprising altering (e.g., reducing, inhibiting) CXCL1, CXCL5, CXCL6, and/or CXCL12 expression and/or activity. In some embodiments, altering CXCL1, CXCL5, CXCL6, and/or CXCL12 expression and/or activity comprises providing to the cell a composition comprising a CXCL1, CXCL5, CXCL6, and/or CXCL12 inhibitor. In some embodiments, altering CXCL1, CXCL5, CXCL6, and/or CXCL12 activity comprises altering (e.g., reducing, inhibiting) the receptors for CXCL1, CXCL5, CXCL6, and/or CXCL12 (CXCR1, CXCR2, CXCR4, and CXCR7 respectively). In some embodiments, altering CXCL1, CXCL5, CXCL6, and/or CXCL12 activity comprises altering (e.g., reducing, inhibiting) components of the pathways associated with CXCL1, CXCL5, CXCL6, and/or CXCL12 (e.g., NF-kappaB, ERK ½, ELK-1). In some embodiments, altering CXCL1, CXCL5, CXCL6, and/or CXCL12 activity comprises altering (e.g., reducing, inhibiting) genes upregulated (e.g., EGFR, CD44, ANKRD12, SSBP1, CCNT1, JMJD1C, HNRPD, GOPC, STRAP, DYX1C1) or downregulated (e.g., CDH1, CTNNB1, CPSF1, EXOSC6, ITGB4, LOXL2, SORBS3, GSR, RANGAP1, NUMA1, RBM14, BMP1, ERBB2, MAPRE3, DOCK9, ARPC4, MARCKS) in response to CXC chemokine (e.g., CXCL12, CXCL5) expression. In some embodiments, altering CXCL1, CXCL5, CXCL6, and/or CXCL12 activity involves a combination of several approaches, including but not limited to, altering CXCL1, CXCL5, CXCL6, and/or CXCL12 activity, altering CXCL1, CXCL5, CXCL6, and/or CXCL12 associated pathways, altering transcription of upregulated and/or downregulated in response to CXCL1, CXCL5, CXCL6, and/or CXCL12 expression, and altering CXCL1, CXCL5, CXCL6, and/or CXCL12 receptors.

The present invention is not limited by the type of inhibitor used to inhibit CXCL1, CXCL5, CXCL6, and/or CXCL12 activity and/or expression for treating a prostate disorder in a cell. Indeed, any compound, pharmaceutical, small molecule or agent (e.g., antibody, protein or portion thereof) that can alter CXCL1, CXCL5, CXCL6, and/or CXCL12 expression and/or activity is contemplated to be useful in the methods of the present invention. In some embodiments, inhibitors used in altering CXCL1, CXCL5, CXCL6, and/or CXCL12 activity and/or expression include, but are not limited to, anti-human ENA-78 (see, e.g., Halloran, M. M. et al., 1999, J. Immunol. 162:7492-7500; incorporated herein by reference in its entirety), the NF-kappaB inhibitor BAY 11-7085 (see, e.g., Shen & Lentsch, 2004, Am. J. Cell. Physiol. 286:C840; incorporated herein by reference in its entirety), and the CXCL12 inhibitor tannic acid (see, e.g., Chen, X. et al., 2003, Clinical Cancer Research 9:3115-3123; incorporated herein by reference in its entirety).

In some embodiments, altering CXCL1, CXCL5, CXCL6, and/or CXCL12 expression and/or activity comprises providing to a cell CXCL1, CXCL5, CXCL6, and/or CXCL12 specific siRNAs. In some embodiments, altering CXCL1, CXCL5, CXCL6, and/or CXCL12 expression and/or activity comprises providing to a cell siRNAs specific for components of pathways associated with CXCL1, CXCL5, CXCL6, and/or CXCL12 activity. In some embodiments, altering CXCL1, CXCL5, CXCL6, and/or CXCL12 expression and/or activity comprises providing to a cell siRNAs specific for the receptors for CXCL1 (CXCR1), CXCL5 (CXCR2) and/or CXCL12 (CXCR4 and CXCR7). The present invention is not limited by the siRNA used. For example, in some embodiments, the present invention provides siRNAs of about 18-25 nucleotides long, 19-23 nucleotides long, or even more preferably 20-22 nucleotides long. The siRNAs may contain from about two to four unpaired nucleotides at the 3' end of each strand. In preferred embodiments, at least one strand of the duplex or double-stranded region of a siRNA is substantially homologous to or substantially complementary to a target RNA molecule (e.g., CXCL5 or CXCL12). The present invention is not limited by the target RNA molecule/sequence. Indeed, a variety of target sequences are contemplated to be useful in the present invention including, but not limited to, 18-25 nucleotide stretches of the CXCL5 and/or CXCL12 mRNA sequence (see, e.g., NCBI Accession No. NM_002994 for CXCL5, and NCBI Accession No. NM_199168), or associated receptors CXCR2 and/or CXCR4.

In some embodiments, altering CXCL1, CXCL5, CXCL6, and/or CXCL12 expression and/or activity comprises providing to the cell an antibody specific for CXCL1, CXCL5, CXCL6, and/or CXCL12, an antibody specific for CXCL1, CXCL5, CXCL6, and/or CXCL12 associated pathways, and/or an antibody specific for the CXCR1 receptor (CXCR1), CXCL5 receptor (CXCR2) and/or the CXCL12 receptor (CXCR4 and CXCR7). In some embodiments, the antibody reduces activity of CXCL1, CXCL5, CXCL6, and/or CXCL12 in the cell. In some embodiments, altering CXCL1, CXCL5, CXCL6, and/or CXCL12 expression and/or activity in the cell sensitizes the cell to an additional form of therapeutic treatment (e.g., chemotherapy). In some embodiments, sensitizing the cell to additional forms of therapeutic treatment permits the cell to undergo treatment-induced cell death. In some embodiments, altering CXCL1, CXCL5, CXCL6, and/or CXCL12 expression and/or activity inhibits symptoms of a prostate disorder (e.g., BPH, prostatitis, PCa).

In some embodiments, the present invention also provides a method of treating a subject with BPH comprising providing a composition comprising an inhibitor of CXCL1, CXCL5, CXCL6, and/or CXCL12; and administering the composition to the subject under conditions such that CXCL1, CXCL5, CXCL6, and/or CXCL12 expression and/or activity is altered. In some embodiments, the composition comprising an inhibitor of CXCL1, CXCL5, CXCL6, and/or CXCL12 is co-administered with an agent configured to treat BPH. The present invention is not limited by type of anti-BPH agent co-administered. Indeed, a variety of anti-BPH agents are contemplated to be useful in the present invention including, but not limited to, Alpha-adrenergic blockers (e.g., Phenoxybenzamine (Dibenzyline), Prazosin (Minipress), Alfuzosin (UroXatral), Indoramin, Terazosin (Hytrin), Doxazosin (Cardura), Tamsulosin (Flomax)), and 5-Alpha-reductase inhibitors (e.g., Finasteride (Proscar), Dutasteride (Avodart)). In some embodiments, the present invention also provides a method of treating a subject with prostatitis comprising providing a composition comprising an inhibitor of CXCL1, CXCL5, CXCL6, and/or CXCL12; and administering the composition to the subject under conditions such that CXCL1, CXCL5, CXCL6, and/or CXCL12 expression and/or activity is altered. In some embodiments, the composition comprising an inhibitor of CXCL1, CXCL5, CXCL6, and/or CXCL12 is co-administered with an agent configured to treat prostatitis. The present invention is not limited by type of anti-prostatitis agent co-administered. Indeed, a variety of anti-prostatitis agents are contemplated to be useful in the present invention including, but not limited to, an antibiotic (e.g., Ofloxacin (Floxin), Ciprofloxacin (Cipro, Cipro XR), Levofloxacin (Levaquin), Gatifloxacin (Tequin), Ceftriaxone (Rocephin), Doxycycline (Bio-Tab, Doryx, Vibramycin)), Alpha-adrenergic agonists (e.g., Prazosin (Minipress)), benzodiazepines (e.g., Diazepam (Valium)).

In some embodiments, the present invention also provides a method of treating a subject with prostate cancer comprising providing a composition comprising an inhibitor of CXCL1, CXCL5, CXCL6, and/or CXCL12; and administering the composition to the subject under conditions such that CXCL1, CXCL5, CXCL6, and/or CXCL12 expression and/or activity is altered. In some embodiments, the composition comprising an inhibitor of CXCL1, CXCL5, CXCL6, and/or CXCL12 is co-administered with an anti-cancer agent (e.g., chemotherapeutic). The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl)retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hypertrophy therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-Cl-2'deoxyadenosine; Fludarabine-$PO_4$; mitoxantrone; mitozolomide; Pentostatin; and Tomudex.

One particularly preferred class of anticancer agents are taxanes (e.g., paclitaxel and docetaxel). Another important category of anticancer agent is annonaceous acetogenin.

Other cancer therapies include hormonal manipulation. In some embodiments, the anti-cancer agent is tamoxifen or the aromatase inhibitor arimidex (i.e., anastrozole).

In some embodiments, the present invention provides methods and compositions suitable for therapy (e.g., drug, prodrug, pharmaceutical, or gene therapy) to alter CXCL1, CXCL5, CXCL6, and/or CXCL12 gene expression, production, or function (e.g., to inhibit CXCL1, CXCL5, CXCL6, and/or CXCL12 expression and/or activity).

In some embodiments, the present invention provides compositions comprising expression cassettes comprising a nucleic acid encoding an inhibitor of CXCL1, CXCL5, CXCL6, and/or CXCL12 (e.g., siRNAs, antibodies, peptides and the like), and vectors comprising such expression cassettes. The methods described below are generally applicable across many species. Any of the vectors and delivery methods disclosed herein can be used for modulation of CXCL1, CXCL5, CXCL6, and/or CXCL12 activity (e.g., in a therapeutic setting). As disclosed herein, the therapeutic methods of the invention are optimally achieved by targeting the therapy to the affected cells. Means for targeting delivery of various treatments, such as radiation or chemotherapy, are described below. However, in another embodiment, a CXCL1, CXCL5, CXCL6, and/or CXCL12 inhibitor can be targeted to cells, e.g., using vectors described herein in combination with well-known targeting techniques, for expression of CXCL1, CXCL5, CXCL6, and/or CXCL12 modulators.

Furthermore, any of the therapies described herein can be tested and developed in animal models. Thus, the therapeutic aspects of the invention also provide assays for CXCL1, CXCL5, CXCL6, and/or CXCL12 function.

In some embodiments, viral vectors are used to introduce CXCL1, CXCL5, CXCL6, and/or CXCL12 inhibitors (e.g., siRNAs, proteins or fragments thereof, etc.) to cells. The present invention further provides a method for altering responsiveness of a prostate cell (e.g., a cancerous prostate cell) to treatment comprising altering the levels of CXCL1, CXCL5, CXCL6, and/or CXCL12 in the cell (e.g., through inhibiting CXCL1, CXCL5, CXCL6, and/or CXCL12 expression using RNAi). The art knows well multiple methods of altering the level of expression of a gene or protein in a cell (e.g., ectopic or heterologous expression of a gene). The following are provided as exemplary methods of introducing CXCL1, CXCL5, CXCL6, and/or CXCL12 inhibitors, and the invention is not limited to any particular method.

In some embodiments, the present invention provides a method of treating prostate cancer cells comprising altering responsiveness of the prostate cancer cells to treatment comprising making the prostate cancer cells either more or less responsive (e.g., sensitive) to treatment. In some embodiments, making the prostate cancer cells more or less responsive (e.g., sensitive) to treatment comprises altering the level of CXCL1, CXCL5, CXCL6, and/or CXCL12 expression and/or activity in the target cell. The present invention further provides a method of customizing prostate cancer cells for treatment by altering CXCL1, CXCL5, CXCL6, and/or CXCL12 expression and/or activity in the prostate cancer cells. In some embodiments, altering the level of CXCL1, CXCL5, CXCL6, and/or CXCL12 in the target cell comprises introducing siRNA (e.g., that inhibit CXCL1, CXCL5, CXCL6, and/or CXCL12 expression) or antibodies (e.g., that inhibit CXCL1, CXCL5, CXCL6, and/or CXCL12 activity) to the target cell.

In some embodiments, the present invention targets the expression of CXCL1, CXCL5, CXCL6, and/or CXCL12, receptors, and/or pathway related components (e.g., CXCR1, CXCR2, CXCR4, CXCR7, NF-kappaB, ERK ½, ELK-1) (e.g., for treating prostate disorders such as PCa and BPH). For example, in some embodiments, the present invention employs compositions comprising oligomeric antisense compounds, particularly oligonucleotides, for use in modulating the function of nucleic acid molecules encoding CXCL1, CXCL5, CXCL6, and/or CXCL12, ultimately modulating the amount of CXCL1, CXCL5, CXCL6, and/or CXCL12 expressed. This is accomplished by providing antisense compounds that specifically hybridize with one or more nucleic acids encoding CXCL1, CXCL5, CXCL6, and/or CXCL12. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of CXCL1, CXCL5, CXCL6, and/or CXCL12. In the context of the present invention, "modulation" means either an increase (stimulation) or a decrease (inhibition) in the expression of a gene. For example, expression may be inhibited to potentially prevent tumor growth, inhibition of complement mediated lysis, angiogenesis and proliferation.

Introduction of molecules carrying genetic information into cells is achieved by any of various methods including, but not limited to, directed injection of naked DNA constructs, bombardment with gold particles loaded with the constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is incorporated herein by reference in their entireties.

Vectors may be administered to subject in a variety of ways. For example, in some embodiments of the present invention, vectors are administered into prostate cancer cells or tissue using direct injection. In other embodiments, administration is via the blood or lymphatic circulation of a patient with prostate cancer (See e.g., PCT publication 99/02685 incorporated herein by reference in its entirety). Exemplary dose levels of adenoviral vector are preferably $10^8$ to $10^{11}$ vector particles added to the perfusate.

In some embodiments, the present invention provides antibodies (e.g., full length or portions thereof, the generation of which is described herein) that target CXCL1, CXCL5, CXCL6, and/or CXCL12 expressing prostate cancer cells (e.g., tumors). In preferred embodiments, the antibodies used for treating prostate cancer are humanized antibodies. In preferred embodiments, the antibody alters (e.g., inhibits) CXCL1, CXCL5, CXCL6, and/or CXCL12 activity or function.

In some embodiments, the therapeutic methods (e.g., application of siRNAs, application of antibodies, gene therapies, etc.) are provided so as to alter varying ranges of CXCL5 and/or CXCL12 activity depending on the desired type of treatment effect (e.g., altering cellular proliferation, altering cellular matastasis). Experiments conducted during the course of the present invention demonstrated that older fibroblasts expressed and secreted higher levels of the CXCL5 and/or CXCL12 compared with younger fibroblasts, and the CXCL5 and/or CXCL12 protein was mechanistically associated with enhanced epithelial cell proliferation. In addition, experiments conducted during the course of the present invention indicated that varying levels of the chemokine CXCL5 and/or CXCL12 are expressed in prostate cancer cells depending upon the status of the cells. For example, prostate cancer cells undergoing metastasis express higher levels of the chemokine CXCL5 and/or CXCL12 (e.g., in the nanomolar range) than prostate cancer cells undergoing proliferation (e.g., in the picomolar range). In particular, experiments conducted during the course of the present invention showed that CXCL12 expression levels as low as 1-5 pM for N15C6 and 50-500 pM for LNCaP prostate epithelial cells stimulated cellular proliferation, and that higher expression levels for such cells were inhibitory to cellular proliferation. In addition, experiments conducted during the course of the present invention showed that CXCL12 expression levels in the nanomolar range induced prostate epithelial cell motility and invasiveness. As such, in some embodiments, the methods are directed to alter (e.g., reduce, inhibit) CXCL5 and/or CXCL12 activity at approximately a picomolar concentration for altering cellular proliferation, and approximately a nanomolar concentration for altering cellular matastasis.

VI. Pharmaceutical Compositions

The present invention further provides pharmaceutical compositions (e.g., comprising an inhibitor of CXCL1, CXCL5, CXCL6, and/or CXCL12 expression and/or activity described herein). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams.

Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) one or more inhibitors of CXCL1, CXCL5, CXCL6, and/or CXCL12 expression and/or activity (e.g., antisense compounds, antibodies, etc.) and (b) one or more other anti-prostate disorder agents (e.g., anti-BPH agents, anti-cancer agents). Examples of such anti-BPH and anti-cancer agents are described above. In some embodiments, two or more combined anti-prostate disorder agents (e.g., an inhibitor of CXCL1, CXCL5, CXCL6, and/or CXCL12 and another anti-cancer agent) may be used together or sequentially.

Dosing may be dependent on severity and responsiveness of the disease state (e.g., stage of prostate cancer) to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the treatment (e.g., CXCL1, CXCL5, CXCL6, and/or CXCL12 siRNA or antibody) is administered in maintenance doses, ranging from 0.01 μg to 100 g per kg of body weight, once or more daily, to once every 20 years.

In some embodiments, the pharmaceutical compositions are provided so as to alter varying ranges of CXCL5 and/or CXCL12 activity depending on the desired type of treatment effect (e.g., altering cellular proliferation, altering cellular matastasis). For example, experiments conducted during the course of the present invention indicated that varying levels of the chemokine CXCL5 and/or CXCL12 are expressed in prostate cancer cells depending upon the status of the cells. For example, prostate cancer cells undergoing metastasis express higher levels of the chemokine CXCL5 and/or CXCL12 (e.g., in the nanomolar range) than prostate cancer cells undergoing proliferation (e.g., in the picomolar range). As such, in some embodiments, the pharmaceutical compositions are directed to alter (e.g., reduce, inhibit) CXCL5 and/or CXCL12 activity at approximately a picomolar concentration for altering cellular proliferation, and approximately a nanomolar concentration for altering cellular matastasis.

VII. Drug Screening

In some embodiments, the present invention provides drug screening assays (e.g., to screen for new drugs for treating prostate disorders). The screening methods of the present invention utilize prostate disorder biomarkers (e.g., CXCL1, CXCL5, CXCL6, CXCL12, CXCR1, CXCR2, CXCR4, CXCR7, NF-kappaB, ELK-1, and ERK ½) identified using the methods of the present invention. For example, in some embodiments, the present invention provides methods of screening for compounds that alter (e.g., increase or decrease), directly or indirectly, the presence of prostate disorder biomarkers (e.g., CXCL1, CXCL5, CXCL6, CXCL12, CXCR1, CXCR2, CXCR4, CXCR7, NF-kappaB, ELK-1, and ERK ½). In some embodiments, candidate compounds are antisense agents (e.g., siRNAs, oligonucleotides, etc.) directed against CXCL1, CXCL5, CXCL6, and/or CXCL12, receptors for CXCL1 (CXCR1), CXCL5 (CXCR2) and/or CXCL12 (CXCR4 and CXCR7), or pathways associated with CXCL1, CXCL5, CXCL6, and/or CXCL12 (NF-kappaB, ERK ½). In other embodiments, candidate compounds are antibodies that specifically bind to a prostate disorder biomarker (e.g., CXCL1, CXCL5, CXCL6, CXCL12, CXCR1, CXCR2, CXCR4, CXCR7, NF-kappaB, ELK-1, and ERK ½) of the present invention. Also contemplated to be discoverable using the compositions and methods of the present invention are proteins, peptides, peptide mimetics, small molecules and other agents that can be used to treat prostate cancer.

In one screening method, candidate compounds are evaluated for their ability to alter biomarker presence, activity or expression by contacting a compound with a cell (e.g., a prostate cancer cell expressing a biomarker or capable of generating a biomarker) and then assaying for the effect of the candidate compounds on the presence or expression of a prostate disorder biomarker (e.g., CXCL1, CXCL5, CXCL6, CXCL12, CXCR1, CXCR2, CXCR4, CXCR7, NF-kappaB, ELK-1, and ERK ½). In some embodiments, the effect of candidate compounds on expression or presence of a prostate disorder biomarker (e.g., CXCL1, CXCL5, CXCL6, CXCL12, CXCR1, CXCR2, CXCR4, CXCR7, NF-kappaB, ELK-1, and ERK ½) is assayed for by detecting the level of biomarker present within the cell. In other embodiments, the effect of candidate compounds on expression or presence of a biomarker is assayed for by detecting the level of prostate disorder biomarker (e.g., CXCL1, CXCL5, CXCL6, CXCL12, CXCR1, CXCR2, CXCR4, CXCR7, NF-kappaB, ELK-1, and ERK ½) present in the extracellular matrix.

In other embodiments, the effect of candidate compounds on expression or presence of biomarkers is assayed by measuring the level of polypeptide encoded by the biomarkers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) that bind to proteins that generate biomarkers of the present invention, have an inhibitory (or stimulatory) effect on, for example, biomarker expression and/or biomarker activity, or have a stimulatory or inhibitory effect on, for example, the expression or activity of a biomarker substrate. Compounds thus identified can be used to modulate the activity of target gene products either directly or indirectly in a therapeutic protocol, to elaborate the biological function of the target gene product, or to identify compounds that disrupt normal target gene interactions. Compounds that inhibit or enhance the activity, expression or presence of biomarkers find use in the treatment of prostate disorders (e.g., PIN, BPH, PCa, etc.).

In one embodiment, the invention provides assays for screening candidate or test compounds that are substrates of a biomarker. In another embodiment, the invention provides assays for screening candidate or test compounds that bind to or modulate the activity of a biomarker.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364: 555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

This invention further pertains to novel agents identified by the above-described screening assays. Accordingly, it is within the scope of this invention to further use an agent identified as described herein (e.g., a biomarker modulating agent, an antisense marker nucleic acid molecule, a siRNA molecule, a biomarker specific antibody, or a biomarker- binding substrate) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

VIII. Kits

In yet other embodiments, the present invention provides kits for the detection, characterization, and/or treatment of prostate disorders (e.g., PCa, BPH). In some embodiments, the kits contain antibodies specific for prostate disorder biomarkers (e.g., CXCL1, CXCL5, CXCL6, CXCL12, CXCR1, CXCR2, CXCR4, CXCR7, NF-kappaB, ELK-1, and ERK ½). In some embodiments, the kits further contain detection reagents and buffers. In other embodiments, the kits contain reagents specific for the detection of nucleic acids (e.g., DNA, RNA, mRNA or cDNA, oligonucleotide probes or primers). In preferred embodiments, the kits contain all of the components necessary and/or sufficient to perform a detection assay, including all controls, directions for performing assays, and any necessary software for analysis and presentation of results.

EXPERIMENTAL

The following examples are provided in order to demonstrate and further illustrate certain preferred embodiments and aspects of the present invention and are not to be construed as limiting the scope thereof.

EXAMPLE I

This example describes the materials and methods used for Examples II-VI.

Establishment of cell cultures. Normal prostate tissue samples were obtained aseptically from patients undergoing radical prostatectomy or cystoprostatectomy after cancer diagnosis. Tissue was taken exclusively from the transitional zone of the prostate surrounding the urethra to facilitate the isolation of fibroblasts associated with benign prostatic hypertrophy (BPH). A small slice of the tissue piece (25%) was fixed in 10% formalin for immunohistochemical examination. The remaining tissue was minced into pieces of <1 mm in size, digested overnight in 1 mg mL$^{-1}$ collagenase III (Worthington Biochemicals, Lakewood, N.J., USA) at 37° C. with gentle shaking, spun down, resuspended and plated in 5% HIE media [Ham's F12 (Mediatech Inc., Herndon, Va., USA) with 5% FBS (Invitrogen Life Technologies Inc., Carlsbad, Calif., USA), 5 µg mL$^{-1}$ insulin, 10 ng mL$^{-1}$ EGF, 1 µg mL$^{-1}$ hydrocortisone (Sigma Chemical Co., St. Louis, Mo., USA). Subcultured fibroblast cell populations were assessed by immunohistochemistry using monoclonal antibodies to vimentin or alpha-actin (Sigma Aldrich, St. Louis, Mo., USA) to distinguish stromal fibroblastic cells from smooth muscle cells, respectively. The fibroblast cell populations used in these studies were stained uniformly for vimentin but not alpha-actin and were maintained in 5% HIE.

The N15C6 cell line was developed as described previously (Macoska J A, et al., (2004) Cancer Genet. Cytogenet. 154, 36-43; Begley L, 2006 Genes Chromosomes Cancer. 45(2):136-46; incorporated herein by reference in their entireties). For conditioned media experiments, N15C6 cells were grown either in defined serum-free HIE media supplemented to 5 mM ethanolamine (Sigma-Aldrich), 10 mM HEPES (Sigma-Aldrich), 5 µg µL$^{-1}$ transferrin (Sigma-Aldrich), 10 µM 3,3',5-triiodo-L-thyronine (Sigma-Aldrich), 50

μM sodium selenite (Sigma-Aldrich), 0.1% BSA (JRH Biosciences Lenexa, Kans., USA), 0.05 mg mL−1 gentamycin (Gibco, Carlsbad, Calif., USA), and 0.5 μg mL−1 fungizone (Cambrex Bioscience, Walkersville, Md., USA), or in defined serum-free HIE conditioned media produced through the incubation of fibroblast cell populations in supplemented serum-free HIE media over a 48-h period. Conditioned media were harvested from all fibroblast cell populations at passages 1-3 with the exception of no. 2396 (passage 4), no. 3294 and no. 10063 (passage 5), and no. 11033 and no. 3382 (passage 11).

Proliferation assays. Cellular proliferation was assessed after plating cells at 50 000 cell/well in triplicate in six-well plates and counting cells after 24 and 96 h of incubation in complete media, serum-free media or serum-free prostate stromal fibroblast conditioned media, as described previously (Macoska J A, et al., (2004) Cancer Genet. Cytogenet. 154, 36-43; incorporated herein by reference in its entirety). Averages and standard deviations of cell number were calculated for each time point under each media condition. To assess the effects of exogenous CXCL12 on cellular proliferation, recombinant human SDF1 alpha/CXCL12 (R & D Systems, 350-NS) was added at the desired concentration in 1 mL SF HIE (or 1 mL SF HIE alone for control) to each well. The cells were counted at 24 and 96 h growth and re-fed at 48 and 72 h growth. Cell counts were normalized to 50 000 cells at 24 h to account for any plating discrepancies.

Affymetrix U133A GeneChip data acquisition. RNA was purified from trypsinized cultured cells by homogenization in Trizol (Invitrogen, Carlsbad, Calif., USA) and additional processing using the RNeasy (QIAGEN, Valencia, Calif., USA) cleanup procedure. Ten micrograms of RNA obtained from tissues or cell line was used to obtain labeled cRNA following the Affymetrix standard protocol. Expression intensity values for each gene were estimated using a method called Robust Multi-array average (RMA) using tools available through Bioconductor (www, followed by, bioconductor.org). GeneChip gene expression values were normalized using a quantile normalization procedure.

Quantitative real-time PCR. All quantitative real-time assays were conducted with an Applied Biosystems 7900HT instrument and reagents. One microgram of RNA was reverse transcribed by use of Superscript III reverse transcriptase (Invitrogen, Carlsbad, Calif., USA). The resulting cDNA was diluted 1:100. Real-time PCR was performed by use of Assays on Demand (Applied BioSystems, Foster City, Calif., USA) according to the manufacturer's instructions, except that Real Time Ready with Rox passive dye (QBioGene, Carlsbad, Calif., USA) was used in place of TaqMan Universal PCR Master Mix. Reactions were performed in triplicate, including no-template controls and an endogenous control probe to assess template concentration (ribosomal protein, large, PO). Cycle numbers to threshold were calculated by subtracting averaged control from averaged experimental values, and Fold Gene Expression was calculated by raising these values to the log 2. FAM conjugated, gene-specific assays were Hs00171022_ml for CXCL12, and Hs99999902_ml for the control, RPLPO.

ELISA assays Fibroblasts were grown in 0.01% BSA defined HIE for 3 days. Fibroblast-conditioned media were collected, serially concentrated using Centriplus Centrifugal Filters (Millipore, Billerica, Mass., USA) with a 3 kDa molecular weight cutoff, and assessed using the CXCL12/SDF1-alpha ELISA system (R & D Systems). All reactions were performed in duplicate and the resulting values averaged.

Western blot analysis Cells were lysed, proteins resolved by electrophoresis and electroblotting was carried out as described previously (Chaib H, et al., (2001) Cancer Res. 61, 2390-2394; incorporated herein by reference in its entirety). Proteins were detected using antibodies against phospho-ERK½ (Cell Signaling no. 9101), total ERK½ (Cell Signaling, no. 9102), CXCR4 (Abcam no. ab2074), CXCR7 (Abcam #Ab12870, Abcam #Ab12871, Abcam #38089), phospho-p65 (Rockland no. 100-401-264), total p65 (Rockland no. 100-4165), or beta-actin (Santa Cruz no. sc-1615), in conjunction with an ECL detection system.

Construction of tissue microarray (TMA) and immunohistochemistry A TMA was constructed from 31 radical prostatectomy specimens to represent benign prostate tissues [number of cores (N)=24]; benign prostatic hypertrophy epithelial tissues (BPH-E) (N=65); benign prostatic hypertrophy stromal tissue (BPH-S) (N=102) and prostate cancer (N=77). Antigen retrieval was performed in citrate buffer (10 mM, pH 6.0) using a microwave pressure cooker. The CXCR4 antibody (Abcam, ab2074) was used at 1:50 and CXCL12 (R & D Systems, MAB350) at 1:100. Digital images were acquired with the BLISS Imaging System (Bacus Laboratory, Lombard, Ill., USA). Immunostaining intensity was recorded as absent (1), weak (2), moderate (3), or strong (4) and as the percentage of cells staining on a scale of 1-100%. The product of each (intensity×percentage) was used to calculate a staining score for each tissue. Scoring was performed in a blinded fashion using the Profiler Web-based telepathology system (http://, followed by, pvdb.path.med.umich.edu/htma/profiler/index.jsp).

Statistical analysis GeneChip expression values were analyzed using a t-statistic test and by calculation of fold change between data sets. Genes that exhibited both a large t-statistic (>10.0) and a large fold change (>2.0) were considered to be differentially expressed. All other data were assessed by t-test or analysis of variance with P<0.05 considered statistically significant.

EXAMPLE II

Figure 1:
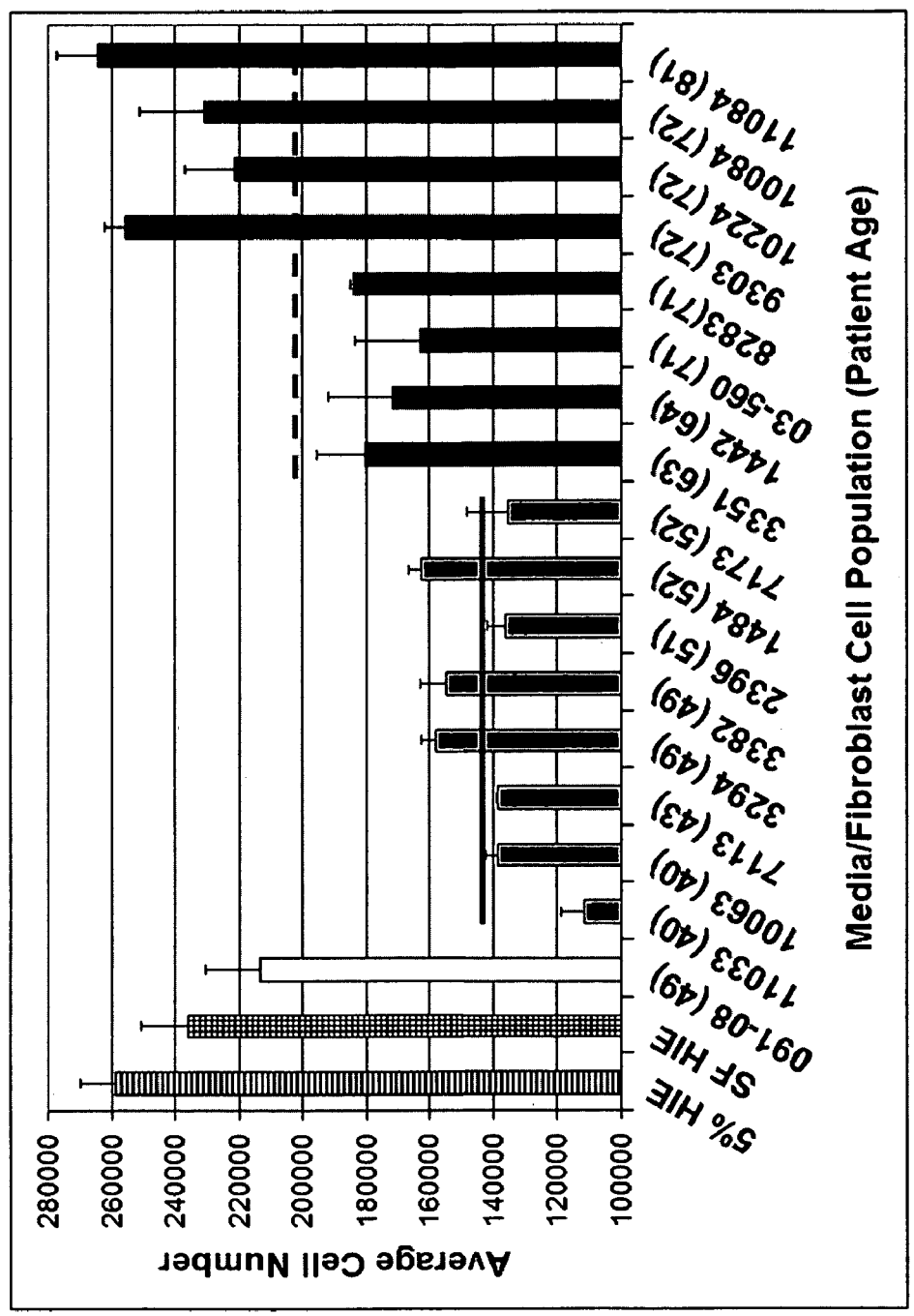
FIG. 1 shows conditioned media from aged prostate stromal fibroblasts induce growth of N15C6 prostate epithelial cells. N15C6 prostate epithelial cells were grown for 96 h in 5% HIE, defined serum-free media (SF HIE) or SF HIE media grown for 48 h in the presence of fibroblast cell populations indicated by patient age (in parentheses). Fibroblast population 091-08 was derived from cancer-associated stroma; the rest were derived from histologically benign tissues. Average cell growth in media from younger patients (aged 40-52; gray bars) is shown by solid line; average growth in media from older patients (aged 63-81; black bars) is shown by dashed line. Epithelial cell growth was significantly facilitated by media from older fibroblasts but inhibited by media from younger fibroblasts (P=0.002).

This example shows that older fibroblasts are less able to repress epithelial cell proliferation than younger fibroblasts in vitro. N15C6 human prostate epithelial cells demonstrated differential growth in conditioned media acquired from fibroblast cell populations originating from younger (40-52 years old) compared with older (63-72 years old) patients (FIG. 1). The average cell number for N15C6 cells grown in defined serum-free HIE conditioned media acquired from younger fibroblasts, 142 000 (±16 400) cells, was significantly less than that for the same cells grown in defined serum-free HIE media alone, 235 990 (±14 680) (P<0.001) (FIG. 1). This indicated that conditioned media from younger fibroblast cells exerted a growth-suppressive effect on N15C6 prostate epithelial cells. In contrast, the average cell number for N15C6 cells grown in the presence of defined serumfree HIE conditioned media acquired from older fibroblasts, 209 000 (±40 000) cells, was higher than that for the same cells grown in the presence of defined serum-free HIE media acquired from younger fibroblasts (P<0.001) and was similar to that obtained using defined serum-free HIE conditioned media alone (FIG. 1). Conditioned media acquired from the fibroblasts of two older men, (72 years old) and (81 years old), elicited a proliferative response from N15C6 cells that actually exceeded the response observed using defined serum-free HIE media alone (FIG. 1). These results demonstrate that conditioned media from older prostate fibroblasts were less able to suppress N15C6 prostate epithelial cell growth, and in two instances actually induced N15C6 cell growth.

The fibroblasts used in the experiments described above were grown in culture from histologically verified benign tissues with one exception, which were grown from tissue containing malignant prostate glands. Conditioned media from the cancer-associated fibroblasts were not growth suppressive, even though the tissue was acquired from a patient 49 years of age at the time of surgery.

EXAMPLE III

This example shows how differential gene expression patterns distinguish older fibroblasts from younger prostate fibroblasts. The gene expression profiles of four fibroblast cell populations derived from younger patients, (40 years old), (40 years old), (51 years old) and (52 years old) and of two derived from older patients, 1442 (64 years old) and (71 years old), was obtained using Affymetrix U133A GeneChips and compared. These experiments identified 54 unique, differentially expressed, transcripts, with 41/54 (76%) up-regulated and 13/54 (24%) down-regulated in older compared with younger stromal fibroblasts. Twelve of the transcripts (e.g., representing nine unique sequences) that were up-regulated in RNA derived from older compared with younger prostate stromal fibroblasts encoded secreted proteins. The upregulated transcripts included transcripts for the genes encoding the following CXC-type cytokines: CXCL1, CXCL5, CXCL6, and CXCL12. Of these transcripts, the most highly up-regulated was for the gene encoding the secreted chemokine CXCL12, also known as SDF-1 (stromal derived factor 1), which was present at 3.4-fold higher levels in RNA prepared from older compared with younger stromal fibroblasts. Quantitative RT-PCR using a highly sensitive TaqMan assay measured 2-36-fold higher levels of CXCL1, CXCL5, CXCL6, and CXCL12 transcripts in older compared with younger fibroblasts (P<0.001) (see, e.g., FIGS. 6A and 6B), confirming that these transcripts were more abundant in older prostate stromal fibroblasts.

EXAMPLE IV

This example shows that CXCL12 is secreted by prostate stromal fibroblasts and induces prostate epithelial cell proliferation. An ELISA specific for CXCL12 confirmed that older stromal fibroblasts secreted higher levels of the CXCL12 protein into the culture media (3.70-17.47 pg mL$^{-1}$, or 0.47-2.24 pM) compared with younger fibroblasts (3.71-0.65 pg mL$^{-1}$, or 0.47-0.83 pM). The same assay did not detect CXCL12 in culture media from N15C6 cells and detected very low levels of CXCL12 in culture media from LNCaP cells (3.9±0.035 pg mL$^{-1}$, or 0.50 pM). These data demonstrated that older prostate fibroblasts secreted higher levels of CXCL12 than younger prostate fibroblasts or epithelial cells.

Figure 2:
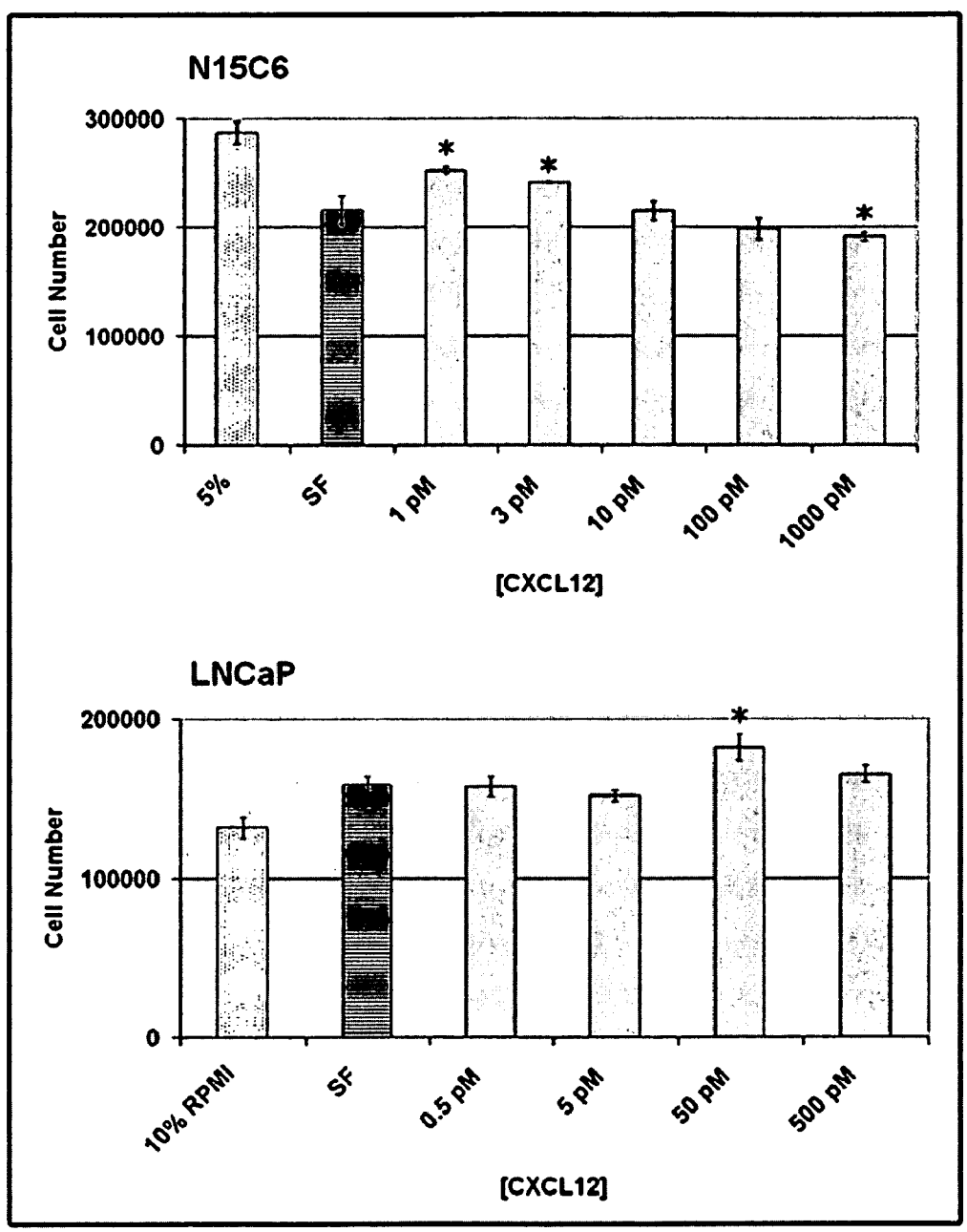
FIG. 2 shows low [CXCL12] induces the proliferation of N15C6 and LNCaP prostate epithelial cells. N15C6 or LNCaP prostate epithelial cells were grown for 72 h in complete media (5% HIE for N15C6, 10% RPMI for LNCaP), defined serum-free HIE (SF) or SF supplemented to the indicated concentration of CXCL12. N15C6 cellular proliferation was induced above SF levels at 1-3 pM CXCL12 but was suppressed at 1000 pM CXCL12, whereas LNCaP proliferation was induced at 50 pM CXCL12 (P<0.001).

Whether the addition of CXCL12 to defined serum-free media in the concentration range secreted by older prostate fibroblasts induced N15C6 or LNCaP prostate epithelial cell proliferation was examined. As seen in FIG. 2, the addition of CXCL12 at 1-3 pM for N15C6 cells, or 50 pM for LNCaP cells, was growth stimulatory and facilitated growth significantly above levels observed in defined serum-free media alone (P<0.001). Although the proliferative effect of low levels of CXCL12 was modest, the addition of higher concentrations of CXCL12 in both cases was clearly growth inhibitory. Together with the conditioned media experiments reported above, these results show that CXCL12 is secreted by human prostate stromal fibroblasts and directly stimulates human prostate epithelial cell proliferation at very low, picomolar concentrations.

EXAMPLE V

Figure 3:
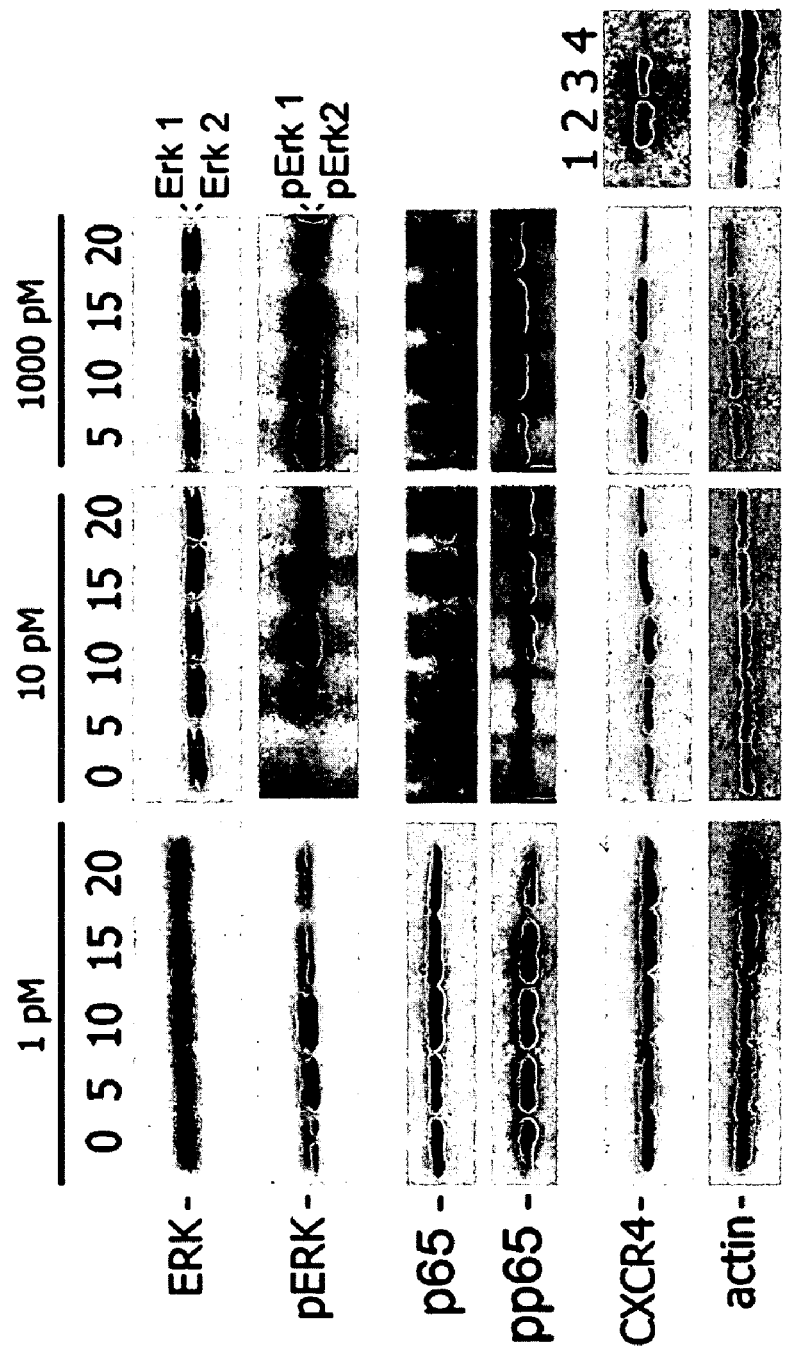
FIG. 3 shows low [CXCL12] induces ERK and NF-kappaB phosphorylation. N15C6 cells were grown in 5% HIE media supplemented to 1, 10, or 1000 pM CXCL12 for 0, 5, 10, 15 or 20 min, then harvested, lysed, and examined by Western blot analysis. The treatment did not affect total levels of the ERK or NF-kappaB (p65) proteins, but did rapidly and transiently induce ERK phosphorylation (ppERK) and NF-kappaB (pp65). Actin is shown as a loading control (bottom panel). CXCR4 and actin expression are also shown for N15C6 cells in serum-free media (lane 1), LNCaP cells (lane 2) and two primary cultures of explanted prostate epithelial tissues (lanes 3 and 4) as controls.

This example describes how CXCL12 stimulates phosphorylation of ERK ½ and NF-kappaB. Of the three major downstream signaling pathways stimulated by CXCR4/CXCL12 binding—PI3K/FAK, Ras/ERK and PI3K/NfkappaB—both the Ras-mediated ERK pathway and the PI3K mediated NF-kappaB pathway are associated with cellular proliferation. Whether CXCL12, which was observed to induce N15C6 and LNCaP cellular proliferation, also induced ERK and/or NF-kappaB activation, was examined. As seen in FIG. 3, exposure of N15C6 cells to 1 pM, 10 pM or 1000 pM CXCL12 induced rapid, transient ERK phosphorylation and activation. ERK phosphorylation was maximal after 10 min of exposure to 1 or 10 pM CXCL12 and after just 5 min of exposure at 1000 pM CXCL12. Phosphorylation of the p65 subunit of NF-kappaB was not evident after exposure of N15C6 cells to 1 PM CXCL12 but was evident after 10 min exposure to 10 pM or 1000 pM CXCL12. CXCR4 levels were not detectably altered in cells exposed to CXCL12 over the same time period (FIG. 3). These data show that even the very low levels of CXCL12 secreted by older prostate fibroblasts and associated with N15C6 and LNCaP cellular proliferation are sufficient for phosphorylation and activation of ERK ½ and NF-kappaB.

EXAMPLE VI

Figure 4:
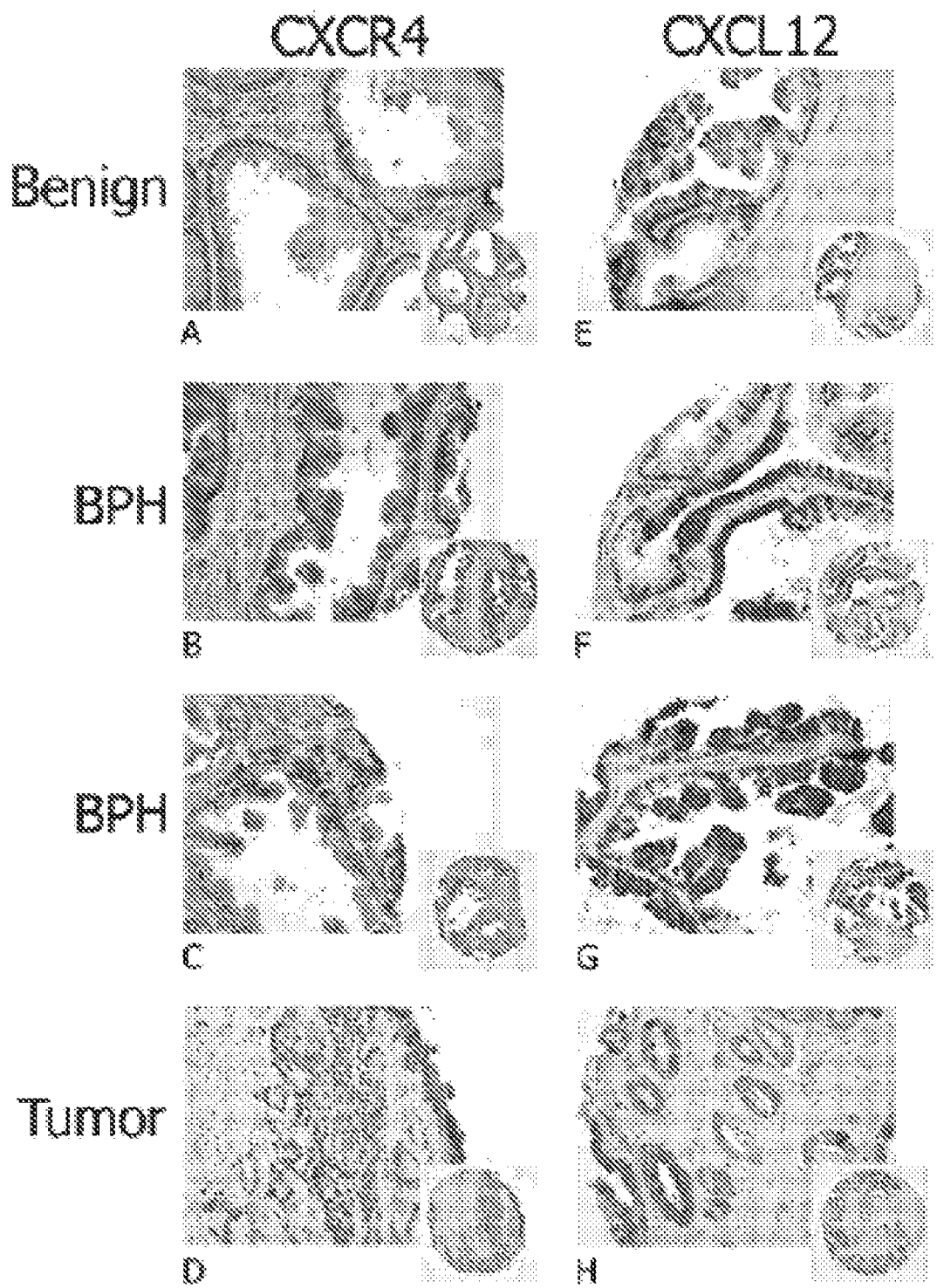
FIG. 4 shows benign, hyperplastic and malignant human prostate glands express CXCR4 and CXCL12. Representative portions of identical tissue microarrays are shown of human benign prostate tissues (A, E), benign prostatic hypertrophy, epithelial tissues (B, C, F, G), and malignant prostate tissues (D, H) after incubation with primary antibodies against CXCR4 (1:100) (A-D) or CXCL12 (1:100) (E-H) and visualization using immunoperoxidase staining.
Figure 5:
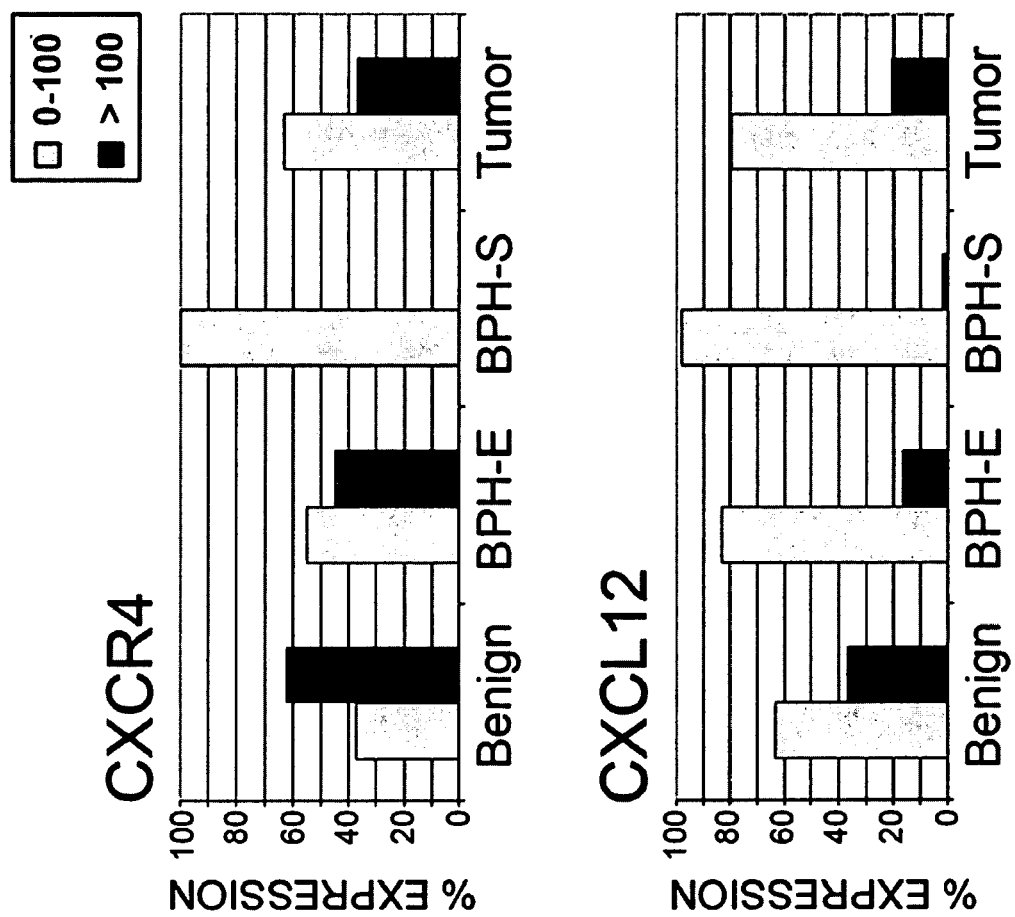
FIG. 5 shows quantitation of tissue microarray immunohistochemical analysis. The percent expression of CXCR4 and CXCL12 in Benign, BPH-E, BPH-S and Tumor prostate tissues is shown. Gray bars, staining score 0-100; black bars, score >100.

This example describes how CXCL12 and CXCR4 proteins are expressed by human prostate tissues. Immunohistochemical analysis of a tissue microarray (TMA) was used to assess CXCL12 and CXCR4 protein expression in human prostate tissues (FIG. 4). Benign glands (24 tissue cores), epithelial BPH (BPH-E, 65 cores), and malignant glands (77 cores) demonstrated both CXCL12 and CXCR4 protein expression. Benign glands demonstrated the highest levels of expression for both proteins (FIG. 5). Malignant glands and BPH-E demonstrated equivalent CXCR4 expression, and CXCL12 levels were approximately half that of CXCR4 levels in the same tissues (FIG. 5). The expression pattern for CXCR4 was cytoplasmic and/or membraneous (FIG. 4A,B,D) with the exception of 14/65 (21%) samples of BPH-E, which demonstrated strong nuclear staining (FIG. 4C). The expression pattern for CXCL12 appeared to be exclusively membrane-bound, and reflected detection of the protein bound to the CXCR4 receptor (FIG. 4E-G).

EXAMPLE VII

This example shows secretion of CXCL1, CXCL5, CXCL6, and CXCL12 by aging human prostate stromal fibroblasts and promotion of epithelial and fibroblast cell proliferation.

Figure 6A:
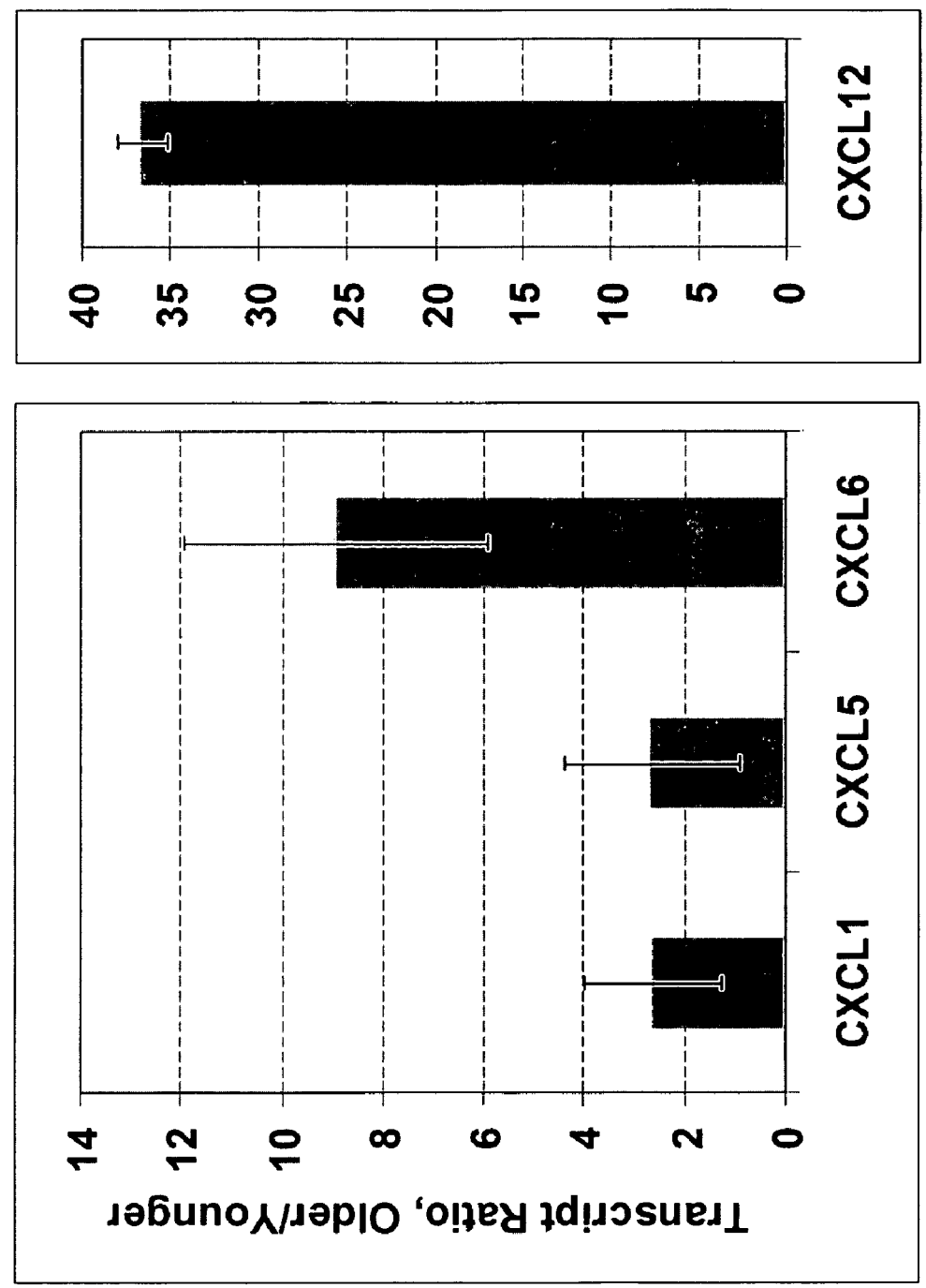
FIGS. 6A-D show secretion of CXC-type cytokines by aging human prostate stromal fibroblasts and promotion of epithelial and fibroblast cell proliferation.
Figure 6:
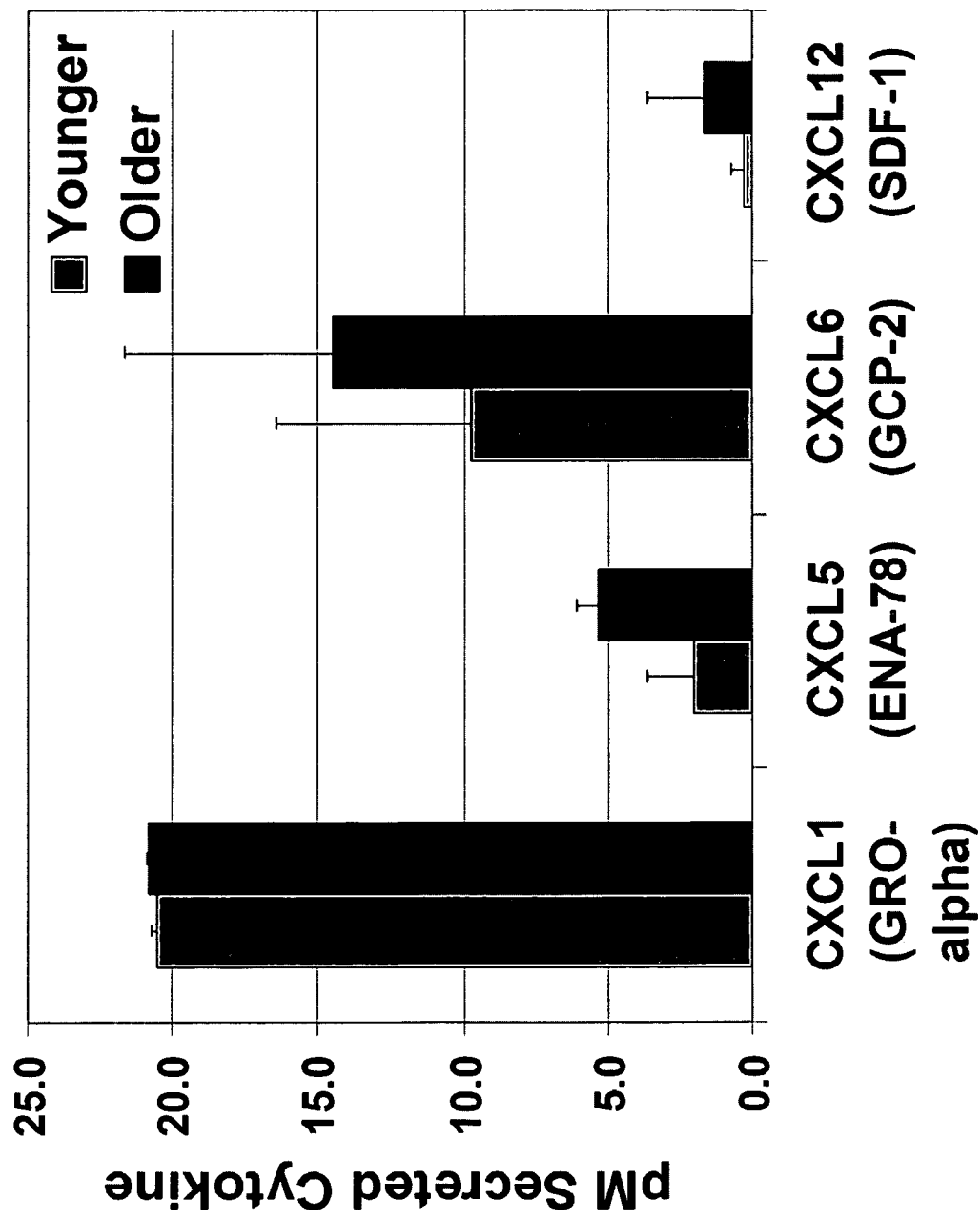
Figure 6:
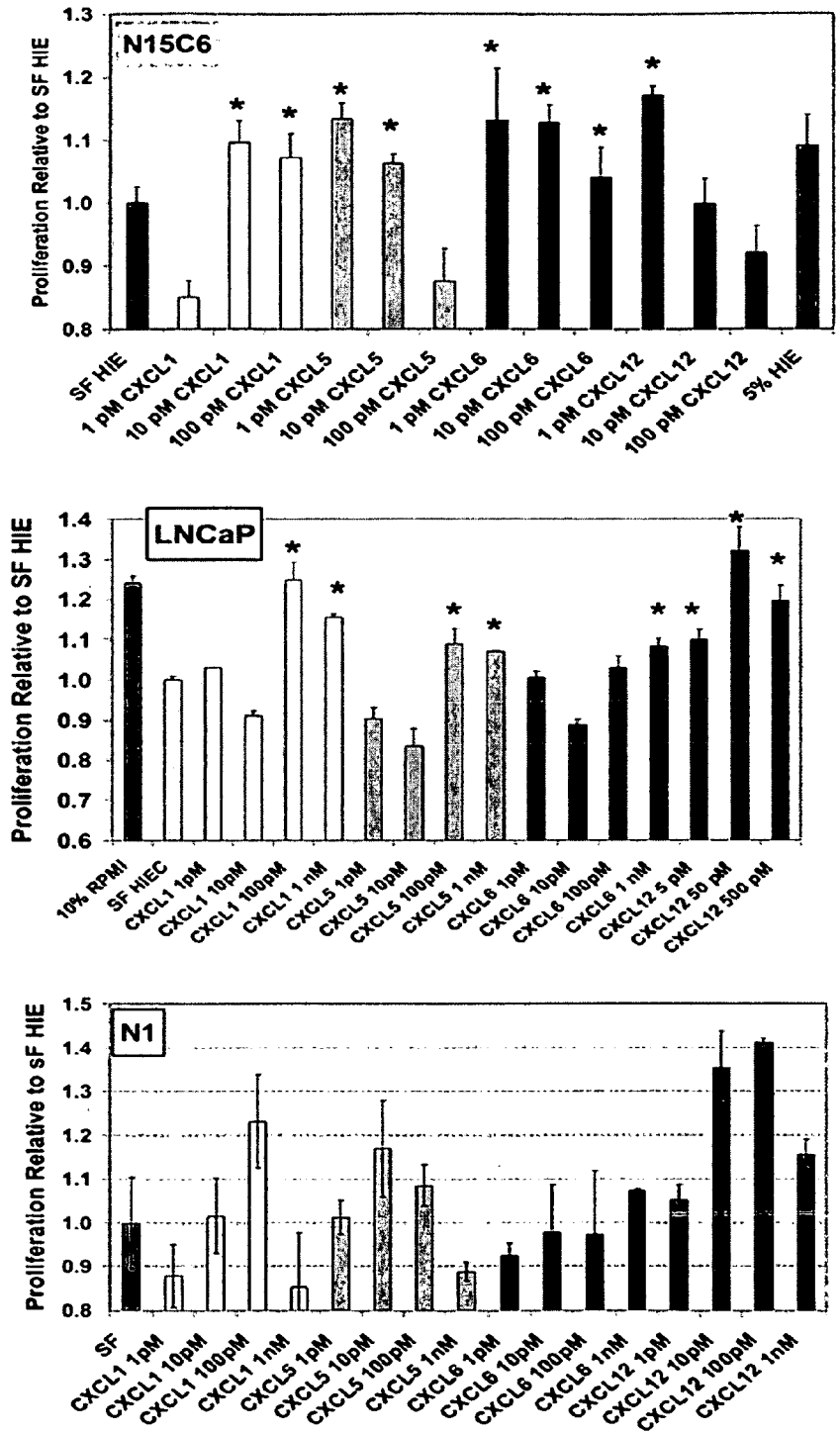

FIG. 6A describes qRT-PCR data showing that older human prostate stromal fibroblasts (N=3) express 2-3× higher levels of CXCL1, CXCL5, CXCL6, and CXCL12 gene transcripts compared to younger fibroblasts (N=3). Quantitative real-time assays were conducted with an Applied Biosystems 7900HT instrument and reagents. One microgram of RNA was reverse transcribed by use of Superscript III reverse transcriptase (Invitrogen, Carlsbad, Calif.).

The resulting cDNA was diluted 1:100. Real-time PCR was performed by use of Assays on Demand (Applied Bio- Systems, Foster City, Calif.) according to the manufacturer's instructions, except that Real Time Ready with Rox passive dye (QBioGene, Carlsbad, Calif.) was used in place of TaqMan Universal PCR Master Mix. Reactions were performed in triplicate, including no-template controls and an endogenous control probe to assess template concentration (ribosomal protein, large, PO). Cycle numbers to threshold were calculated by subtracting averaged control from averaged experimental values, and Fold Gene Expression was calculated by raising these values to the log 2. qRT-PCR experiments demonstrated that higher levels of CXCL1, CXCL5, CXCL6, and CXCL12 gene transcripts were detectable in RNA purified from primary human prostate stromal fibroblasts cultured from the prostates of older (N=3) compared to younger (N=3) men.

FIG. 6B describes ELISA data showing that older human prostate stromal fibroblasts (N=3) express 2-3× higher levels of CXCL1, CXCL5, CXCL6, and CXCL12 protein compared to younger fibroblasts (N=3). Primary human prostate stromal fibroblasts were grown in 0.01% BSA defined HIE for three days. The fibroblast-conditioned media was collected, serially concentrated using Centriplus centrifugal filters (Amicon) with a 3 kD molecular weight cutoff, and assessed using specific CXCL1, CXCL5, CXCL6, and CXCL12 ELISA systems (R&D Systems). All reactions were performed in duplicate and the resulting values averaged. The ELISA experiments showed that human prostate stromal fibroblasts cultured from the prostates of older (N=3) men secreted 2-3× higher protein levels for CXCL1, CXCL5, CXCL6, and CXCL12 compared to those cultured from younger men (N=3). This shows that CXCL1, CXCL5, CXCL6, and CXCL12 are transcribed, translated and secreted at higher levels by older compared to younger human prostate stromal fibroblasts.

FIG. 6C describes how CXCL1, CXCL5, CXCL6, and CXCL12 stimulate N15C6 prostate epithelial cell proliferation, N1 prostate fibroblast cell proliferation, and LNCaP prostate epithelial cell proliferation compared to serum-free (SF HIE) media alone. "Add back" assays were next performed to determine whether the addition of exogenous CXCL1, CXCL5, CXCL6, and CXCL12 to defined, serum-free media induced N16C6 or LNCaP prostate epithelial or N1 fibroblast cell proliferation. For these and all experiments utilizing N15C6 and LNCaP cells, the N15C6 and N1 cells were used between passage 35-45, and LNCaP cells between passages 25-35, for consistency. All recombinant CXC proteins were obtained from R&D systems (e.g., CXCL1, #275-GR, CXCL5, #254-X; CXCL6, #333-GC, and SDF1 alpha/CXCL12, #350-NS). Cells were plated at 50,000 cells/well in triplicate, treated for 96 hours, and counted. As seen in FIG. 6C, all four CXC-type chemokines tested stimulated both prostate fibroblast and epithelial cell proliferation above levels observed for SF HIE alone. Moreover, the concentrations for CXCL1, CXCL5, CXCL6 and CXCL12 observed to be growth-stimulatory for prostate epithelial cells were similar to those secreted into the media by older prostate stromal fibroblasts (see, e.g., FIGS. 6A and 6B). Together with the conditioned media experiments reported above, these results show that CXCL1, CXCL5, CXCL6 and CXCL12 are secreted by aging human prostate stromal fibroblasts and directly stimulate human prostate epithelial and stromal fibroblast cellular proliferation at low, physiological concentrations. In addition, this shows that CXCL1, CXCL5, CXCL6 and CXCL12 are capable of stimulating the proliferation of both prostate epithelial and stromal fibroblast cells, which are the same cell types that are overly-proliferative in malignant (epithelial cells) and benign (epithelial and fibroblast cells) proliferative diseases of the prostate.

Figure 6D:
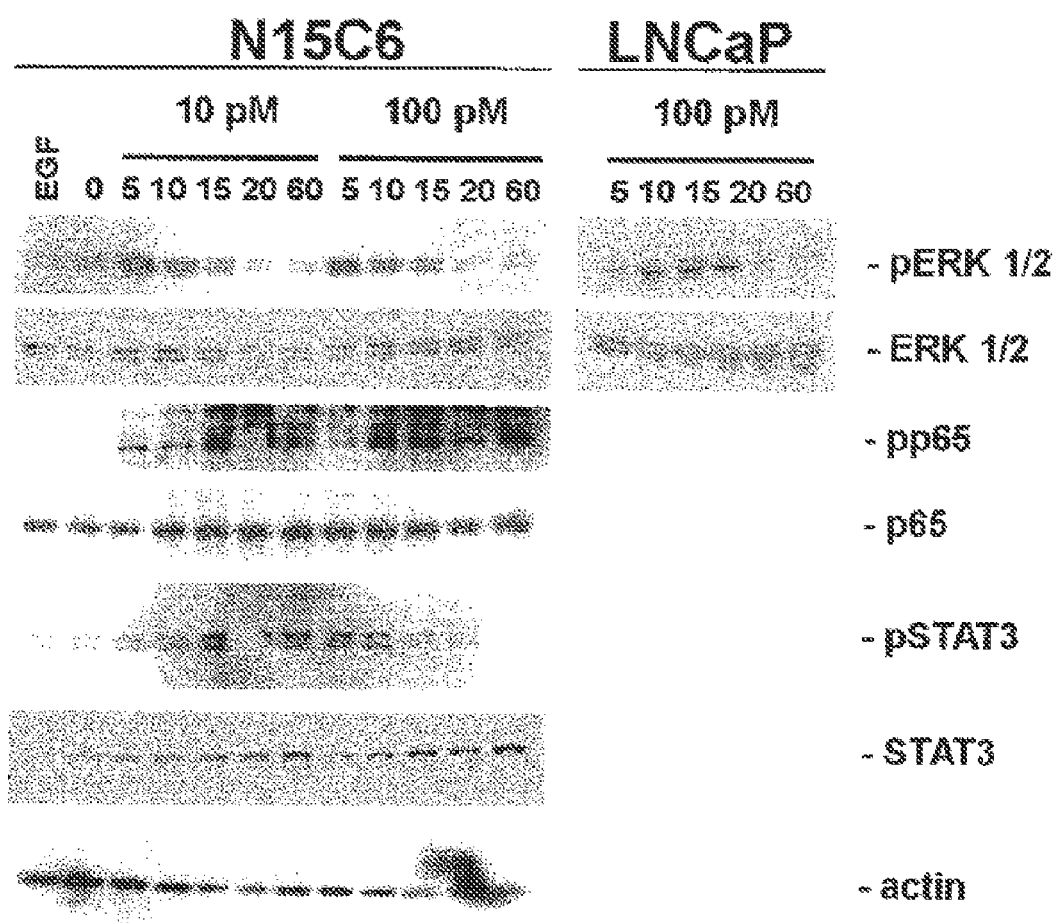

FIG. 6D describes how CXCL5 stimulates the phosphorylation and activation of ERK ½ and pERK ½ in both N15C6 and LNCaP cells, p65 (the catalytic subunit of NfkappaB) in N15C6 cells, and STAT3 in N15C6 cells. Cells were lysed, proteins resolved by electrophoresis, and electroblotting was carried out as described previously (Chaib et al., 2001, Cancer Res. 61, 2390-2394; incorporated herein by reference in its entirety). Proteins were detected using antibodies against phospho-ERK½, total ERK½, phospho-p65, total p65, STAT3, phospho-STAT3, or beta-actin, in conjunction with an ECL detection system. CXCL5 stimulated the phosphorylation and activation of ERK ½, p65, and STAT3.

The present invention is not limited to a particular mechanism. Indeed, an understanding of the mechanism is not necessary to practice the present invention. Nonetheless, these results show that N15C6 and LNCaP prostate epithelial cell proliferation in response to CXCL12 (as shown in Examples I-VI) and CXCL5 is mediated by activation of the Ras signaling pathway, resulting in ERK ½ phosphorylation.

The present invention is not limited to a particular mechanism. Indeed, an understanding of the mechanism is not necessary to practice the present invention. Nonetheless, these results show that STAT3 and the p65 (Re1) subunit of NF-kappaB may be phosphorylated in response to CXCL5 treatment of N15C6 cells. P65 activation is downstream of PI3K activation, and STAT3 activation is downstream of either/both ERK ½ and PI3K activation.

The present invention is not limited to a particular mechanism. Indeed, an understanding of the mechanism is not necessary to practice the present invention. Nonetheless, these results show that both CXCL12 and CXCL5 activate multiple signaling pathways involved in cellular proliferation.

EXAMPLE VIII

Figure 7:
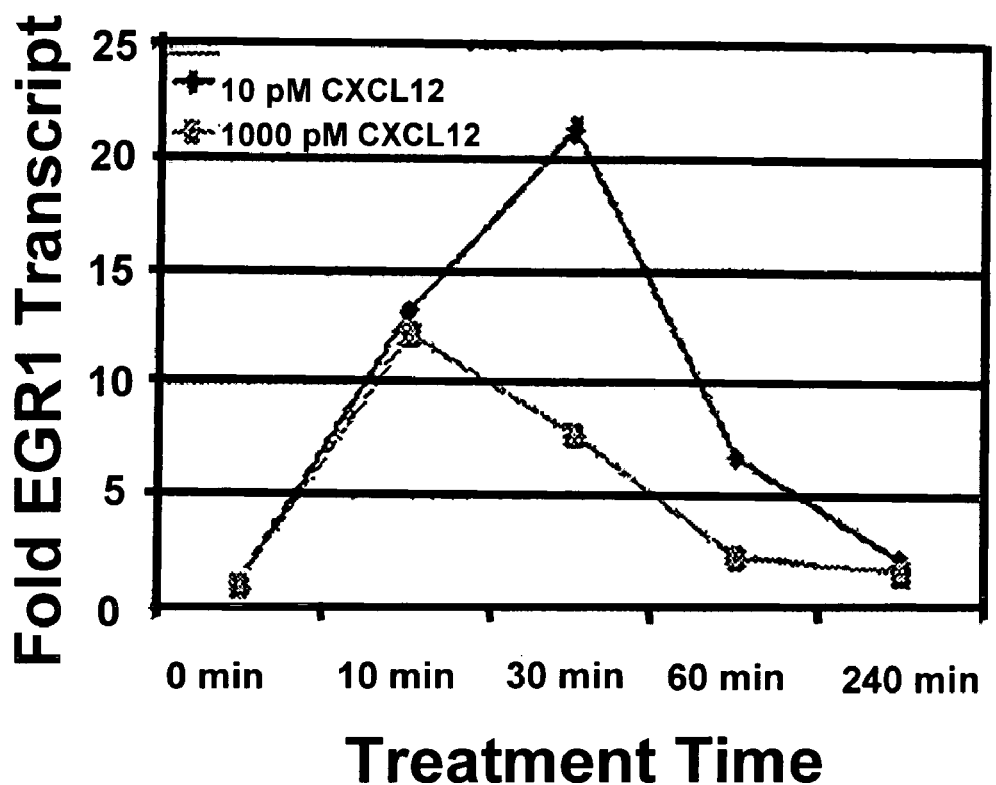
FIG. 7A and FIG. 7B show that CXCL5 stimulates gene transcription in prostate cells.
Figure 7:
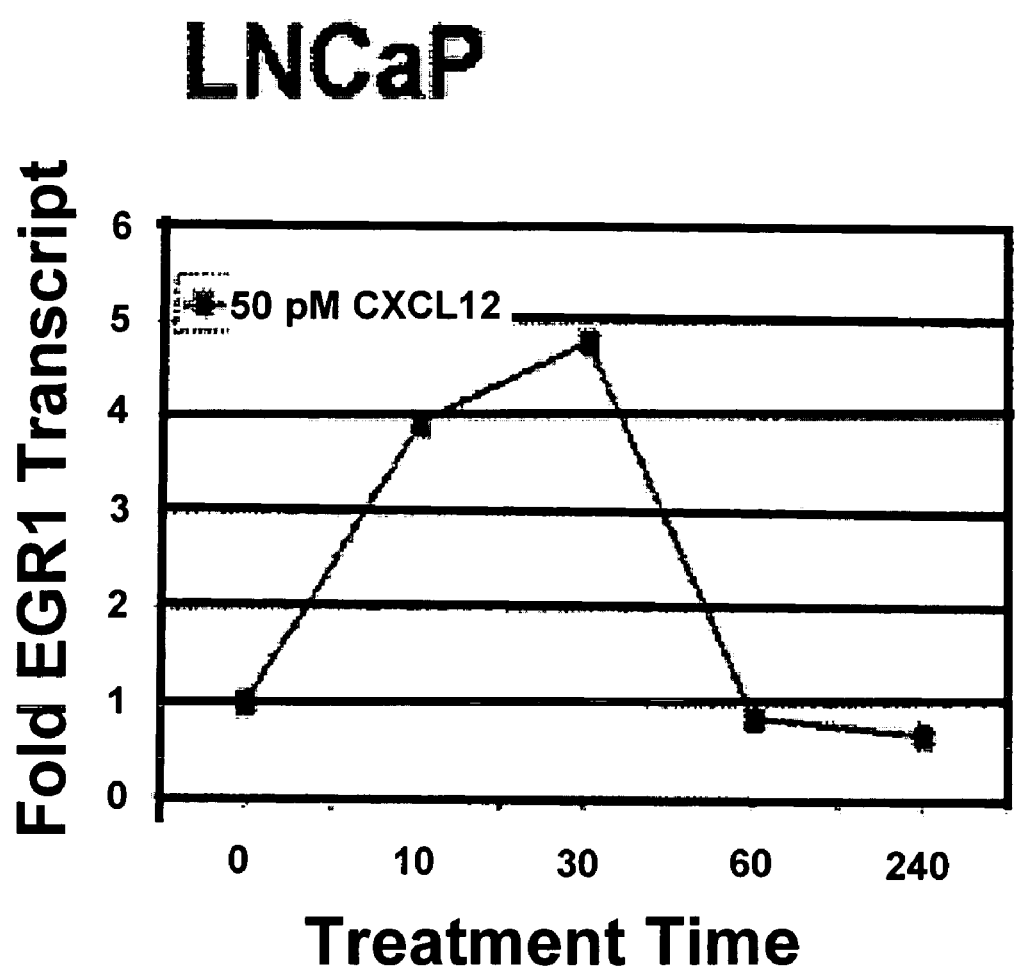

This example shows that CXCL5 stimulates gene transcription in prostate cells. As shown in FIG. 7, N15C6 cells were grown in SF HIE media supplemented with 10 pM CXCL5, then harvested at the time points shown. Transcript levels are shown after normalization to those of the control probe RPLPO, Hs99999902_ml (Applied Biosystems, Inc.) and are set at one-fold at time 0. Fold transcript levels for EGR1, AREG (Amphiregulin) and CXCL12 (LEFT) and for CXCL5 (RIGHT) are shown (Y-axes use different scales in the two graphs). CXCL12/CXCR4 interactions lead to activation of ERK ½ and NFkappaB (see, e.g., Taichman, et al., Cancer Res. 2002 62(6):1832-7; Orimo, et al., Cell 2005 121(3):335-348; incorporated herein by reference in their entireties). NFkappaB is a transcription factor, and ERK ½ phosphorylates Elk-1, a transcription factor. Both NFkappaB and Elk-1 activate the transcription of Early Growth Response 1 (EGR1), itself a transcription factor implicated in growth factor expression and tumor development. In experiments conducted during the development of embodiments for the present invention, it was shown that the same low, picomolar levels of CXCL12 that stimulate cellular proliferation in N15C6 (10 pM) and LNCaP (50 pM) cells also stimulate a transcriptional response resulting in EGR1 expression. In experiments conducted during the development of embodiments for the present invention it was shown that CXCL5 stimulates a similar transcriptional response. Because CXCL5 signals through similar pathways as CXCL12, it is expected that CXCL5 elicits a transcriptional response in both prostate epithelial and stromal fibroblast cells.

EXAMPLE IX

Figure 8:
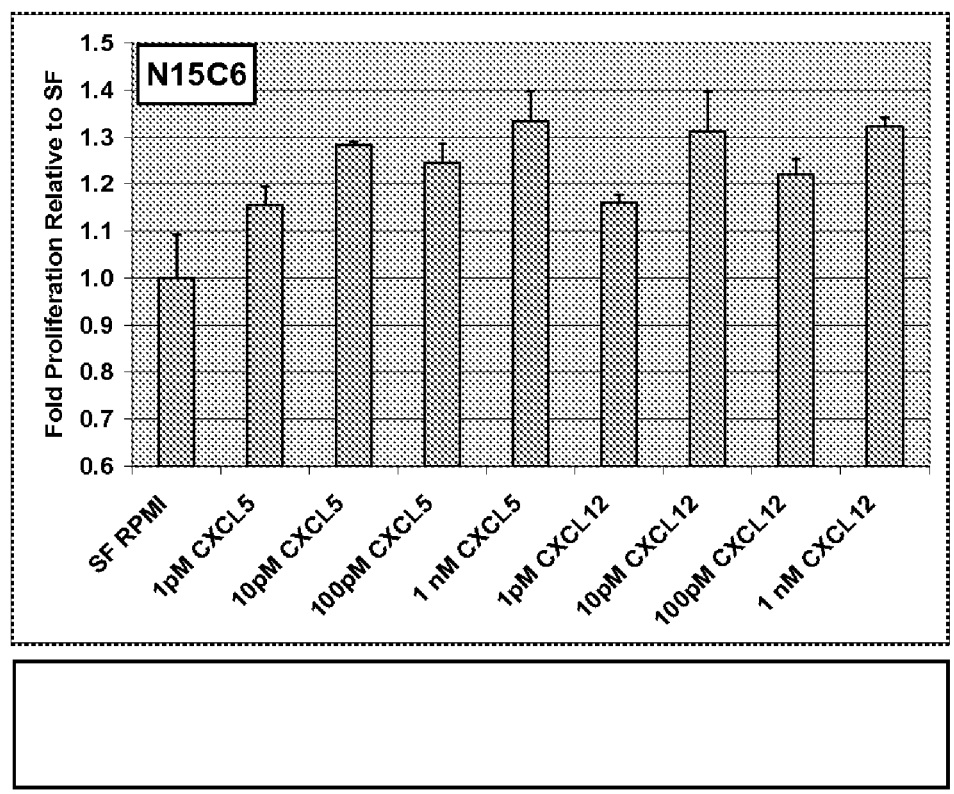
FIG. 8 shows that N15C6 cells proliferate equivalently in response to CXCL5 and CXCL12.
Figure 9:
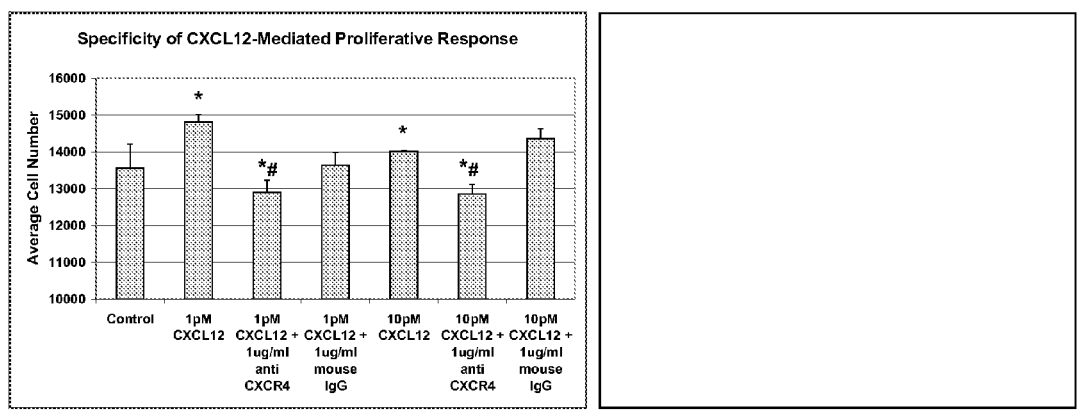
FIG. 9 shows the specificity of CXCL12-mediated proliferative response. N15C6 cells were seeded at 10,000 cells and allowed to proliferate for 72 hours in SF HIE (control) or SF HIE supplemented as shown. Proliferation in 1 pM or 1 pM CXCL12 was significantly higher than that in control media (*). Proliferation in response to CXCL12 was significantly abrogated in the presence of 1 ug/ml CXCR4 (*#) but not in the presence of the mouse IgG mouse isotype control.

This example describes the proliferative Response of Human Prostate Epithelial and Fibroblast Cells to CXCL5. As shown in FIG. 8, N15C6 cells proliferated equivalently in response to CXCL5 and CXCL12. As shown in FIG. 9, treatment of the cells with antibody against the receptor (CXCR4) abrogated the CXCL12 proliferative response, whereas treatment of the cells with the IgG isotype control did not.

In experiments conducted during the development of embodiments for the present invention it was shown that in N15C6 cells, CXCL5 concentrations of 1-10 pM stimulated proliferation, and concentrations of >100 μM inhibited proliferation. In experiments conducted during the development of embodiments for the present invention it was shown that in LNCaP cells, CXCL5 concentrations of 1-10 pM did not stimulate proliferation, whereas concentrations of >100 μM stimulated proliferation.

As shown in FIG. 3, N15C6 cells grown in 5% HIE media supplemented to 1, 10, or 1000 pM CXCL12 for 0, 5, 10, 15 or 20 min, harvested, lysed, and examined by Western blot analysis (e.g., using antibodies to Raf1, MEK½, and ERK½ (Ras pathway) and Akt, FAK, or STAT3 (PI3K pathway), and the phospho-forms of these proteins). As shown in FIG. 6D, CXCL5 is shown to stimulate the phosphorylation and activation of ERK ½ , p65 (the catalytic subunit of NfkappaB) and STAT3 (e.g., proteins were detected using antibodies against phospho-ERK½, total ERK½, phospho-p65, total p65, STAT3, phospho-STAT3, or beta-actin, in conjunction with an ECL detection system. CXCL5 stimulated the phosphorylation and activation of ERK ½, p65, and STAT3).

Figure 10:
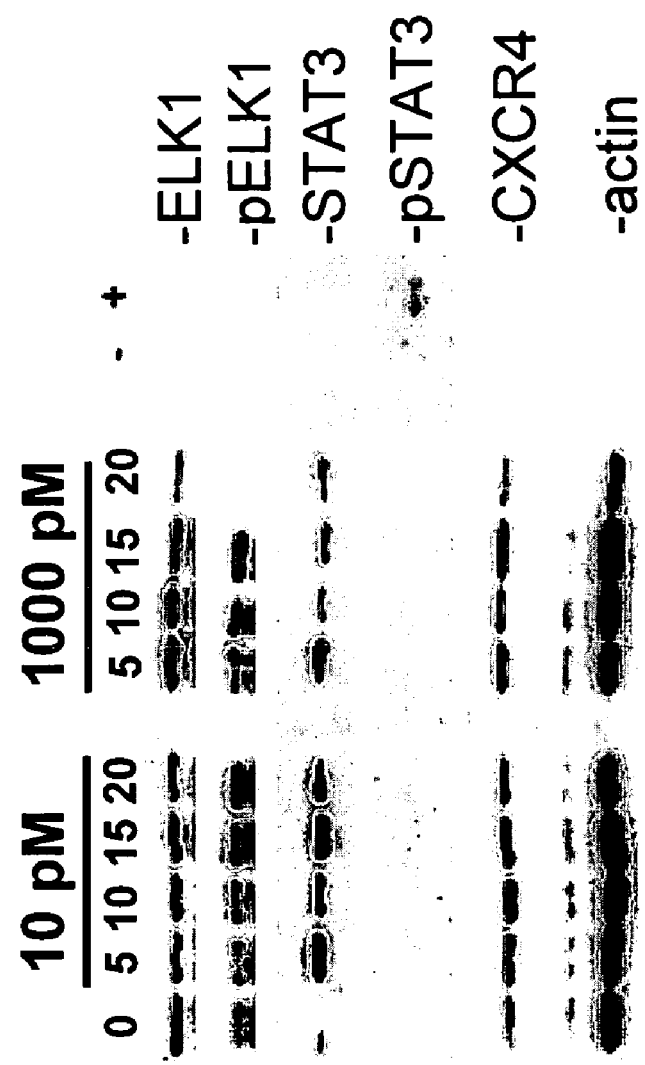
FIG. 10 demonstrates downstream signaling from CXCL12/CXCR4 to ERK ½ to ELK1. N15C6 cells were grown in 5% HIE median supplemented to 10, or 1000 pM CXCL12 for 0, 5, 10, 15 or 20 minutes.
Figure 11:
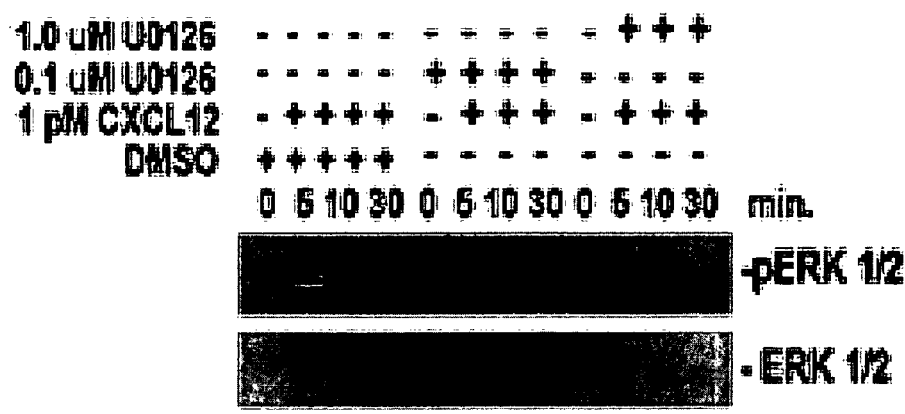
FIGS. 11A, 11B and 11C shows that in N16C6 cells treated with the MEK inhibitor (U0126) CXCL12 did not stimulate ERK phosphorylation, cell proliferation or EGR1 transcription.
Figure 11:
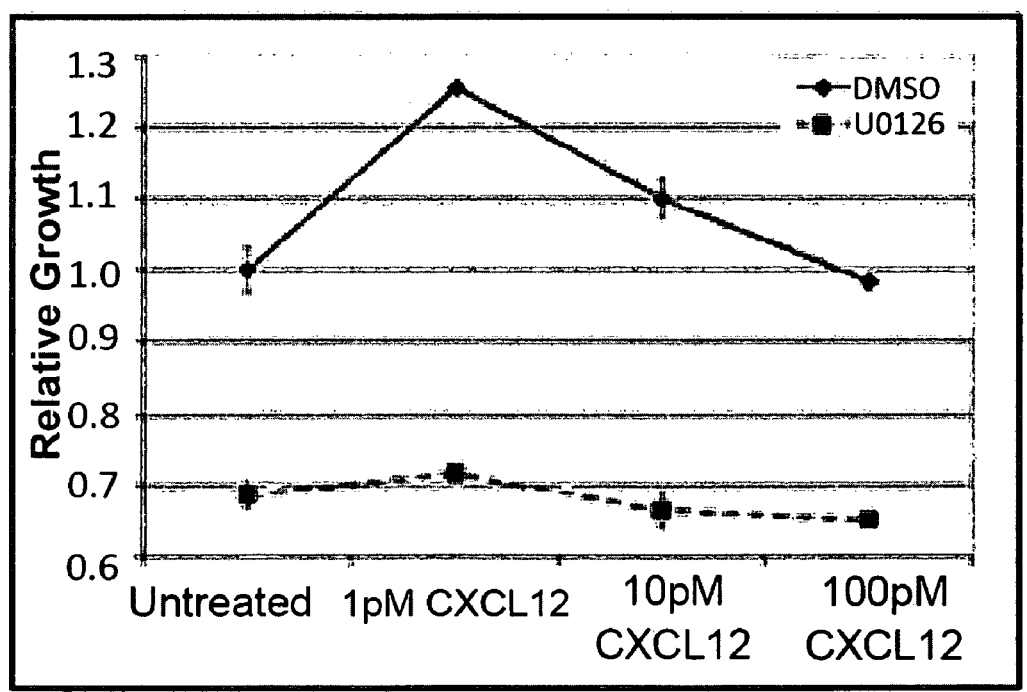
Figure 11:
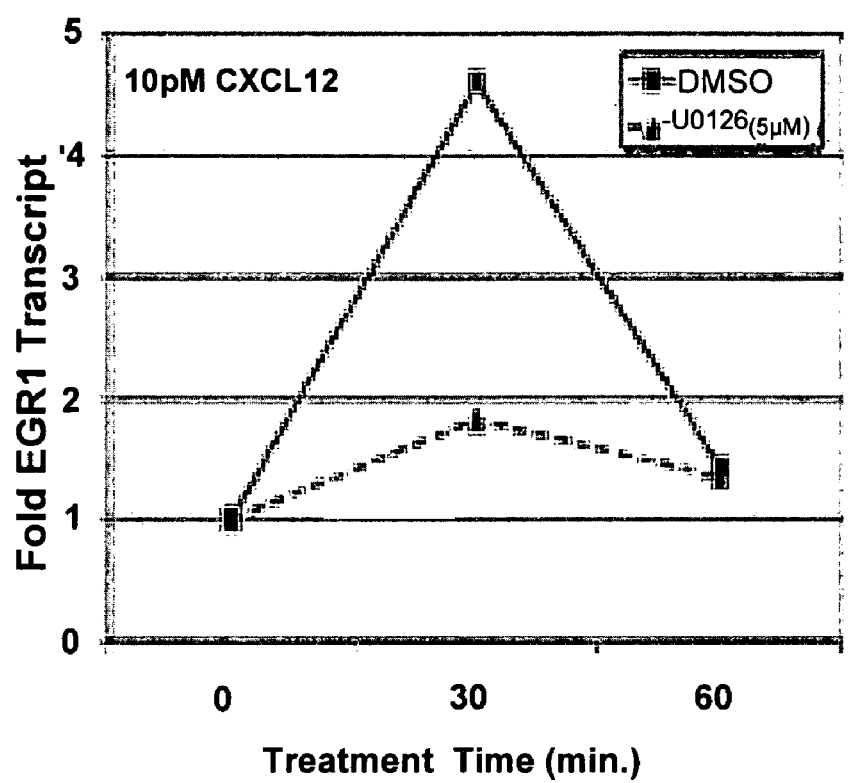
Figure 12:
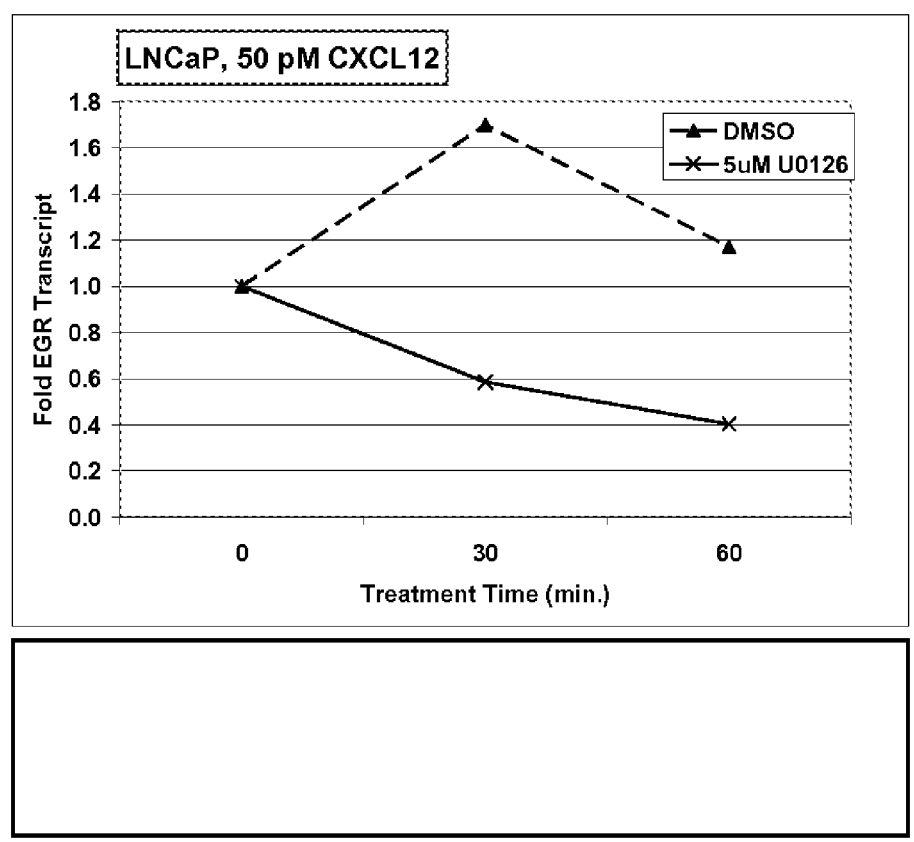
FIG. 12 shows that U0126 ablated CXCL12 stimulated transcription in LNCaP cells.

FIG. 10 demonstrates downstream signaling from CXCL12/CXCR4 to ERK ½ to ELK1. FIGS. 11A, 11B and 11C show that in N15C6 cells treated with the MEK inhibitor (U0126) CXCL12 did not stimulate ERK phosphorylation, cell proliferation or EGR1 transcription. FIG. 12 shows that U0126 ablated CXCL12 stimulated transcription in LNCaP cells. It is anticipated that U0126 will inhibit the effect of CXCL5 in N15C6 and LNCaP cells in a similar manner.

EXAMPLE X

Figure 13:
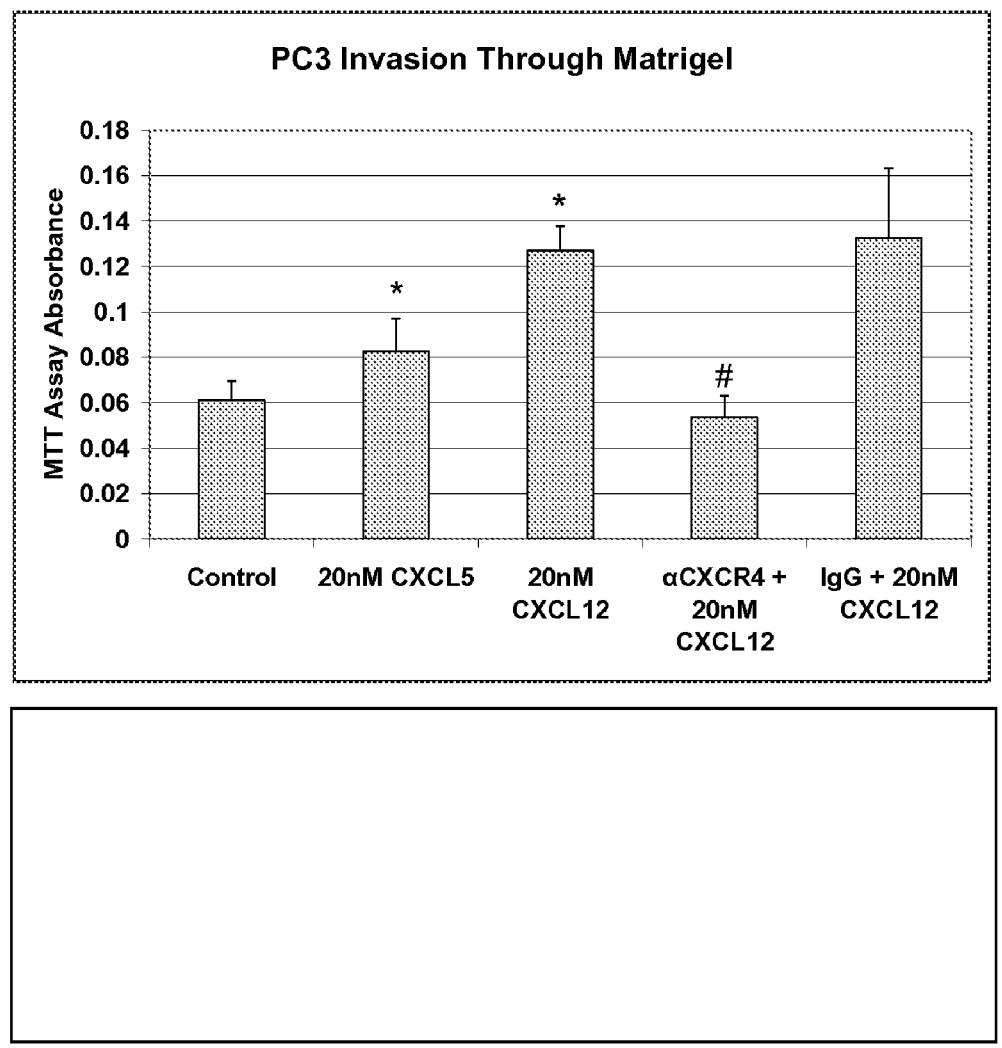
FIG. 13 shows that both CXCL5 and CXCL12 stimulate invasion of PC3 prostate cancer cells through Matrigel. Invasion of PC3 cells through Matrigel in response to 20 nM CXCL5 or 20 nM CXCL12 was significantly higher than that in control media (*). Invasiveness in response to CXCL12 was significantly abrogated in the presence of 1 ug/ml CXCR4 (*#) but not in the presence of the mouse IgG mouse isotype control.

This example demonstrates that both CXCL5 and CXCL12 stimulate invasion of PC3 prostate cancer cells through Matrigel. In experiments conducted during the development of embodiments for the present invention it was shown that PC3 cells stimulated with 20 nM CXCL12/2% RPMI invade through Matrigel at significantly higher levels than those stimulated with 2% RPMI alone. As shown in FIG. 13, the effects of CXCL5 on PC3 cell invasion were tested. PC3 cells invaded through Matrigel in response to both CXCL5 and CXCL12. In experiments conducted during the development of embodiments for the present invention, the effect for CXCL12 was abrogated when the cells were pre-treated with antibody against the CXCR4 receptor but not when the cells were treated with the IgG isotype control. It is contemplated that the effect for CXCL5 is also abrogated when the cells are pre-treated with antibody against the CXCR2 receptor. It is contemplated that PI3K-mediated FAK activation is involved in CXCL5-stimulated epithelial cell migration. Protein purified from cells exposed to CXCL5 using Western blot analysis and antibodies to FAK, Crk, p130Cas, and the phospho-forms of these proteins will be examined. It is contemplated that PI3K signaling involvement in the migratory/invasive response to cytokine stimulation by CXCL5 occurs through, for example, phosphorylation of FAK, Crk and p130Cas. It is contemplated that inhibition of downstream PI3K signaling abrogates the migratory/invasive response of CXCL5. For example, it is contemplated that N15C6 or LNCaP cells pre-treated with PI3K inhibitors (e.g., 100 nM wortmannin or 20 uM LY294002a) or 10 mM of the RAFTK/Pyk2 inhibitor tyrphostin A9 for 2 hours, then exposed to CXCL5 previously shown to stimulate the migratory/invasive response, for 2 hours, abroagates the migratory/invasive response of CXCL5.

EXAMPLE XI

This example describes the materials and methods used for Examples XII-XV.

Cell Cultures. N15C6 cells, developed as described previously, were used at passages 35-45 (see, e.g., Macoska J A, et al., 2004 Cancer Genet. Cytogenet. 154, 36-43; Begley L, 2006 Genes Chromosomes Cancer. 45(2): 136-46; incorporated herein by reference in their entireties). LNCaP cells were acquired from the American Type Culture Collection (ATCC#CRL-1740), were used at passages 25-35 (see, e.g., Horoszewicz J S, 1983 Cancer Res. 43: 1809-1818; incorporated herein by reference in its entirety). Cells were maintained in 5% HIE media [Ham's F12 (Mediatech Inc. Herndon, Va.) with 5% FBS (Life Technologies, Inc.), 5 ug/ml insulin, 10 ng/ml EGF, 1 ug/ml hydrocortisone (Sigma Chemical Co., St. Louis, Mo.) or in defined serum-free HIE media supplemented to 5 mM ethanolamine (Sigma Aldrich), 10 mM HEPES (Sigma Aldrich), 5 ug/ul transferring (Sigma Aldrich), 10 uM 3,3',5-triiodo-Lthyronine (Sigma Alrdich), 50 uM sodium selenite (Sigma Aldrich), 0.1% BSA (JRH Biosciences Lenexa, Kans.), 0.05 mg/ml gentamycin (Gibco), and 0.5 ug/ml fungizone (Cambrex Bioscience, Walkersville, Md.).

Proliferation Assays. Cellular proliferation was assessed after plating cells at 50,000 cell/well in triplicate in six well plates and counting cells after 24 and 96 hours of incubation as described previously (see, e.g., Macoska J A, et al., 2004 Cancer Genet. Cytogenet. 154, 36-43; incorporated herein by reference in its entirety). To assess the effects of exogenous CXCL12 on cellular proliferation, recombinant human SDF1 alpha/CXCL12 (R&D Systems, 350-NS) was added at the desired concentration in 1 ml SF HIE (or 1 ml SF HIE alone for control) to each well. The cells were re-fed at 48 and 72 hours growth and counted at 24 and 96 hours growth. Cell counts were normalized to 50,000 cells at 24 hours to account for any plating discrepancies. Averages and standard deviations of cell number were calculated for each time point under each media condition. Experiments utilizing U0126 were performed as above, except that cells were treated after plating for 2 hours with either DMSO (vehicle) or 5 uM U0126 before addition of CXCL12. Cells were maintained in media containing DMSO or U0126 for the entirety of the experiment. For the antibody blockade experiments, cells were plated at 10,000 cells per well in triplicate in 24 well dishes and pre-incubated with mouse IgG2aκ (BD Pharmingen 555571) or mouse anti-CXCR4 (BD Pharmingen 555971) at 1 ug/ml for 1 hour prior to CXCL12 addition. Cells were maintained in media containing appropriate antibodies for the entirety of the experiment, and cells were counted at 24 and 96 hours as above.

Affymetrix Human Genome U133 plus 2.0 Array Data Acquisition. RNA was purified from trypsinized cultured cells by homogenization in Trizol (Invitrogen, Carlsbad, Calif.) and additional processing using the Rneasy (Qiagen, Valencia, Calif.) cleanup procedure. Ten ug of RNA was used to obtain labeled cRNA following the Affymetrix Standard protocol. Expression intensity values for each gene were estimated using a method called Robust Multi-array Average (RMA) using tools available through Bioconductor (http://www, followed by, bioconductor.org). GeneChip gene expression values were normalized using a quantile normalization procedure.

Quantitative Real-Time PCR. All quantitative real-time assays were conducted with an Applied Biosystems 7900HT instrument and reagents. Cells were grown to 70% confluence in 60 mM dishes prior to RNA purification using the Trizol reagent (Invitrogen Life Technologies). Experiments utilizing U0126 were performed as above, except that cells were treated with DMSO (vehicle) or 5 uM U0126 for 2 hours, then grown in the presence or absence of CXCL12. For all experiments, one microgram of RNA was reverse transcribed by use of Superscript III reverse transcriptase (Invitrogen, Carlsbad, Calif.). The resulting cDNA was diluted 1:100. Real-time PCR was performed by use of Assays on Demand (Applied BioSystems, Foster City, Calif.) according to the manufacturer's instructions, except that Real Time Ready with Rox passive dye (QBioGene, Carlsbad, Calif.) was used in place of TaqMan Universal PCR Master Mix. Reactions were performed in triplicate, including no-template controls and an endogenous control probe to assess template concentration (ribosomal protein large, PO). Cycle numbers to threshold were calculated by subtracting averaged control from averaged experimental values, and Fold Gene Expression was calculated by raising these values to the log 2. FAM conjugated, gene specific assays were Hs00171022_ml for CXCL12, Hs00152928_ml for EGR1, Hs00170423_ml for CDH1, and Hs99999902_ml for the control, RPLPO.

Western Blot Analysis. Cells were lysed, proteins resolved by electrophoresis, and electroblotting was carried out as described previously (see, e.g.; Chaib H, et al., 2001 Cancer Res. 61, 2390-2394; incorporated herein by reference in its entirety). Proteins were detected using antibodies against phospho-ERK½ (Cell Signaling #9101), total ERK½ (Cell Signaling #9102), CXCR4 (Abcam #ab2074), Elk-1 (Cell Signaling #9182), Phospho Elk-1 (Cell Signaling #9181), or beta-actin (Santa Cruz #sc-1615), in conjunction with an ECL detection system.

Statistical Analysis. Normalized array acquired transcript expression values were analyzed using a t-statistic test and by calculation of fold change between data sets. Genes that exhibited both a large t-statistic (>10.0) and a large fold change (>2.0) were considered to be differentially expressed. All other data was assessed by t-test or analysis of variance with $p<0.05$ considered statistically significant.

EXAMPLE XII

This example shows that CXCL12/CXCR4-mediated stimulation of cellular proliferation is ERK dependent. The stimulation of N15C6 and LNCaP cells with low, picomolar levels of CXCL12 induces cellular proliferation (see, e.g., Examples I-VI). Pre-treatment of the cells with antibody against the CXCL12 receptor, CXCR4, ablates the proliferative response, whereas pre-treatment with an isotype antibody does not (see FIG. 14A). These results indicate that CXCL12-stimulated cellular proliferation is specifically mediated through interactions with the CXCR4 receptor.

Figure 14:
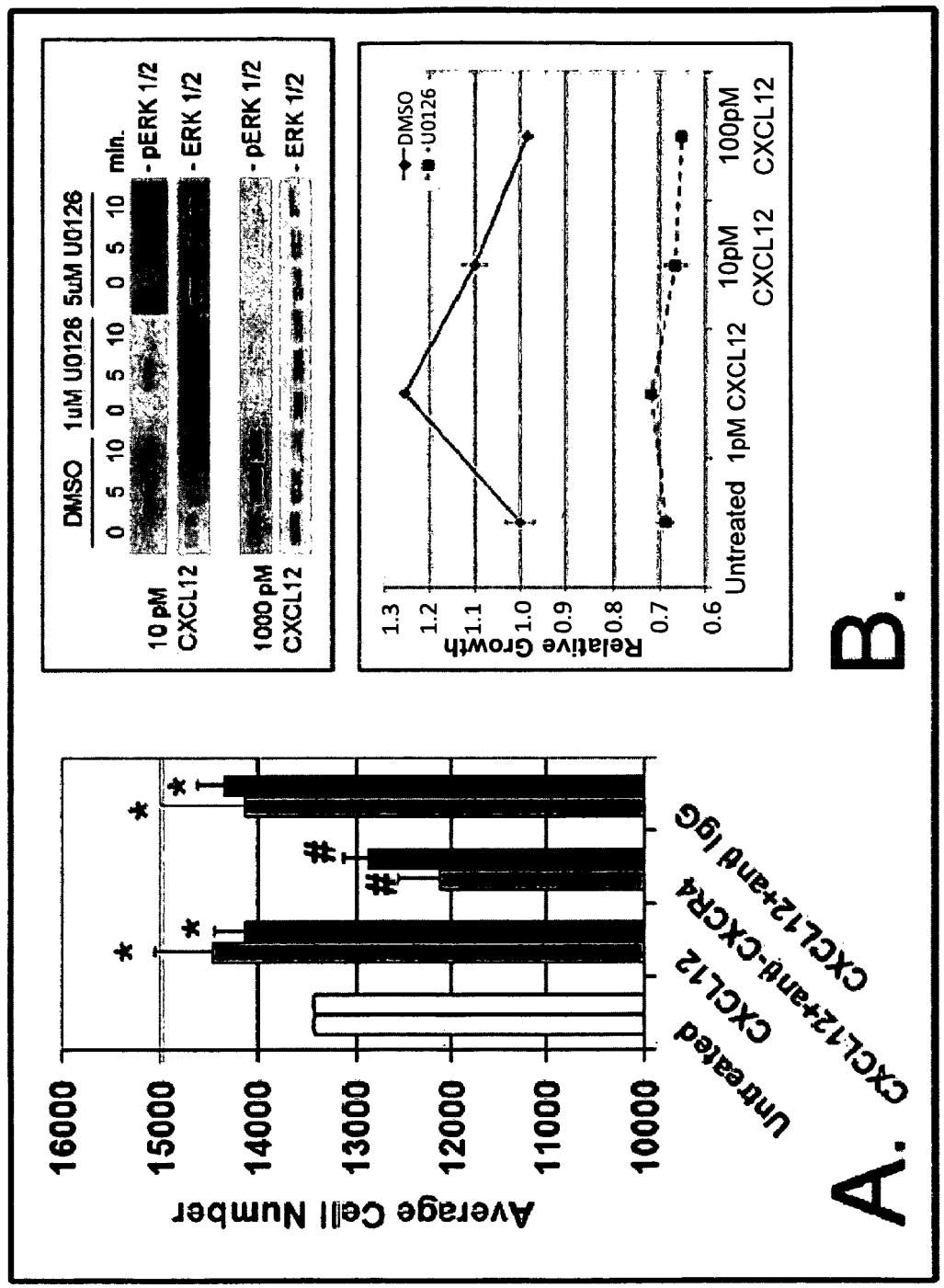
FIG. 14 shows CXCL12-mediated cellular proliferation is CXCR4-specific and ERK-dependent. 14A: N15C6 prostate epithelial cells grown for 96 hours in serum-free HIE media supplemented with 1 pM CXCL12 (gray bars) or 10 pM CXCL12 (black bars) proliferated to higher levels when compared to growth in serum-free HIE media alone (white bars) ($p<0.001$, indicated by *). Pre-incubation of cells for one hour with 1 ug/ml anti-CXCR4 antibody followed by supplementation with CXCL12 and maintenance of growth in CXCL12+anti-CXCR4-containing media significantly ablated the proliferative response ($p<0.001$, indicated by #). Cellular growth following pre-incubation with 1 ug/ml anti-IgG control followed by supplementation with CXCL12 and maintenance of growth in CXCL12+anti-IgG control-containing media was similar to that observed for growth in CXCL12-supplemented media and was significantly higher than control ($p<0.001$, indicated by *). 14B—TOP: N15C6 cells grown in SF HIE media, pre-treated for 2 hours with the solvent control DMSO, then supplemented with 10 pM or 1000 pM CXCL12 demonstrate rapid and transient ERK ½ phosphorylation at 5 and 10 minutes post-stimulation compared to cells at the initiation of the experiment (time 0). Pre-treatment of the cells the MEK1 inhibitor, U0126, either reduces (1 uM) or ablates (5 uM) ERK ½ phosphorylation. 14B—BOTTOM: N15C6 cells grown in SF HIE pre-treated for 2 hours with the solvent control DMSO or 5 uM U0126, then supplemented with 1, 10, or 1000 pM CXCL12 and maintained in that media with DMSO or U0126 demonstrated growth above control at 1 pM and 10 pM CXCL12 in DMSO, which was ablated in the presence of U0126.

The Ras-mediated ERK pathway is a major downstream signaling pathway that is both activated by CXCL12/CXCR4 interactions and known to stimulate cellular proliferation. Experiments conducted during the course of the present invention showed that stimulation of N15C6 cells to 1 pM, 10 pM or 1000 pM CXCL12 induced rapid, transient extracellular regulated kinase (ERK ½) phosphorylation and activation. ERK ½ phosphorylation and activation has also been shown in LNCaP cells treated with CXCL12 (see, e.g., Wang J, et al., 2005 Cellular Signalling 17:1578-1592; incorporated herein by reference in its entirety). Whether ERK activation was required for CXCL1/CXCR4-mediated cellular proliferation was tested. To accomplish this, the MEK the mitogen-activated protein kinase 1 (MEK1) inhibitor, U0126, was utilized to inhibit the ability of MEK1 to phosphorylate ERK ½, thus preventing ERK activation. As seen in FIG. 14B, treatment of N15C6 cells with 1 pM CXCL12 and the U0126 vehicle, DMSO, resulted in rapid and transient MEK1-mediated ERK ½ phosphorylation. Co-treatment of the cells with 1 pM CXCL12 and 0.1 uM or 1.0 uM U0126 diminished ERK ½ phosphorylation. Moreover, the proliferative response of N15C6 cells to CXCL12 was nearly ablated when the cells were co-treated with 1 pM, 10 pM or 100 pM CXCL12 and 1.0 uM U0126 compared to cotreatment with DMSO (FIG. 14B). Treatment with U0126 also diminished N15C6 cellular proliferation in the absence of CXCL12, suggesting that both ERK-dependent and ERK-independent mechanisms regulate cellular proliferation in these cells (FIG. 14B).

EXAMPLE XIII

Figure 15:
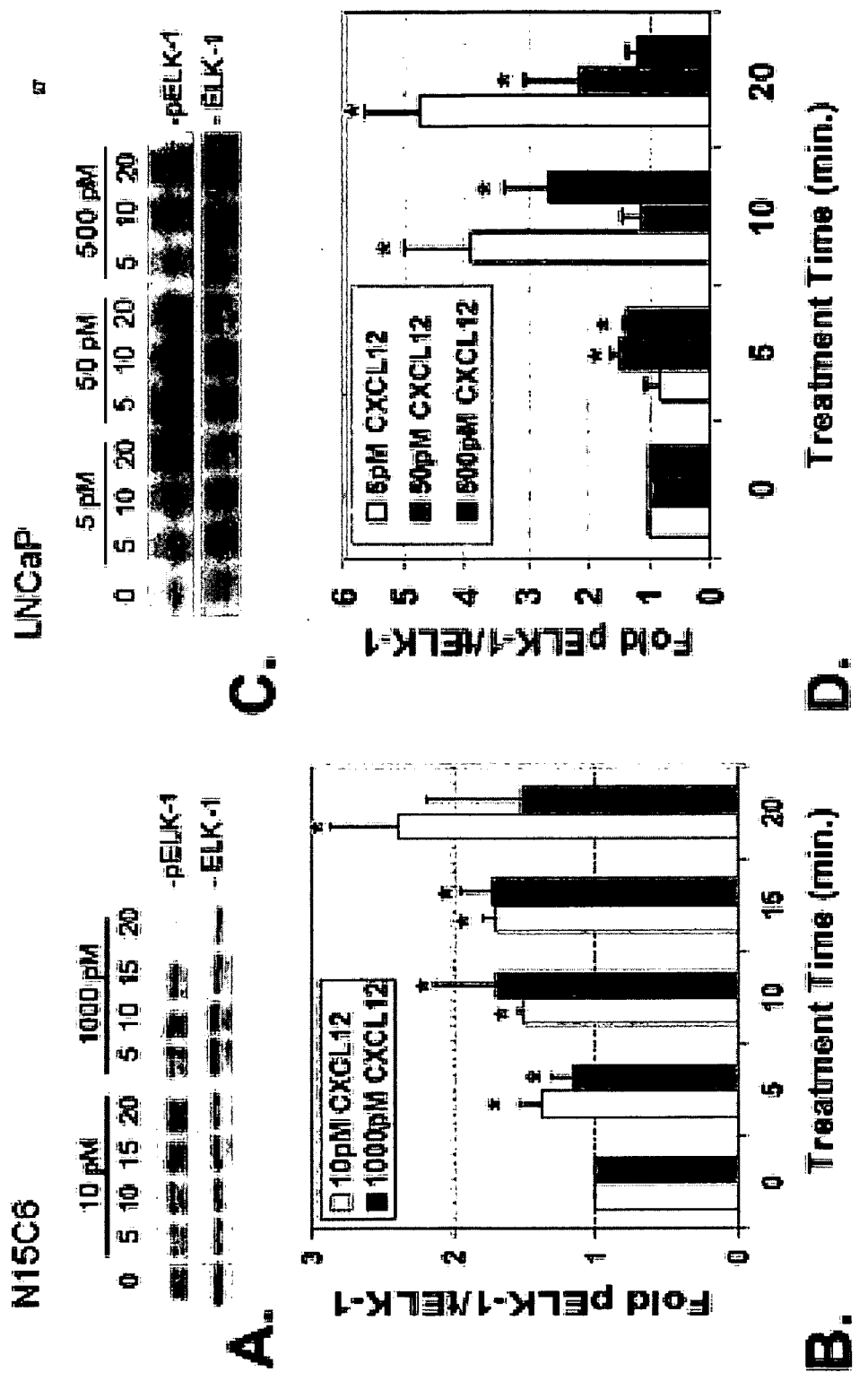
FIG. 15 shows CXCL12 mediates the activation of ELK-1. N15C6 cells demonstrate rapid and transient phosphorylation of the ELK-1 transcription factor after exposure to 10 pM or 1000 pM CXCL12. LNCaP cells demonstrate the same after exposure to 5 pM, 50 pM, or 500 pM CXCL12. Densitometry plot of the immunoblots demonstrate phosphorylation of ELK-1 relative to total ELK-1 (p/ELK-1/tELK-1). All values are normalized to those obtained for the 0 time point, which was set at 1-fold for comparative purposes. Phosphorylation levels significantly higher than that those observed at time 0 are indicated by * ($p<0.05$). Densitometry plot of the immunoblots demonstrate phosphorylation of ELK-1 relative to total ELK-1 (p/ELK-1/tELK-1). All values are normalized to those obtained for the 0 time point, which was set at 1-fold for comparative purposes. Phosphorylation levels significantly higher than that those observed at time 0 are indicated by * ($p<0.05$).
Figures 16A, 16B:
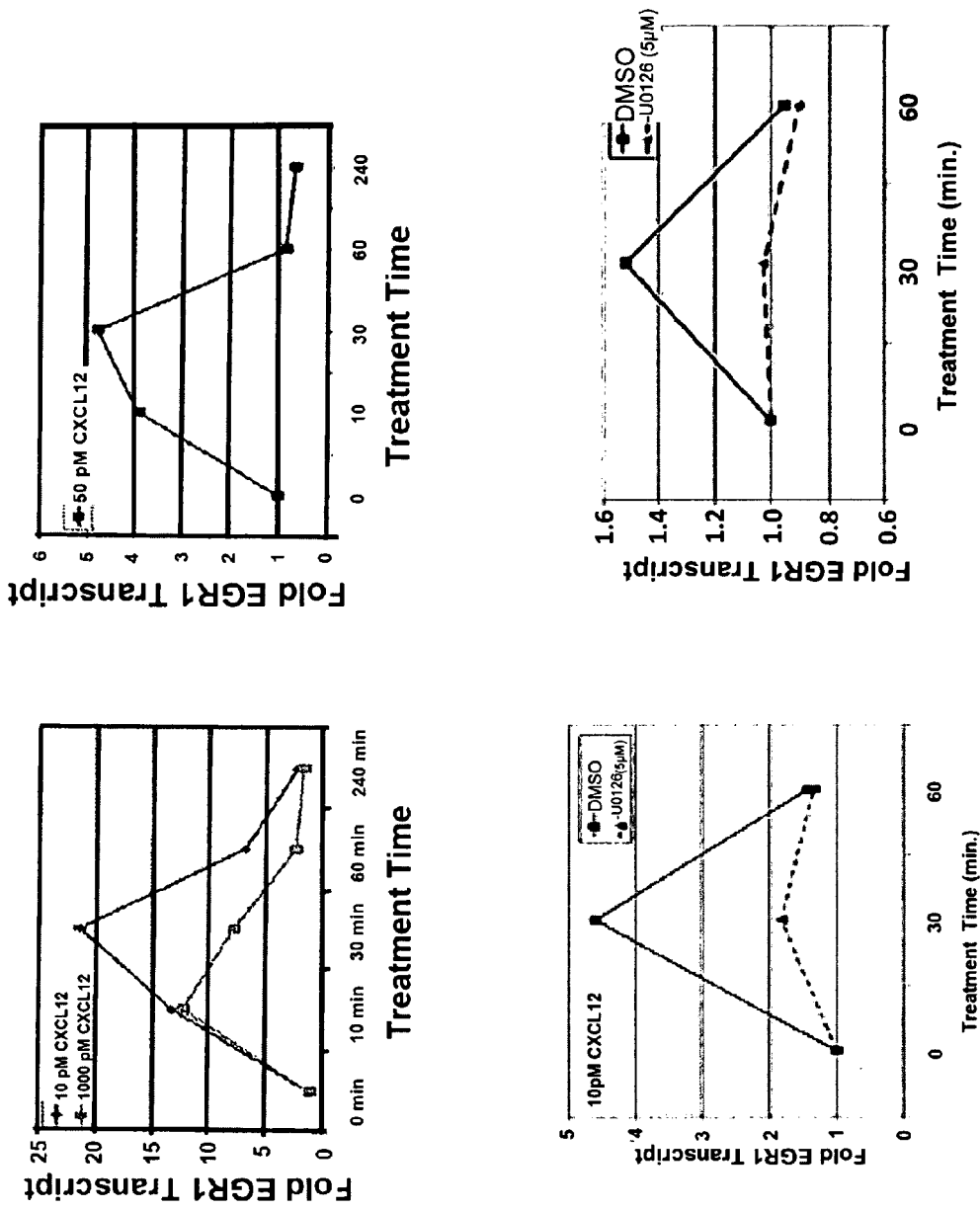
FIG. 16 shows CXCL12-mediated EGR1 transcription is ERK-dependent. 16A: N15C6 cells treated with 10 pM or 1000 pM CXCL12, or LNCaP cells treated with 50 μM CXCL12, rapidly and robustly transcribe the EGR1 gene. The transcriptional response in N15C6 cells is more robust and the lower concentration of CXCL12, similar to that which induces a proliferative response. 16B: N15C6 cells treated with 10 pM CXCL12 or LNCaP cells treated with 50 pM CXCL12 rapidly transcribe the EGR1 gene, though the response is dampened when pretreated for 2 hours with the solvent control, DMSO. Pre-treatment of the cells for 2 hours with 5 uM U0126 further dampens (N15C6 cells) or ablates (LNCaP cells) CXCL12-stimulated EGR1 transcription. 16C: Quantitative real-time PCR of RNA purified from N15C6 cells pre-treated with 0.05% DMSO then treated with 10 pM CXCL12 (black triangles) or LNCaP cells pre-treated with 0.05% DMSO then treated with 50 pM CXCL12 (black squares) demonstrates rapid and robust transcription of the EGR1 gene ($p<0.001$, indicated by *). This response is significantly dampened when the cells are first pretreated for 2 hours with 5 uM U0126 in 0.05% DMSO (N15C6 cells, white triangles; LNCaP cells, white squares) ($p<0.001$, indicated by #). 16D: Quantitative real-time PCR of RNA purified from N15C6 cells treated for 30 minutes with 10 pM CXCL12 or LNCaP cells treated with 50 pM CXCL12 (black bars) demonstrates a robust and significant accumulation of transcript from the EGFR gene ($p<0.001$, indicated by *) and a significant decrease in transcription of the ERBB2 gene ($p<0.05$, indicated by #) compared to treated cells at 0 minutes (grey bars), parallel to RNA profiling results obtained using Affymetrix GeneChips.
Figure 16:
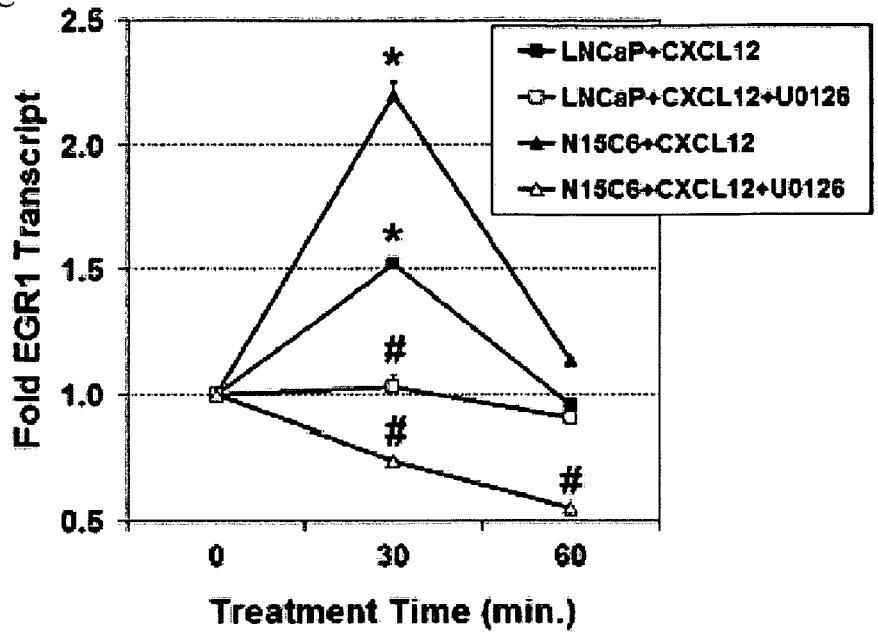
Figure 16:
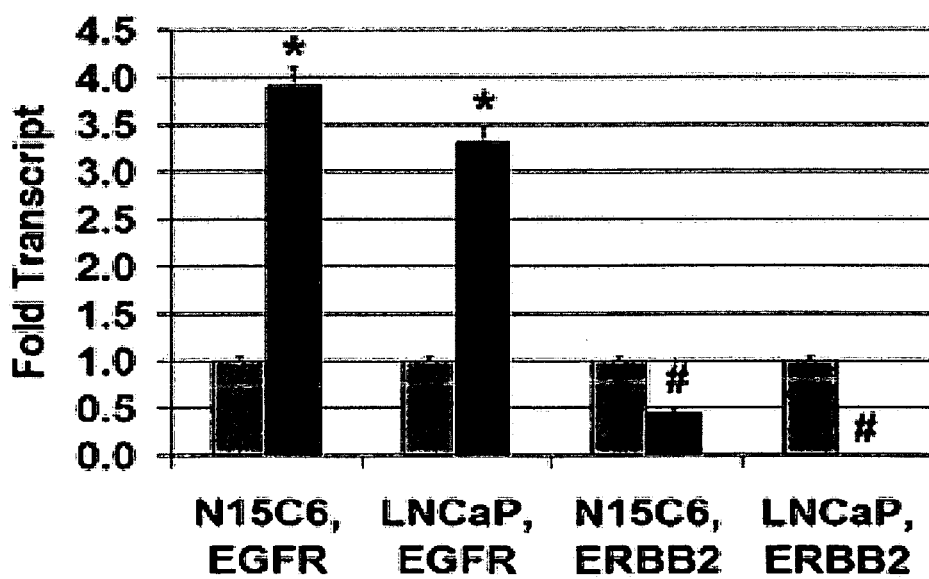

This example shows CXCL12/CXCR4-mediated signaling activates Elk-1 and promotes EGR1 gene transcription. N15C6 and LNCaP cells were next examined for activation of Elk-1, an Ets domaintype transcription factor and immediate downstream effector of activated ERK ½, consequent to CXCL12-stimulated ERK ½ activation. N15C6 or LNCaP prostate epithelial cells stimulated with 1-1000 pM CXCL12 demonstrated rapid and transient phosphorylation of Elk-1 (FIG. 15). Elk-1 is a transcriptional activator of the Early Growth Response 1 (EGR1) gene, which encodes a $C_2H_2$-type zinc-finger protein that is induced by mitogenic stimulation and has been shown to stimulate tumor cell growth, play a role in tumor progression, and stimulate angiogenesis and improved survival of tumor cells (see, e.g., Adamson E D, et al., 2002 Tumour Biol. 23:93-102; incorporated herein by reference in its entirety). Quantitative RT-PCR assays performed at 0, 10, 30 and 60 minutes post-stimulation showed that N15C6 and LNCaP cells stimulated with CXCL12 rapidly and robustly accumulated EGR1 gene transcript (FIG. 16A). Low, picomolar levels of CXCL12 similar to those previously observed to promote N15C6 and LNCaP cellular proliferation stimulated the transcription of EGR1 transcript at levels fivefold (LNCaP cells) to 20-fold (N15C6 cells) above those observed for unstimulated cells. Treatment of N15C6 cells with higher, nanomolar, levels of CXCL12 resulted in lower EGR1 transcript levels than those achieved using 10 pM CXCL12 (FIG. 16A).

EXAMPLE XIV

This example shows CXCL12/CXCR4-mediated EGR1 gene transcription is ERK-dependent. The specificity of the EGR1 gene transcriptional response to CXCL12/CXCR4-mediated ERK signaling was next examined using the mitogen-activated protein kinase kinase 1 (MEK1) inhibitor, U0126. For these experiments, cells were plated at 50,000 cells/well in triplicate, treated with U0126 (Cell Signaling) at 5 uM or with DMSO for 2 hours, then stimulated for one hour with CXCL12 at concentrations shown previously to induce EGR1 gene transcription, e.g., 10 pM CXCL12 for N15C6 cells and 50 pM CXCL12 for LNCaP cells. As seen in FIGS. 16B and 16C, pre-treatment with the MEK1 inhibitor ablated the EGR1 gene transcriptional response to CXCL12 stimulation for both N15C6 and LNCaP cells, showing that ERK activation is required for CXCR4/CXCL12-mediated EGR1 gene transcription.

EXAMPLE XV

This example shows CXCL12 stimulates a global transcriptional response in prostate epithelial cells that is partially ERK-dependent. Both N15C6 and LNCaP cells respond proliferatively to low, picomolar levels of CXCL12, similar to levels of CXCL12 secreted by aging human prostate stromal fibroblasts. The observation that these same levels of CXCL12 stimulated downstream ERK ½ and ELK1 activation and EGR1 gene transcription raised the possibility that other genes may also be transcribed in response to CXCL12 stimulation. To explore this possibility, N15C6 and LNCaP cells were treated in replicate with CXCL12 and the MEK1 inhibitor, U0126, CXCL12 and DMSO (the vehicle control for U0126), or DMSO alone for 60 minutes. The cells were immediately pelleted, lysed and purified RNA was subjected to gene expression profiling using Affymetrix Human Genome U133 Plus 2.0 Arrays. In N15C6 cells, 370 genes were identified as upregulated and 162 genes as down-regulated at significance levels of p<0.005 and fold levels >1.5 consequent to stimulation with 10 pM CXCL12. In LNCaP cells, 185 genes were identified as up-regulated and 413 genes as down-regulated consequent to stimulation with 50 pM CXCL12 (see Table 1).

TABLE I

Summary of CXCL12-Regulated Transcriptional Response in N15C6 and LNCaP Cells

|  | UP-REGULATED | DOWN-REGULATED |
|---|---|---|
| N15C6 Response to CXCL12 | 370 | 162 |
| N15C6 Response to CXCL12 + U0126 | 29 | 296 |
| LNCaP Response to CXCL12 | 185 | 413 |
| LNCaP Response to CXCL12 + U0126 | 13 | 26 |

These results show that both cellular proliferation and gene transcription are induced in N15C6 and LNCaP prostate epithelial cells stimulated with CXCL12 at concentrations equivalent to those secreted by aging prostate stromal fibroblasts.

In total, 85 genes were differentially transcribed in common by N15C6 and LNCaP cells following CXCL12 stimulation (see Table II).

TABLE II

Genes Commonly Transcriptionally Regulated by CXCL12 in N15C6 and LNCaP Cells

PROMOTING EFFECT ON CELLULAR PROLIFERATION/TUMOR METASTASIS

DOWN-REGULATED GENES

| | |
|---|---|
| CDH1 | impairs cell-cell adhesion |
| CTNN81 | impairs cell-cell adhesion |
| CPSF1 | impairs cell-cell adhesion |
| EXOSC8 | impairs cell-cell adhesion |
| ITG84 | impairs cell-cell adhesion |
| LOXL2 | impairs cell-cell adhesion |
| GSR | impairs cell-cell adhesion |

TABLE II-continued

Genes Commonly Transcriptionally Regulated by CXCL12 in N15C6 and LNCaP Cells

PROMOTING EFFECT ON CELLULAR PROLIFERATION/TUMOR METASTASIS

| | |
|---|---|
| RANGAP1 | impairs formation of mitotic spinde, disrupts normal cell division |
| NUMA1 | impairs formation of mitotic spinde, disrupts normal cell division |
| RBM14 | impairs DNA repair, facilitates mutation |
| BMP1 | impairs basement membrane assembly |
| ERBB2 | Expression is associated with apoptosis in prostate and colon tumors |
| MAPRE3 | facilitates cell motility |
| DOCK9 | facilitates (?) cell mobility |
| ARPC4 | facilitates (?) cell mobility |
| MARCK8 | facilitates (?) cell mobility |
| TP53 | promotes progression through cell cycle |
| MAFK | promotes progression through cell cycle |
| CUGSP1 | promotes progression through cell cycle |
| CDK2 | promotes progression through cell cycle |
| CDK9 | promotes progression through cell cycle |
| HPK3 | promotes resistance to apoptosis |
| MAPKBP2 | promotes resistance to apoptosis |
| CANX | promotes resistance to apoptosis |
| NR2F6 | impares transcriptional repression |
| UNCLEAR | STAT2, LAMP1, AP3D1, FEX5, SLC16A, TNPO2, EHMT1, IPO8, MTMR1, PTBP1, THOC4, AR52, DNAJC14, BNS, LS5, NADK, GLT2501, UNC130, REPN1 |
| UNKNOWN | TM95F4, CDCP1, FLJ20273, FNDG5, WDR6, WOR76, UBE38 |

UP-REGULATED GENES

| | |
|---|---|
| EGFR | potentially upregulates cell proliferation |
| CD44 | promotes resistance to apoptosis; metastasis repressor in prostate cancer |
| ANXRD12 | amplified in same retinoblastomas |
| SSBP1 | associated with transcriptional up regulation |
| CCNT1 | controls HIV transcript elongation (with CDK9) |
| JMJD1C | family members amplified in some cancers |
| HNRPD | involved in post-transcriptional regulation of early response genes |
| GOPC | may upregulate Rho GTPase activity |
| STRAP | overexpression activates mitogen-activated protein kinase, prmotes anchorage, independent growth on the cells, frequently overexpressed in human breast tumors |
| DYX1C1 | transcritonally regulated by ELK1 |
| UNCLEAR | FNBP4, FRP52, EIF358, RPL38, LMOT |
| UNKNOWN | RFM27, CRBN, NUPL2, ANF038, PIK3C2A, 2NF567, FLJ22028, PITPNB, BAT201, CEF350, FAM44A, KIAA0256, KLHLB, LOG554203, NFKBR, THAP6, TM201 |

The use of both the Gene Ontology and Information Hyperlinked over Proteins (iHOP) databases permitted a limited functional assessment of proteins encoded by genes transcriptionally down-or up-regulated consequent to CXCL12 stimulation (see, e.g., Hoffmann, R., et al., 2004 Nature Genetics 36, 664; incorporated herein by reference in its entirety). This assessment showed that the predicted functional consequences of loss of expression for many of the proteins encoded by the 52 commonly downregulated genes was consistent with promoting cellular proliferation or tumor progression. In particular, the transcriptional down-regulation of several genes encoding proteins that normally promote cell cycle arrest, including TP53, MAFK, CUGBP1, CDK2 and CDK9 or resistance to apoptosis, e.g., HIPK3, MAPK8IP2 and CANX, by CXCL12 may functionally promote cellular proliferation. Similarly, the observed transcriptional down-regulation of gene encoding proteins involved in cell-cell adhesion, including CDH1, CTNNB1, CPSF1, EXOSC6, ITGB4, LOXL2, and SORBS3, or of genes involved in cytoskeleton organization, including MAPRE3, DOCK9, ARPC4, and MARCKS, could facilitate cellular motility, a trait associated with tumor progression and metastasis. The predicted increased expression of proteins encoded by the 33 genes upregulated consequent to CXCL12 stimulation that may promote cellular proliferation or tumor progression included EGFR, CD44, and STRAP, which have been found up-regulated in many tumor types and are functionally involved in cellular proliferation and tumor metastasis. Quantitative real-time PCR of RNA purified from N15C6 or LNCaP cells treated for 30 minutes with CXCL12 demonstrates a robust and significant accumulation of transcript from the EGFR gene and a significant decrease in transcription of the ERBB2 gene compared to treated cells at 0 minutes, parallel to RNA profiling results obtained using Affymetrix GeneChips (see FIG. 3D and Table II).

Co-treatment of N15C6 or LNCaP cells with CXCL12 and 1 uM U0126 reduced the number of differentially expressed genes in both cell lines compared to treatment with CXCL12 alone (Table I). The number of genes transcriptionally up-regulated consequent to CXCL12 decreased in genes in both cell lines, to 29 for N15C6 and 13 for LNCaP cells. This showed that transcriptional activation in both cell lines consequent to CXCL12 stimulation was largely ERKdependent. Inhibition of ERK activation also altered the number and composition of genes transcriptionally down-regulated consequent to CXCL12 treatment, with 296 genes in N15C6 cells and 26 genes in LNCaP cells downregulated (see, Table III).

TABLE III

Common N15C6 qand LNCaP Transcriptional Response to CXCL12 + U0126

| | Function | Transcriptional Regulation |
|---|---|---|
| Up-Regulated Genes | | |
| ITGB4 | MULTIPLE: cell communication, cell adhesion signaling | via Ets- and NFkB-binding site motifs in promoter |
| Down-Regulated Genes | | |
| CD44 | cell-cell adhesion | EGR1 via activated ERK 1/2 |
| EGR1 | transcription | activated ERK 1/2 |
| IL8 | MULTIPLE: angiogenesis cell motility, chemotaxis, cell cycle arrest, signaling, inflammatoryimmune response | activated ERK 1/2, NFkB, p38, and other transcription factors |
| MAFF | transcription | inflammatory cytokines |
| TXNIP | keratinocyte differentiation | via E-box motifs in promoter |
| ARRDC4 | UNKNOWN | UNKNOWN |

Seven of the 39 genes affected transcriptionally by the treatment of LNCaP cells with both CXCL12 and U0126 were similarly affected in N15C6 cells, including ITGB4 (up-regulated) and CD44, EGR1, IL8, MAFF, TXNIP and ARRDC4 (down-regulated). Reports in the literature suggested that the majority of these genes were potentially regulated by ERK ½ (ITGB4, CD44, EGR1, IL8) or inflammatory cytokines (MAFF) (see, e.g., Hoffmann, R., et al., 2004 Nature Genetics 36, 664; incorporated herein by reference in its entirety).

Figure 17:
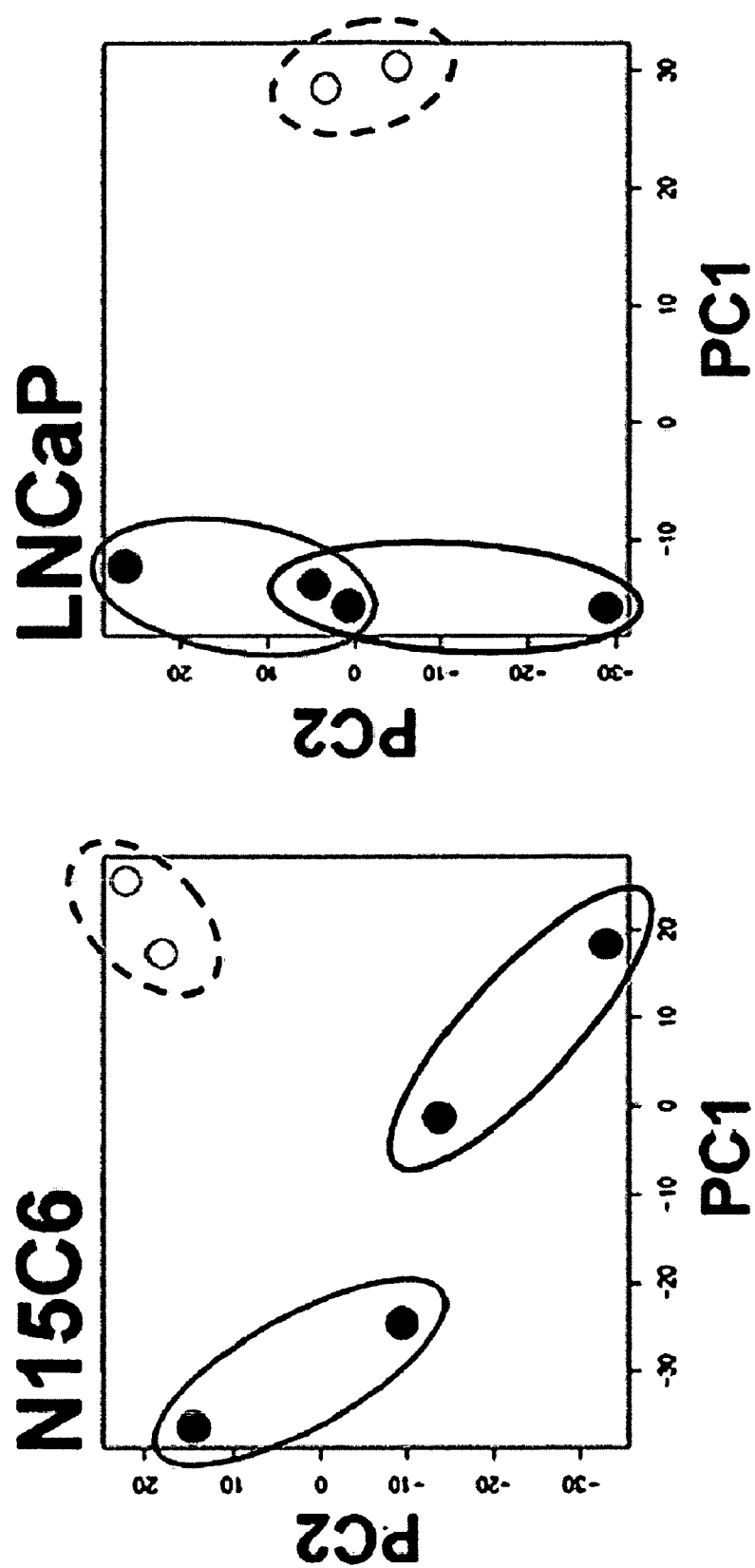
FIG. 17 shows Principal Components Analysis of CXCL12-stimulated Transcriptional Response. The transcriptional response of N15C6 or LNCaP cells in SF HIE media 30 minutes after a 2 hour pre-treatment with the solvent control DMSO (white dots, dotted ovals), the same but pre-treated with DMSO and stimulated with 10 pM (N15C6) or 50 pM (LNCaP) CXCL12 (black dots, black ovals) or pre-treated with 5 uM U0126 and stimulated with 10 pM (N15C6) or 50 pM (LNCaP) CXCL12 (grey dots, grey ovals) is represented along two components. Each experiment was performed twice, and both sets of data are shown. The significant separation between the transcriptional responses resulting from DMSO− and DMSO+CXCL12 treatments demonstrates that CXCL12 induces a robust transcriptional response in both cell lines. The separation between the transcriptional responses resulting from DMSO+CXCL12 and U0126+CXCL12 treatments is greater for N15C6 than for LNCaP cells, suggesting that the CXCL12-mediated transcriptional response is more ERK-dependent for N15C6 than LNCaP cells.

A principal components analysis (PCA) of the gene expression profiling data showed that DMSO—treated and CXCL12+DMSO-treated cells are widely separated along the first two principal components, consistent with the observed robust CXCL12-stimulated transcriptional response exhibited by both N15C6 and LNCaP cells (see FIG. 17). Although the gene expression profiles of CXCL12+DMSO- and U0126+DMSO-treated N15C6 cells are also distinctly separated in the PCA plot, those of similarly treated LNCaP cells demonstrate considerable overlap along the first principal component (PC1) and some overlap along the second principal component (PC2) (FIG. 17). This analysis is consistent with the observation that the CXCL12-stimulated transcriptional response in N15C6 cells may be more ERK-dependent than that observed for LNCaP cells.

EXAMPLE XVI

This example shows that CXCL5 and CXCL12 are detectable at high levels in the serum of men with BPH and prostatitis. Experiments conducted during the development of embodiments for the present invention show that CXC-type chemokines (e.g., CXCL1, CXCL5, CXCL6, and CXCL12) are secreted at higher levels by aging human prostate stromal fibroblasts (see, e.g., FIGS. 6A, 6B, and 6C). In particular, experiments were conducted to determine whether specific CXC-type chemokines are differentially detectable in the serum of men with benign and malignant prostatic disease. Althought the subjects exhibited detectable PSA values and underwent diagnostic prostate needle biopsies, only ~30% of patients enrolled in the study were diagnosed with prostate cancer. Moreover, information relevant for the diagnosis of non-cancer prostate disease, e.g., prostate volume (for BPH), histologic evidence of acute inflammation on biopsy (for prostatitis), and AUASI (for lower urinary tract symptoms), was available for these patients.

Figure 18:
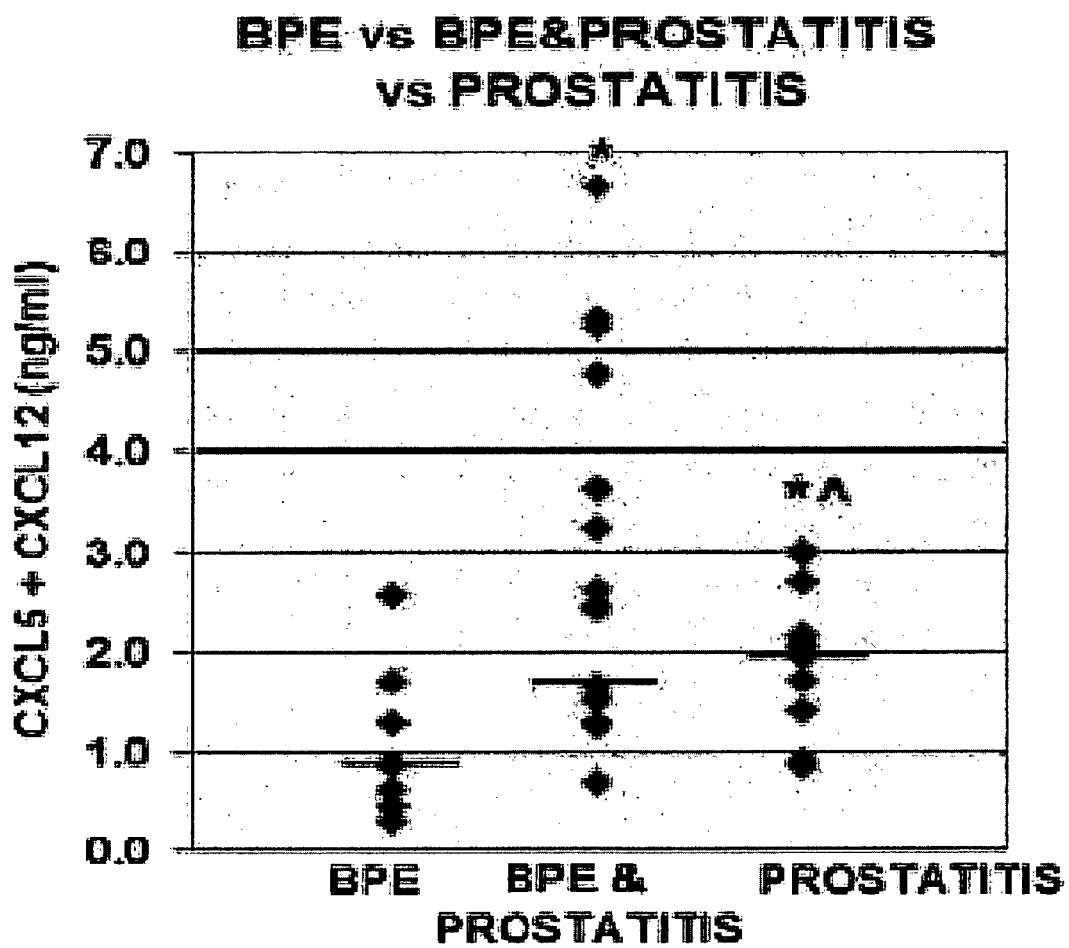
FIGS. 18A and 18B show that CXC-type serum chemokines distinguish between BPH, prostatitis, and cancer. 18A: Combinatorial serum levels of CXCL5 and CXCL12 were shown to distinguish between BPH and concurrent BPH+prostatitis (*) or between BPH and prostatitis (*^) in patients without prostate cancer. 18B: Combinatorial serum levels of CXCL5 and CXCL12 (black) significantly distinguish between BPH and cancer (*) among men with serum PSA values of 0.1-10 ng/ml. Serum levels of CXCL5 (white) and CXCL12 (gray) are also shown. In both FIGS. 18A and 18B, median values for CXCL5+CXCL12 are indicated by a black horizontal bar.
Figure 18:
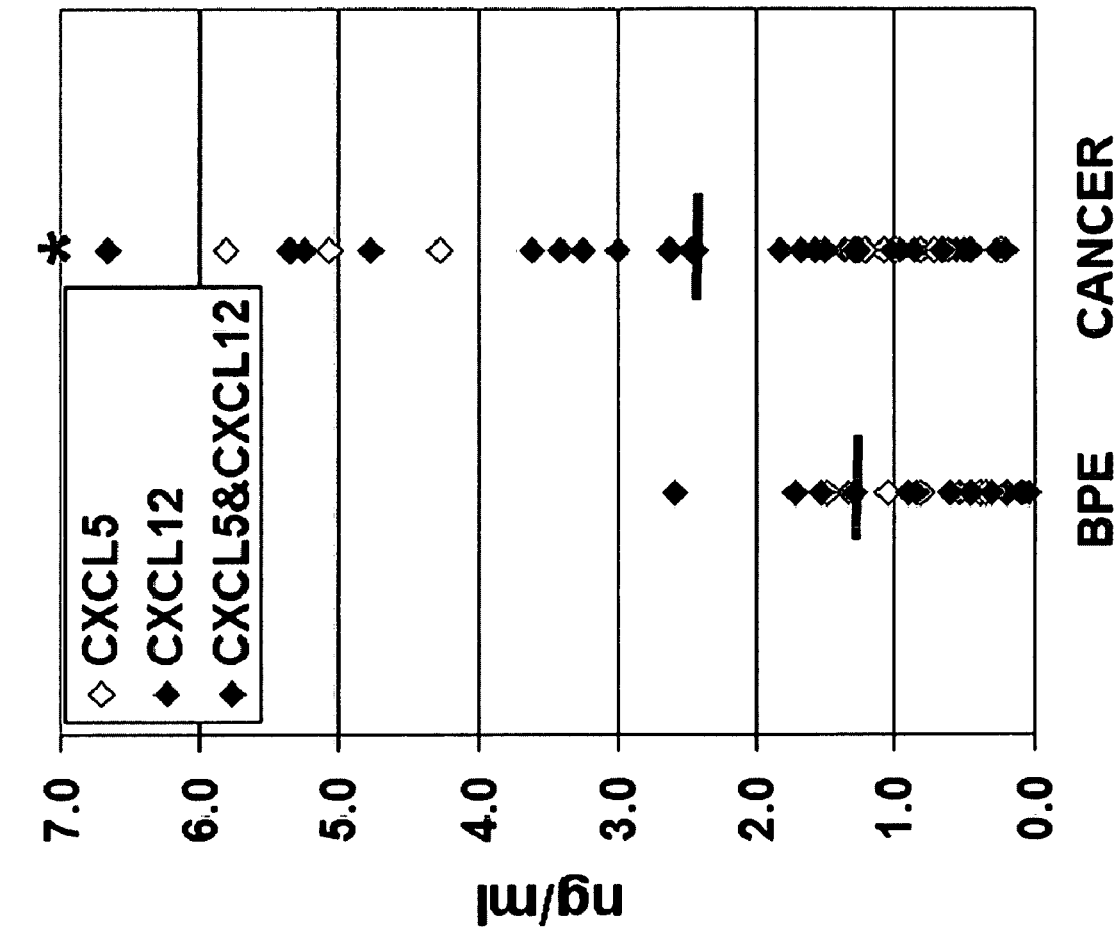

As shown in FIG. 18A a survey of serum from 30 subjects without cancer indicated that men with BPH alone demonstrated significantly lower levels of combinatorial CXCL5+CXCL12 chemokine levels than men with concurrent BPH and prostatitis. In addition, combinatorial serum CXCL5+CXCL12 chemokine levels distinguished between BPH alone or prostatitis alone. These results indicate that serum chemokine levels provide a serum-based, non-invasive test for differential diagnosis of BPH or prostatitis.

As shown in FIG. 18B, combinatorial serum CXCL5+CXCL12 chemokine levels distinguished between men with BPH or cancer who exhibited serum PSA values in the 'gray' 0.1-10 ng/ml range. These results indicate that serum chemokine levels provide a serum-based, non-invasive test for differential diagnosis of BPH or cancer among men with low but detectable serum PSA values.

EXAMPLE XVII

Figure 19:
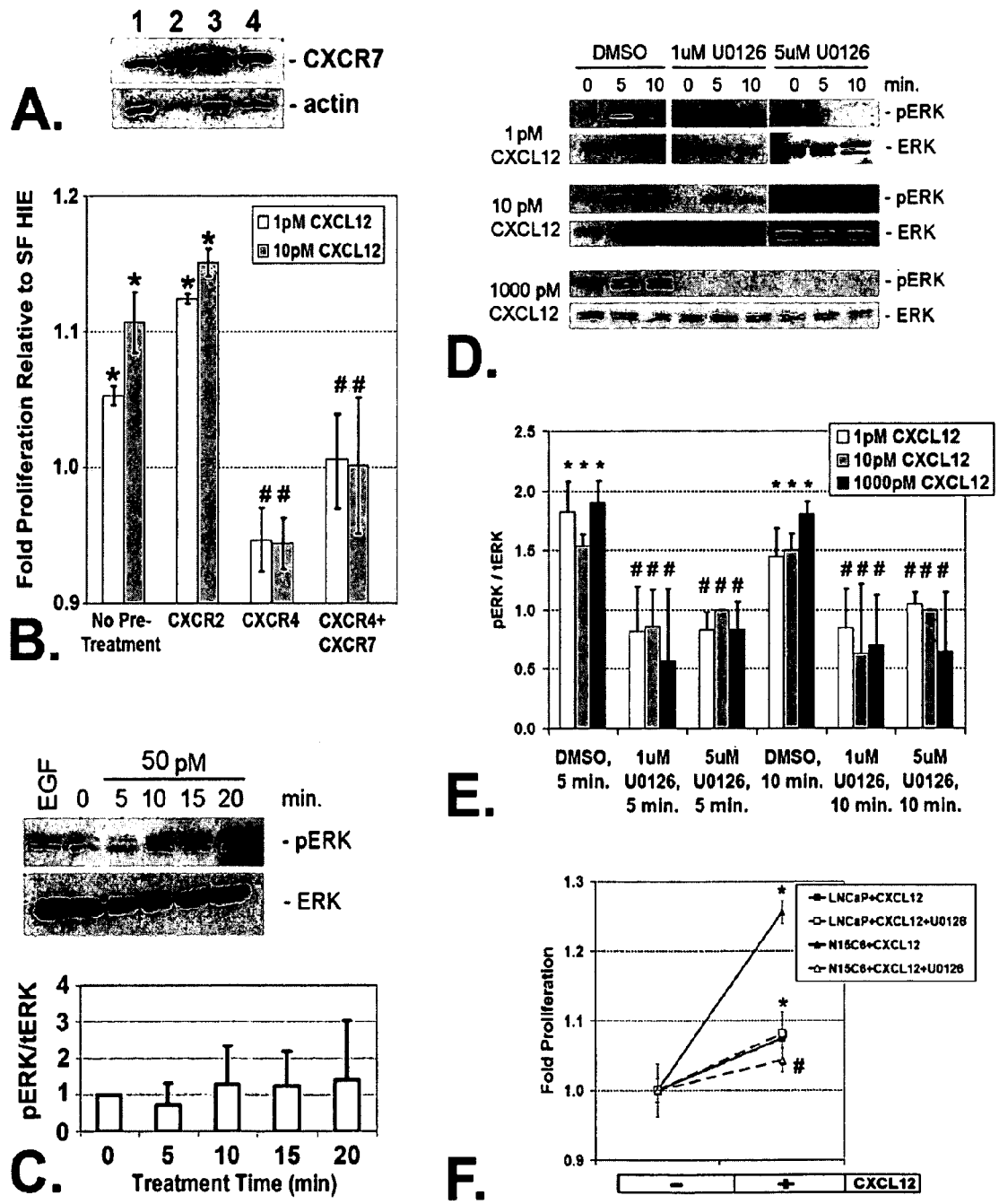
FIG. 19 shows receptor-specificity and ERK-dependence of CXCL12-mediated cellular proliferation. 19A. Immunoblot demonstrating that PC3 (lane 1), LNCaP (lane 2), N15C6 (lane 3) and BPH-1 (lane 4) prostate epithelial cells abundantly express CXCR7 (aka RDC1), a receptor that binds CXCL12. The primary antibody concentrations used were 1:1000 for CXCR7 and 1:5000 for actin (as loading control). 19B. N15C6 prostate epithelial cells grown for 96 hours in serum-free HIE media supplemented with 1 pM CXCL12 (white bars) or 10 pM CXCL12 (gray bars) proliferated to significantly higher levels than cells grown in serum-free HIE media alone ($p<0.001$, indicated by *). Cellular growth following pre-incubation with an antibody against an unrelated chemokine receptor, CXCR2, followed by supplementation with CXCL12 and maintenance of growth in CXCL12+anti-CXCR2-containing media was similar to that observed for non-pre-treated cells grown in CXCL12-supplemented media and was significantly higher than that in serum-free HIE media alone ($p<0.001$, indicated by *). Pre-incubation of cells for one hour with 1 ug/ml antibody against CXCR4, a receptor for CXCL12, followed by supplementation with CXCL12 and maintenance of growth in CXCL12+anti-CXCR4-containing media significantly ablated the proliferative response ($p<0.001$, indicated by #). Pre-incubation of cells for one hour with 1 ug/ml antibodies against both known receptor for CXCL12, CXCR4 and CXCR7, followed by supplementation with CXCL12 and maintenance of growth in CXCL12+anti-CXCR4/CXCR7-containing media also significantly ablated the proliferative response ($p<0.001$, indicated by #) though not significantly more so than that obtained upon pre-treatment with anti-CXCR4 alone. All data is shown normalized to growth in un-supplemented SF HIE media, which was set at 1-fold. 19C. LNCaP cells demonstrate minimal ERK phosphorylation (pERK) upon treatment with 100 ng/ml epidermal growth factor (EGF) or 50 µM CXCL12. Primary antibody concentrations used were 1:500 for phosphoERK and 1:2000 for total ERK. Phosphorylation of ERK relative to total ERK quantitated from the immunoblot is shown in the densitometry plot as pERK/tERK. 19D. N15C6 cells grown in SF HIE media, pre-treated for 2 hours with the solvent control 0.05% DMSO, then supplemented with 1, 10, or 1000 pM CXCL12 demonstrate rapid and transient ERK phosphorylation (pERK) at 5 and 10 minutes post-stimulation compared to cells at the initiation of the experiment (time 0). Pre-treatment of the cells the MEK1 inhibitor, U0126 (dissolved in 0.05% DMSO), either reduces (1 uM) or ablates (5 uM) ERK phosphorylation. Primary antibody concentrations used were as described in 19B. 19E. Densitometry plot of the immunoblots shown in C demonstrates phosphorylation of ERK relative to total ERK (pERK/tERK). All values are normalized to those obtained for the 0 time point, which was considered 1-fold for comparative purposes. Cells pre-treated with 0.05% DMSO then treated with 1, 10, or 1000 pM CXCL12 for 5 or 10 minutes demonstrated significantly higher levels of ERK phosphorylation than those at time 0 ($p<0.001$, indicated by *). Cells pre-treated with 1 uM or 5 uM U0126 in 0.05% DMSO then treated with 1, 10, or 1000 pM CXCL12 for 5 or 10 minutes demonstrated levels of ERK phosphorylation at or below those obtained at time 0 ($p<0.001$, indicated by #). 19F. N15C6 cells (black triangles) grown in SF HIE with 0.05% DMSO+10 pM CXCL12 (+) proliferated significantly better than those grown in SF HIE with 0.05% DMSO (−) ($p<0.001$, indicated by *). Proliferation was significantly reduced in N15C6 cells (white triangles) grown under the same conditions but with the addition of 5 uM U0126 ($p<0.001$, indicated by #). LNCaP cells treated in a similar manner but supplemented with 50 pM CXCL12 did not demonstrate significant differences in growth between cells treated with the solvent control (black squares) or inhibitor (white squares).

This example demonstrates ERK-dependence of CXCL12-mediated cellular proliferation. Previous studies have shown that both transformed PC3 and LNCaP, as well as nontransformed N15C6 and BPH-1 prostate epithelial cells, express CXCR4, one of the receptors for CXCL12 (see, e.g., Begley, et al., Cell. 2005 December; 4(6):291-8; Wang J, et al., Cellular Signalling 17 (2005) 1578-1592; Ao M, et al., Cancer Res. 2007 May 1; 67(9):4244-53; each herein incorporated by reference in their entireties). In experiments conducted during the course of development of embodiments for the present invention it was shown that these cells also robustly express CXCR7, a recently-identified second receptor that recognizes CXCL12 (FIG. 19A) (see, e.g., Burns J M, et al., J. Exp. Med. 2006 Sep. 4; 203(9):2201-13; herein incorporated by reference in its entirety). In experiments conducted during the course of development of embodiments for the present invention, it was shown that the stimulation of non-transformed N15C6 and transformed LNCaP cells with CXCL12 at subnanomolar levels similar to those secreted by aging prostate stromal fibroblasts induces these cells to proliferate (see, e.g., Begley, et al., Cell. 2005 December; 4(6): 291-8; herein incorporated by reference in its entirety). As shown in FIG. 19B, N15C6 cells stimulated with 1 pM or 10 pM CXCL12 proliferate to levels significantly higher than those achieved by unstimulated cells ($p<0.001$). This proliferation is maintained even after the cells are pre-treated with an antibody against an unrelated chemokine receptor, CXCR2 (see FIG. 19B). However, pretreatment with antibodies against the CXCL12-specific receptor, CXCR4, or against both CXCR4 and CXCR7, significantly ($p<0.001$) and equivalently ablated the ability of CXCL12 to stimulate proliferation. Thus, CXCL12-stimulated cellular proliferation is mediated through interactions with receptors that specifically recognize this chemokine.

The Ras-mediated mitogen-activated kinase pathway is known to stimulate cellular proliferation. In this pathway, mitogen-activated kinase 1 (MEK1) phosphorylates extracellular regulated kinase (ERK), which in turn phosphorylates and activates other molecules, including transcription factors, involved in cellular proliferation. Treatment of prostate epithelial cells with nanomolar levels of CXCL12 has been shown to activate the MEK/ERK pathway and promote cytokine secretion, angiogenesis, and transendothelial cellular migration (see, e.g., Wang J, et al., Cellular Signalling 17 (2005) 1578-1592; Kukreja P, et al., Cancer Res. 2005 Nov. 1; 65(21):9891-8; each herein incorporated by reference in their entireties). In experiments conducted during the course of development of embodiments for the present invention, it was shown that both sub-nanomolar and nanomolar levels of CXCL12 stimulate MEK/ERK pathway activation in prostate epithelial cells (see FIGS. 19C, 19D, and 19E). However, LNCaP cells treated with CXCL12 at the sub-nanomolar levels that stimulate a proliferative response, e.g., 50 pM, demonstrated only a modest activation of ERK (see FIG. 19C). In contrast, N15C6 cells treated with CXCL12 at the sub-nanomolar levels that stimulate a proliferative response, e.g., 1 pM or 10 pM, demonstrated rapid, transient ERK phosphorylation and activation (see FIGS. 19D and 19E) (see, e.g., Begley, et al., Cell. 2005 December; 4(6):291-8; heriein incorporated by reference in its entirety). The observed differential extent of ERK activation in N15C6 and LNCaP cells treated with levels of CXCL12 known to stimulate proliferation in each cell line suggested that ERK activation might not be equivalently required for CXCL12-mediated proliferation in both cell lines. To test this, the mitogen-activated protein kinase kinase 1 (MEK1) inhibitor, U0126, was utilized to inhibit the ability of MEK1 to phosphorylate ERK, thus preventing ERK activation. As shown in FIG. 19D, treatment of N15C6 cells with 1 pM, 10 pM or 1000 pM CXCL12 results in rapid and transient MEK1-mediated ERK phosphorylation. However, co-treatment of the cells with CXCL12 and 1.0 uM or 5.0 uM U0126 greatly diminishes ERK phosphorylation. Densitometric analysis of the immunoblot confirms these observations and shows that cells pre-treated with either concentration of inhibitor fail to phosphorylate ERK in response to treatment with CXCL12 (see FIG. 19E). Moreover, the proliferative response of N15C6 cells to CXCL12 is nearly ablated when the cells are co-treated with CXCL12 and 5.0 uM U0126 in 0.05% DMSO compared to co-treatment with CXCL12 without inhibitor in 0.05% DMSO (see FIG. 19F). In contrast, the proliferative response of LNCaP cells to CXCL12 was not affected by co-treatment with U0126 (see FIG. 19F).

EXAMPLE XIII

This example describes the materials and methods used for Examples XIX-XXIII.

Construction of Tissue Microarray (TMA) and Immunohistochemistry. A TMA was constructed from 99 prostate tissues including benign prostate, localized prostate cancer and advanced hormone refractory metastatic prostate cancer. Immunostaining was performed on the TMA using standard avidin-biotin complex techniques and a mouse monoclonal antibody against CXCL5. The slide was pretreated by microwaving in Tris buffer, pH 9.0 for antigen retrieval. The TMA was then incubated overnight with primary CXCL5 antibody (Human CXCL5/ENA-78 MAb clone 33160, R&D Systems, Minneapolis, Minn.) 1:25 dilution. CXCL5 expression was scored in a blinded fashion negative (score=1), weak (2), moderate (3), or strong (4) on the basis of the intensity of staining and the percentage of cells exhibiting that staining intensity. Product scores (intensity×percentage values) were calculated for all tissue cores and these values were utilized in subsequent statistical analyses.

Cell Cultures. N15C6 and BPH-1 cells are non-transformed prostate epithelial cells and grow continuously in culture but do not form colonies in soft agar or tumors in immuno-compromised mice (see, e.g., Begley L, et al., Genes Chromosomes Cancer. 2006 February; 45(2):136-46; Macoska J A, et al., Cancer Genet Cytogenet. 2004 Oct. 1; 154(1):36-43; Hayward S W, et al., In Vitro Cell Dev Biol Anim. 1995 January; 31(1): 14-24; each herein incorporated by reference in their entireties). Both cell lines were maintained in 5% HIE media [Ham's F12 (Mediatech Inc. Herndon, Va.) with 5% FBS (Life Technologies, Inc.), 5 ug/ml insulin, 10 ng/ml EGF, 1 ug/ml hydrocortisone (Sigma Chemical Co., St. Louis, Mo.) or in defined serum-free HIE (SF HIE) media supplemented to 5 mM ethanolamine (Sigma Aldrich), 10 mM HEPES (Sigma Aldrich), 5 ug/ul transferrin (Sigma Aldrich), 10 uM 3,3',5-triiodo-L-thyronine (Sigma Aldrich), 50 uM sodium selenite (Sigma Aldrich), 0.1% BSA (JRH Biosciences Lenexa, Kans.), 0.05 mg/ml gentamycin (Gibco), and 0.5 mg/L fungizone, 50 mg/L gentamycin, and 0.52 mg/L plasmocin (Cambrex Bioscience, Walkersville, Md.). The androgen-sensitive LNCaP and 22Rv1 and androgen-insensitive PC3 transformed prostate epithelial cell lines were maintained in 10% RPMI media or SF RPMI (0.1% BSA) and antibiotics as described above (see, e.g., Horoszewicz J S, et al., Cancer Res. 1983 April; 43(4):1809-18; Sramkoski R M, et al., In Vitro Cell Dev Biol Anim. 1999 July-August; 35(7):403-9; Kaighn M E, et al., Invest Urol. 1979 July; 17(1):16-23; each herein incorporated by reference in their entireties).

Proliferation Assays. Cellular proliferation was assessed after plating cells at 50,000 cell/well in triplicate in six well plates and counting cells after 24 and 96 hours of incubation as described previously (see, e.g., Begley L, et al., Genes Chromosomes Cancer. 2006 February; 45(2): 136-46; herein incorporated by reference in its entirety). To assess the effects of exogenous CXCL5 on cellular proliferation, recombinant human CXCL5 (R&D Systems, 254-X) was added at the desired concentration in 2 ml SF media (or 2 ml SF media alone for control) to each well. The cells were re-fed at 24 hours growth and counted at 24 and 96 hours growth. Cell counts were normalized to 50,000 cells at 24 hours to account for any plating discrepancies. Averages and standard deviations of cell number were calculated for each time point under each media condition. For the antibody blockade experiments, 10,000 cells per well were plated in triplicate in 24 well dishes and preincubated with mouse anti-human CXCR2 (Biosource AHR1532X) or mouse antihuman CXCR4 (BD Pharmingen 555971) at 1 ug/ml for 1 hour prior to CXCL5 addition. Cells were maintained in media containing appropriate antibodies for the entirety of the experiment and were counted at 24 and 96 hours as above.

Invasion Assays. Ability to invade through synthetic basement membrane was measured by plating 15,000 cells/well onto control or Matrigel-coated membranes in duplicate using 24-well BD Matrigel Invasion Chambers (Becton-Dickinson). Cells were plated in complete media and left untreated or pre-treated with 1 ug/ml anti-CXCR2 (Biosource AHR1532X) or anti-CXCR4 (BD Pharmingen 555971) for 2 hours, then exposed to complete media only or 20 nM CXCL5 as a chemo-attractant added to the companion plate. After 24 hours of incubation, the upper surface of the membranes were 'scrubbed' to remove non-invasive cells, and the cells that had invaded through to the lower surface of the Matrigel-coated membranes or to the bottom of the companion plate were fixed, stained, and counted. The number of invaded cells was calculated as the average number of cells present on the lower surface of the Matrigel-coated membrane and the companion plate counted over four low power (10× objective) microscopic fields per membrane over both wells per experimental condition.

Western Blot and Protein Analysis. Cells were lysed, proteins resolved by electrophoresis, and electroblotting was carried out as described previously except that 20 ug protein was electrophoresed per gel lane for N15C6 cells and 100 ug protein for LNCaP cells (see, e.g., Begley L, et al., Aging Cell. 2005 December; 4(6):291-8; Begley L A, et al., J Biol. Chem. 2007 Sep. 14; 282(37):26767-74; each herein incorporated by reference in their entireties). Proteins were detected using antibodies against phospho-ERK½ (Cell Signaling #9101), total ERK½ (Cell Signaling, #9102), phospho-p65, (Rockland #100-401-264), total p65 (Rockland #100-4165), STAT3 (9139), phospho-STAT3 (9138), beta-actin (Santa Cruz #sc-1615), or tubulin (Upstate, #DM1A) in conjunction with an ECL detection system. Secondary antibodies included goat anti-rabbit (Cell Signaling, #7074) and goat anti-mouse (Santa Cruz, #SC-2005), and both were used at a 1:5000 concentration. Immunoblots shown are representative of triplicate experiments. Densitometric quantitation of immunoblot films was accomplished by scanning the original films and converting the .tiff files to grayscale. Images were inverted, and mean band intensities were measured using ImageJ (www, followed by, .nih.gov). The mean intensity of adjacent background was also measured for each band and subtracted from band intensity.

Quantitative Real-Time PCR. All quantitative real-time assays were conducted as previously described with an Applied Biosystems 7900HT instrument and reagents (see, e.g., Begley L A, et al., J Biol. Chem. 2007 Sep. 14; 282(37): 26767-74; herein incorporated by reference in its entirety). Cells were grown to 70% confluence in 60 mM dishes prior to RNA purification using the Trizol reagent (Invitrogen Life Technologies). For all experiments, one microgram of RNA was reverse transcribed by use of Superscript III reverse transcriptase (Invitrogen, Carlsbad, Calif.). The resulting cDNA was diluted 1:100. Real-time PCR was performed by use of Assays on Demand (Applied BioSystems, Foster City, Calif.) according to the manufacturer's instructions. Reactions were performed in triplicate, including no-template controls and an endogenous control probe, RPLP0 (ribosomal protein, large, P0), to assess template concentration. Cycle numbers to threshold were calculated by subtracting averaged control from averaged experimental values, and Fold Gene Expression was calculated by raising these values exponential to the base 2. FAM conjugated, gene specific assays were Hs00152928_m1 for EGR1 and Hs99999902_m1 for the control, RPLP0.

Statistical Analysis. Densitometric data from multiple experiments was averaged and standard deviations calculated for graphical depiction and statistical analysis. Similarities and differences in product score distributions between the different histologic sub-types represented on the tissue microarray data were evaluated using Kiruskal-Wallis tests and Wilcoxon rank-sum tests. All other data was assessed by t-test or analysis of variance with p<0.05 considered statistically significant.

EXAMPLE XIX

Figure 20:
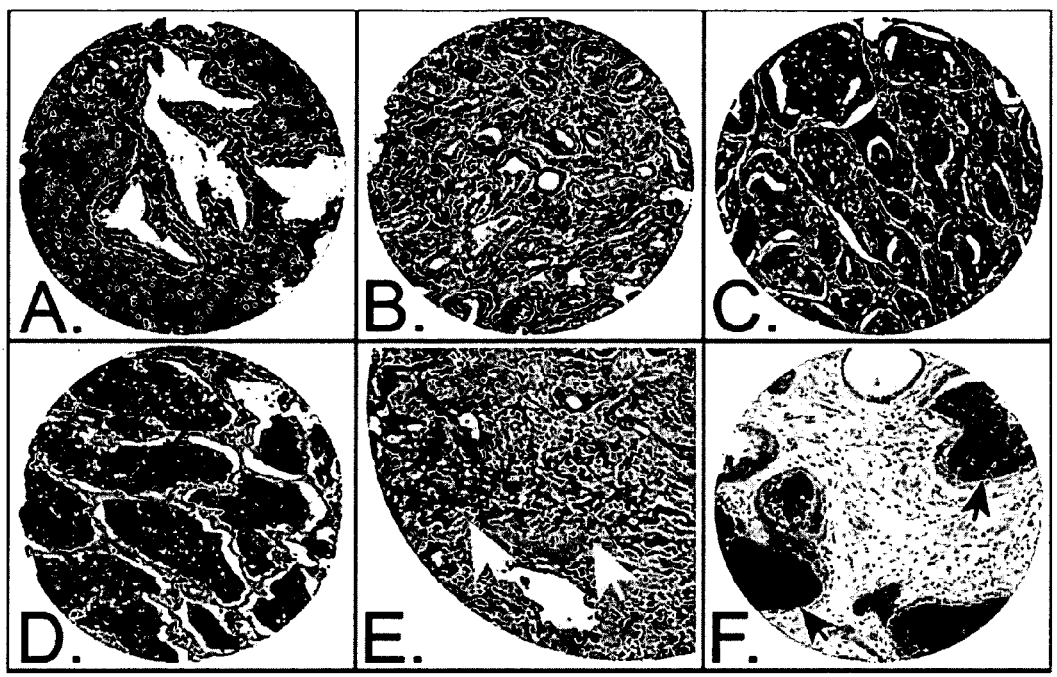
FIG. 20 shows that CXCL5 protein expression is concordant with prostate cancer progression. Shown are representative panels from a hematoxylin and eosin-stained, high-density tissue microarray probed with antibody against CXCL5, as follows.
Figure 20:
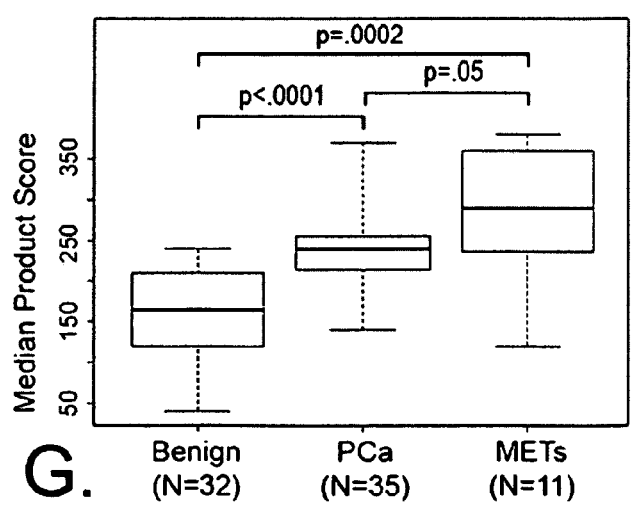

This example shows that CXCL5 protein expression levels are significantly elevated in primary and metastatic prostate tumors. CXCL5 protein expression in human prostate tissues was evaluated by immunohistochemical analysis of a tissue microarray comprising 360 cores obtained from 99 tissue samples, of which 226 cores representing 83 separate tissue samples were evaluable. These included benign glands (N=32 tissues, 76 cores), primary prostate tumors (PCa, N=35 tissues, 84 cores), metastatic prostate tumors (METs, N=11 tissues, 29 cores) and miscellaneous other histologic sub-types (benign prostatic hypertrophy, N=7 tissues, 15 cores; prostatic intraepithelial neoplasia, N=5 tissues, 8 cores; prostatic atrophy, N=9 tissues, 12 cores; prostatic inflammatory atrophy, N=2 tissues, 3 cores). The CXCL5 protein exhibited diffuse cytoplasmic cellular localization by immunostaining which was largely confined to epithelial cell types in both benign and malignant glands. As shown in FIG. 20, CXCL5 immunostaining was significantly higher in primary prostate tumors compared to benign glands (p<0.0001), and significantly higher in metastatic prostate tumors compared to primary prostate tumors PCa (p=0.05) or benign glands (p=0.0002). CXCL5 immunostaining was also significantly higher in prostatic intraepithelial neoplasia (PIN) than benign glands (p=0.0008), though only 5 evaluable PIN lesions were present on the TMA. Taken together, these data show that, for example, CXCL5 protein expression levels increased concordantly with prostate tumor progression. Further evaluation of CXCL5 protein expression levels among primary prostate tumors revealed a trend towards higher expression levels in tumors exhibiting combined Gleason scores of 7 or greater (N=25) compared to those with combined Gleason scores of 6 or less (N=8) (p=0.055) (FIG. 20, B and C), some of these cancer areas were associated with stromal inflammation (FIG. 20 E).

CXCL5 immunostaining was associated with stromal inflammation in 50% (6/12) of cores containing atrophic glands and 100% (3/3) of cores containing PIA lesions. CXCL5 protein immunostaining was also detected in the luminal space of glands histologically characterized as benign (6/75 cores, 8.0%), hyperplastic (4/15 cores, 27%), PIN (2/8 cores, 25%) or malignant glands (6/84 cores, 7%), consistent with active secretion of CXCL5 into the lumen (FIG. 20F). It should be noted that cores from two different cases containing hyperplastic glands demonstrated both luminal and inflammation-associated CXCL5 staining affecting the same glands.

EXAMPLE XX

This example shows that CXCL5 induces a proliferative response in prostate cancer cells in vitro. Because the TMA studies demonstrated that CXCL5 protein expression levels increased concordantly with prostate tumor progression, it was investigated whether CXCL5 promoted a phenotypic response consistent with prostate tumor development and/or progression in vitro. It was first examined whether CXCL5 stimulated the proliferation of prostate cancer cells in vitro. For these experiments, nontransformed (N15C6, BPH-1), androgen-responsive transformed (22Rv1, LNCaP) or androgeninsensitive transformed (PC3) prostate epithelial cells were seeded at 50,000 cells/dish in triplicate, then grown for 3 days in serum-free (SF) media or the same media supplemented with increasing doses of CXCL5. These studies showed that, for example, CXCL5 initiates a moderate but reproducible proliferative response in prostate cancer cells in vitro, and that this response is, for example, evident at sub-nanomolar concentrations of CXCL5 (FIG. 21).

The observed CXCL5-mediated proliferative response was maintained even after the cells were pre-treated with an antibody against an unrelated chemokine receptor, CXCR4 (FIG. 22A). However, pre-treatment with an antibody against the CXCL5-specific receptor, CXCR2, significantly ($p<0.001$) ablated the ability of CXCL5 to stimulate proliferation. These studies showed that, for example, the observed CXCL5-mediated proliferative response was dependent upon interactions with the G-protein coupled receptor, CXCR2, which specifically recognizes this chemokine.

EXAMPLE XXI

This example shows that CXCL5 stimulates prostate cancer cell migration and invasion in vitro. Several studies have shown that the CXC-type chemokine, CXCL12, stimulates the migration and invasion of prostate cancer cells in vitro and in vivo (see, e.g., Singh S, et al., Lab Invest. 2004 December; 84(12):1666-76; Mochizuki H, et al., Biochem Biophys Res Commun. 2004 Jul. 30; 320(3):656-63; Taichman R S, et al., Cancer Res. 2002 Mar. 15; 62(6); Darash-Yahana M, et al., FASEB J. 2004 August; 18(11); each herein incorporated by reference in their entireties). Therefore it was examined whether CXCL5 could also stimulate acquisition of an invasive phenotype by prostate cancer cells. Using a modified Boyden chamber assay, 15,000 PC3 cells were plated onto Matrigel-coated membranes (upper wells) and exposed to complete media, complete media supplemented with 20 nM CXCL5 with or without a 2 hour pre-treatment with 1 ug/ml blocking antibody (anti-CXCR2) or non-specific antibody (anti-CXCR4) in the bottom wells for 12 hours. After 24 hours, the cells that migrated and invaded through the Matrigel were stained and counted. These experiments showed that, for example, significantly more PC3 cells migrated through Matrigel in response to CXCL5 than vehicle (*$p<0.05$), and that this activity was blocked by an antibody against the receptor to CXCL5, CXCR2, but not against the receptor to CXCL12, CXCR4 (FIG. 22B). Thus, transformed PC3 prostate epithelial cells demonstrate a robust and specific migratory/invasive response to CXCL5 in vitro.

EXAMPLE XXII

This example shows that CXCL5 activates both MAPK and PI3K Signaling in Prostate Epithelial Cells. Another CXC-type chemokine, CXCL12, interacts with its primary receptor, CXCR4, to activate downstream signaling events involving the Mitogen-Activated Protein Kinase (MAPK) and/or Phosphoinositide 3-kinase (PI3K), and/or Janus kinases/Signal Transducers and Activators of Transcription (JAK/STAT) pathways in prostate epithelial cells (see, e.g., Begley L, et al., Aging Cell. 2005 December; 4(6):291-8; Begley L A, et al., J Biol. Chem. 2007 Sep. 14; 282(37): 26767-74; each herein incorporated by reference in their entireties). To begin to test whether CXCL5 activated similar pathways associated with prostate epithelial cellular proliferation or invasion, N15C6 or LNCaP cells were treated with increasing doses of CXCL5 and assessed for activation of ERK ½ (MAPK pathway), the p65 subunit of NFkappaB (PI3K pathway) or STAT3 (JAK/STAT pathway). As seen in FIG. 23, nontransformed N15C6 cells rapidly and transiently phosphorylated ERK ½ and STAT3 when treated with either sub-nanomolar (10 pM or 100 pM) or nanomolar (1 nM) levels of CXCL5, whereas NFkappaB subunit activation was evident only after treatment with 1 nM CXCL5. Transformed LNCaP cells rapidly and transiently phosphorylated both ERK ½ and the p65 subunit of NFkappaB upon treatment with sub-nanomolar (10 pM or 100 pM) levels of CXCL5 (FIG. 24). However, activation of either ERK ½ or NFkappaB was not evident in LNCaP cells treated with nanomolar levels of CXCL5, and activation of STAT3 was not observed in LNCaP cells treated with either sub-nanomolar or nanomolar levels of CXCL5.

EXAMPLE XXIII

This example shows that CXCL5 stimulates EGR1 gene transcription. Another CXC type chemokine, CXCL12, stimulates a complex and robust transcriptional response in both nontransformed N15C6 and transformed LNCaP prostate epithelial cells (see, e.g., Begley L A, et al., J Biol. Chem. 2007 Sep. 14; 282(37); herein incorporated by reference in its entirety). In particular, CXCL12 activated transcription of the Early Growth Response 1 (EGR1) gene, which encodes a $C_2H_2$-type zinc-finger protein induced by mitogenic stimulation and shown to stimulate tumor cell growth, play a role in tumor progression, and stimulate angiogenesis and improved survival of tumor cells (see, e.g., Begley L A, et al., J Biol. Chem. 2007 Sep. 14; 282(37); Adamson E D, et al., Tumour Biol. 23:93-102, 2002; each herein incorporated by reference in their entireties). Therefore, it was investigated whether CXCL5 stimulated a transcriptional response in non-transformed or transformed prostate epithelial cells. As shown in FIG. 25, nontransformed N15C6 cells treated with sub-nanomolar levels (1-100 pM) CXCL5 rapidly accumulated 4- to 8-fold more EGR1 transcript than vehicle-treated cells. Similarly treated transformed LNCaP cells accumulated 2- to 3-fold more EGR1 transcript than vehicle-treated cells, but only at the lowest CXCL5 concentration (10 pM) tested.

EXAMPLE XXIV

This example describes the materials and methods used for Examples XXV-XVIII.

Patient Population and Demographics. The patient population was drawn from men referred to a major North American University with an indication for prostate biopsy (e.g. rising or elevated total PSA, abnormal DRE, HGPIN or ASAP on prior biopsy, positive family history of prostate cancer, and known prostate cancer on watchful waiting). Patients presenting for a prostate biopsy were approached to participate in an on-going prospective Prostate Biopsy Clinical database/Tissue Bank study that enables several studies with Institutional Review Board approval, including the prostate biopsy referral database, the Early Detection Research Network (EDRN), and the proposed study. Over a 12 month period, 133 patients consented to the collection and use of clinical data and tissue (serum, urine, prostate tissue). The final study population of 51 patients was selected for those exhibiting pre-biopsy total serum PSA values of <10 ng/ml (determined using the Abbott AxSYM polyclonalmonoclonal immunoassay (Abbott Diagnostics, Abbott Park, Ill), to roughly mirror the observed frequencies of biopsy-verified prostate cancer (36%) and prostatitis (26%) in the larger study population, and to permit examination of equivalent cases of high volume disease within both the biopsy-negative and -positive cases.

Collection of Clinical Data. Clinical and demographic data was collected from the electronic medical record or hard copy medical records for all subjects. This data included information relevant to patient age, date of biopsy, physician, serum PSA levels, medical history, comorbid conditions, medications, physical examination including DRE findings, prior history of prostate biopsies, cost related to the procedure, complications, quality of life (AUA Symptom Score/satisfaction), details of the trans-urethral ultrasounds (TRUS), and findings from the prostate biopsies. Also, as patients were seen in follow-up, any changes in disease status or additional diagnostic testing were added to the database.

Prostate volume data was gathered during a standard TRUS examination performed using a 7.5 MHz biplanar endorectal probe. In addition to assessing the echogenic pattern of the prostate gland, three measurements were made to calculate total prostatic volume. The anterior-posterior (AP) and transverse (TR) diameters were measured at their respective maximal dimensions, whereas the superior-inferior (SI) diameter was measured as the maximal length from the base to the apex of the prostate in the midline sagittal plane. Total prostate volume was estimated by static images using the formula for a prolate ellipsoid, volume=$\pi/6(TR \times AP \times SI)$.

Lower urinary symptom (LUTS) severity, perceived bother and impact from those symptoms are gathered using the American Urological Association Symptom Index (AUASI) indices. These are generated from data acquired from a patient-administered questionnaire, the 8 item validated American Urological Association Symptom Score, which assesses the severity of lower urinary symptoms in men that are most often is attributed to prostate disease. This survey is self completed by the patient prior to the prostate biopsy. AUASI scores of 1-7 indicate none/mild LUTS, 8-19 indicate moderate LUTS, and 20-35 indicate severe LUTS (see, e.g., Barry M J, et al., J. Urol. 1992; 148:1549-57; Discussion 1564; incorporated herein by reference in its entirety).

Collection of Clinical Specimens. Serum samples were collected just prior to prostate needle biopsy in order to obviate any potential surgical- or trauma-induced impact on circulating chemokine or other protein levels in this patient group. Other samples comprised unused serum collected for determination of follow-up PSA values (determined as described above). These 7 samples comprised available serum from patients who were minimally six months postlaparoscopic prostatectomy. As standard procedure, all patients were advised to refrain from taking oral non-steroidal anti-inflammatory drugs (NSAIDs) and other over-the-counter medications for one week prior to biopsy. This served to minimize or obviate potential medication-mediated fluctations in serum chemokine levels. For all patients, blood was drawn into two 30 cc heparinized tubes, transferred 15 ml tubes, centrifuged at 2500 rpm for 10 minutes, and stored in 200 ul aliquots at −80 degrees C. The blood from the EDTA tube was diluted with an equal volume of PBS and subjected to Ficoll Hypaque density gradient centrifugation to separate the lymphocyte granulocyte layer ('buffy coat') and plasma. The plasma layer was carefully removed to a 15 ml tube and centrifuged at 4000 rpm for 10 minutes at 4° C. to remove platelets and all cellular contaminants. The platelet-free plasma was stored at −80 degrees C. in 200 ul aliquots in 0.5 ml cryovials (Sarstedt).

Prostate biopsies were typically performed transrectally using a 12-core extended biopsy template with traditional paramedian sextant biopsies plus additional needle cores directed more laterally (see, e.g., Siu, W., et al., Journal of Urology 174(2):505-9, 2005; herein incorporated by reference in its entirety). Twelve prostate needle biopsy specimens were collected and evaluated per patient, including cores taken from the left/right apex (2 cores), left/right anterior zone (2 cores), left/right medial prostate along length of peripheral zone (6 cores), and left/right base (2 cores). All needle biopsies containing malignant glands were quantitated as to percent of malignant tissue, and further evaluation of perineural invasion or extraprostatic extension is provided. All needle biopsies are evaluated for the presence of HGPIN (high grade prostatic intraepithelial neoplasia)/ASAP (atypical small acinar proliferation), inflammation (acute and chronic), enlargement, or other histopathologies. Each set of needle biopsies was given an overall Gleason grade based on evaluation of entire tumor evaluated.

Definitions of Prostatic Disease Status and Study Groups. Disease status was carefully defined in the study group, as follows:

1. No Disease. Criteria: No finding of cancer based on prostate biopsy. Negative diagnosis for histological prostatitis based on negative findings for acute and/or chronic inflammatory infiltrate on prostate biopsy or history of clinically-diagnosed prostatitis. Prostate volume <37.5 g on TRUS. Prostate biopsy specimens evaluated as normal benign. PSA values <10 ng/ml. This comprised 13/51 (25%) of the total patient population examined in this study.

2. Histological Prostatitis. Criteria: Histologic diagnosis of acute and/or chronic inflammatory infiltrate for one or more prostate biopsy specimens. This comprised 16/51 (31%) of the total patient population examined in this study. Fifteen of these patients were biopsy-negative for cancer, and one was biopsy-positive. None of the 51 patients in the patient population examined in these studies described a clinical diagnosis for prostatitis.

3. BPH. Criteria: Evidence for enlarged prostate. The median prostate volume for the 51 patients included in this study was 37.5 g. Therefore this value was used to define prostates as low volume (<37.5 g) or high volume (37.5 g), roughly equivalent to measures described as high-volume and consistent with BPH in the literature (see, e.g., Al-Azab R, et al., Urology 2007; 69: 103-7; herein incorporated by reference in its entirety). Men with BPH comprised 25/51 (49%) of the total patient population examined in this study, 17/37 (46%) of biopsy-negative patients, and 8/14 (57%) of biopsy-positive patients.

4. Cancer. Criteria: Histological diagnosis of malignant glands from prostate biopsy. This comprised 14/51 (27%) of the total patient population examined in this study, which approximated the proportion of patients (⅓, 33%) with biopsy-verified cancer within the larger patient population comprising the EDRN study. Five board-certified pathologists were involved in the histologic diagnoses of the prostate biopsies. The number of positive biopsies among these 14 patients varied from 1 to 7, with a mean (and median) of 2 positive biopsies per patient, with a mean (and median) Gleason score of 6. The subsequent treatment courses for these patients varied widely, with 5 patients undergoing laparoscopic or radical retropubic prostatectomy, 3 patients undergoing external beam radiation or brachytheraphy, 4 patients under watchful waiting, and 2 patients who did not return for treatment.

ELISA Assays. Circulating serum CXCL5 (ENA-78) or CXCL12 (SDF-1) chemokine levels were assessed using 50 ul frozen serum or plasma per direct sandwich ELISA in duplicate using the Human CXCL5/ENA-78 DuoSet kit DY254 or the Human CXCL12/SDF-1 alpha capture antibody MAB350, detection antibody BAF310, and standard 350-NS ELISA reagents (R&D Systems). Measures within each patient group were regarded as biological replicates and permitted statistical comparisons between groups. For all ELISAs, a standard curve was generated with the provided standards and utilized to calculate the quantity of chemokine in the sample tested. These assays provide measures of chemokines concentration with excellent reproducibility, with replicate measures characterized by standard deviations from the mean on the order of 1-2%. Measures for each chemokine were performed for all samples simultaneously to avoid potential 'batch effect' variations in measurement.

Statistical Analysis. The bivariate relationship of circulating chemokine levels, age, and disease severity (gland volume, baseline PSA, and AUASI) with disease status was tested in this patient population using the Wilcoxon rank-sum test. Separate tests were performed for each definition of disease status (e.g., cancer vs no cancer, low volume vs high volume, etc) in pairwise fashion. All tests were performed using SAS v9.1.3 at the 5% significance level.

EXAMPLE XXV

This example shows the Clinico-pathologic characteristics of the patient population. The study population of 51 patients was selected for those cases exhibiting pre-biopsy total serum PSA values of <10 ng/ml, that roughly mirrored the observed frequencies of biopsy-verified prostate cancer (36%) and prostatitis (26%) in the larger study population, and would permit examination of equivalent cases of high volume disease (BPH) within both the biopsy-negative and -positive cases. Although all of the patients included in this study exhibited pre-biopsy total serum PSA values of <10 ng/ml, these values were significantly higher for men with BPH compared to those with smaller prostates (p=0.001). Prostate volume itself varied concordantly with biopsy-diagnosed prostatitis (acute, chronic, or both) such that prostates without evidence of prostatitis were significantly smaller, with a median volume of 34.4 g, than prostates with evidence of prostatitis, with a median volume of 53.1 g (p=0.008). Men with biopsy-diagnosed prostatitis were significantly younger than those without evidence of prostatitis, with a median age of 54.0 compared to 61.0 years, respectively (p=0.003). This relationship held both in the presence (p=0.021) or absence (p=0.039) of concurrent prostatic enlargement. Men that were biopsypositive for cancer were older (median age 61.5 years) than men that were biopsy-negative cancer for cancer (median age 57.0 years) but this difference was not significant (p=0.061). Results from completion of the American Urological Association Symptom Index (AUASI) questionnaire for men without cancer demonstrated similar scores consistent with moderate symptoms for patients with smaller volume prostates (median score 8.5) or with prostatic enlargement (median score 9.0) (p=0.557). However, men with cancer reported significantly higher scores consistent with moderate symptoms (median score 11.5) concordant with prostatic enlargement compared to men with smaller prostates who reported scores consistent with none or mild symptoms (median score 4.0) (p=0.003). The presence or absence of biopsydiagnosed prostatitis was not associated with significant differences in AUASI scores among the patient population as a whole or among men with or without cancer and/or prostatic enlargement in particular. These data are shown collectively in Table IV.

TABLE IV

| PATIENT CATEGORY | N | VOLUME (g) | | | AGE (years) | | |
|---|---|---|---|---|---|---|---|
| | | Median | Mean (SD) | p-value | Median | Mean (SD) | p-value |
| ALL PATIENTS: BY SUBCATEGORY: | 51 | 37.5 | 45.4 (20.9) | | 59.0 | 59.5 (8.1) | |
| low volume (±37.8 g) | 26 | 30.0 | 29.6 (5.6) | 0.026 | 59.8 | 60.0 (12.1) | 0.792 |
| high volume (>57.8 g) | 25 | 35.1 | 61.5 (18.1) | | 59.0 | 59.0 (8.1) | |
| without prostatitis | 35 | 34.4 | 39.4 (16.5) | 0.025 | 61.0 | 61.9 (8.9) | 0.003 |
| with prostatitis | 46 | 53.1 | 58.5 (24.0) | | 54.0 | 54.1 (7.2) | |
| low volume without prostatitis | 22 | 30.0 | 29.5 (5.5) | 0.915 | 61.0 | 61.5 (9.9) | 0.039 |
| low volume with prostatitis | 4 | 29.9 | 29.1 (6.5) | | 61.0 | 51.0 (6.2) | |
| high volume without prostatitis | 13 | 53.7 | 55.8 (15.5) | 0.125 | 52.0 | 52.3 (7.3) | 0.021 |
| high volume with prostatitis | 12 | 78.7 | 68.3 (18.5) | | 55.3 | 55.2 (7.5) | |
| PATIENTS WITHOUT CANCER: BY SUBCATEGORY: | 37 | 37.0 | 45.4 (21.7) | | 57.0 | 58.0 (9.5) | |
| low volume | 20 | 31.3 | 29.9 (6.0) | 0.026 | 57.0 | 58.6 (12.2) | |
| high volume | 17 | 60.0 | 65.8 (16.5) | | 57.0 | 57.2 (8.3) | 0.215 |

TABLE IV-continued

| PATIENTS WITH CANCER: BY SUBCATEGORY: | 14 | 48.0 | 42.7 (19.4) | | 61.5 | 63.2 (5.7) | |
|---|---|---|---|---|---|---|---|
| low volume | 6 | 27.3 | 28.5 (4.5) | 0.022 | 62.0 | 64.8 (5.5) | 0.603 |
| high volume | 8 | 48.3 | 53.2 (19.6) | | 61.5 | 62.3 (7.2) | |

| PATIENT CATEGORY | PSA (ng/ml) | | | | AUASI | | |
|---|---|---|---|---|---|---|---|
| | N | Median | Mean (SD) | p-value | Median | Mean (SD) | p-value |
| ALL PATIENTS: BY SUBCATEGORY: | 51 | 4.2 | 4.5 (2.5) | | 9.0 | 9.4 (5.6) | |
| low volume (±37.8 g) | 26 | 3.2 | 3.5 (2.5) | 0.030 | 6.5 | 8.2 (6.4) | 0.033 |
| high volume (>57.8 g) | 25 | 5.4 | 5.4 (5.5) | | 11.0 | 10.6 (4.8) | |
| without prostatitis | 35 | 4.2 | 4.5 (2.5) | 0.652 | 9.2 | 9.8 (5.7) | 0.483 |
| with prostatitis | 46 | 4.1 | 4.5 (2.3) | | 6.0 | 3.4 (5.4) | |
| low volume without prostatitis | 22 | 3.3 | 3.3 (2.3) | 0.439 | 7.5 | 9.3 (5.4) | 0.024 |
| low volume with prostatitis | 4 | 2.4 | 3.2 (1.9) | | 2.0 | 3.0 (2.8) | |
| high volume without prostatitis | 13 | 5.7 | 5.5 (0.9) | 0.241 | 11.0 | 10.8 (4.5) | 0.816 |
| high volume with prostatitis | 12 | 4.5 | 5.3 (2.3) | | 9.0 | 10.4 (4.5) | |
| PATIENTS WITHOUT CANCER: BY SUBCATEGORY: | 37 | 3.9 | 4.4 (2.2) | | 9.0 | 9.8 (5.9) | |
| low volume | 20 | 3.0 | 3.4 (3.9) | 0.031 | 8.5 | 9.6 (6.8) | 0.557 |
| high volume | 17 | 5.1 | 5.5 (1.9) | | 9.0 | 10.3 (5.8) | |
| PATIENTS WITH CANCER: BY SUBCATEGORY: | 14 | 5.0 | 4.9 (2.2) | | 6.5 | 8.5 (4.9) | |
| low volume | 6 | 3.8 | 4.3 (3.4) | 0.174 | 4.0 | 4.2 (1.2) | 0.003 |
| high volume | 8 | 5.7 | 5.3 (0.8) | | 11.5 | 11.8 (3.8) | |

EXAMPLE XXVI

This example shows that CXCL5 and CXCL12 are differentially secreted by older compared to younger human primary prostate stromal fibroblasts. As previously reported, the gene expression profiles of primary fibroblast cell populations cultured from the peri-urethral region of prostates of younger (aged 40-52 y/o) or older (aged 63-72) patients diagnosed with prostate cancer patients identified several differentially expressed transcripts encoding secreted proteins (see, e.g., Begley L, et al., Aging Cell. 2005; 4:291-8; incorporated herein by reference in its entirety). Among these, two genes encoding CXC-type chemokines, CXCL5 and CXCL12, were significantly up-regulated at the transcriptional level by older compared to younger primary prostate stromal fibroblasts. Moreover, ELISA assays demonstrated that CXCL5 was secreted at levels 5-fold higher, and CXCL12 at levels 3.5-fold higher, by older compared to younger prostate stromal fibroblasts (FIG. 26). Taken together, these data validated the observation that older human prostate stromal fibroblasts differed from their younger counterparts by actively expressing the genes and corresponding proteins for CXCL5 and CXCL12 that function as inflammatory mediators with growth factor activities.

EXAMPLE XXVII

This example shows that serum CXCL5 and CXCL12 levels are concordant with the presence of prostatic disease. Because CXCL5 and CXCL12 are secreted molecules and were found to be associated with aging and prostate cellular proliferation, it was hypothesized that their levels in patient serum might, singly or in combination, serve as biomarkers to distinguish between BPH and PCa. To test this, ELISAs for CXCL5 and CXCL12 were performed on whole serum from 51 men enrolled in the Early Detection Research Network study as described above. The ELISA analyses showed that total serum CXCL12 levels were significantly higher for patients exhibiting biopsy-verified cancer compared to men with who were biopsy-negative for cancer and histological prostatitis (p=0.050) (Table V and FIG. 27A, B, C).

TABLE V

| Comparison | N | CXCL5 | | | | CXCL12 | | | |
|---|---|---|---|---|---|---|---|---|---|
| | | Mean | SD | Median | p value | Mean | SD | Median | p value |
| With Cancer: Low and High Volume Compared to: | 14 | 0.88 | 0.30 | 0.91 | | 1.17 | 1.03 | 0.82 | |
| Without Cancer: All | 37 | 1.01 | 0.72 | 0.80 | 0.776 | 0.74 | 0.54 | 0.54 | 0.151 |
| Without Cancer: All Prostatitis | 15 | 0.66 | 0.25 | 0.77 | 0.058 | 1.05 | 0.81 | 1.27 | 0.963 |
| Without Cancer: Acute Prostatitis Only | 11 | 0.69 | 0.24 | 0.77 | 0.095 | 1.10 | 0.62 | 1.27 | 0.978 |
| Without Cancer: No Prostatitis | 26 | 1.14 | 0.81 | 1.01 | 0.640 | 0.58 | 0.43 | 0.49 | 0.050 |
| Without Cancer: Low Volume Only, No Prostatitis | 13 | 1.39 | 0.86 | 1.24 | 0.117 | 0.55 | 0.38 | 0.39 | 0.047 |
| With Cancer: High Volume Compared to: | 8 | 1.05 | 0.18 | 1.03 | | 1.08 | 1.10 | 0.58 | |
| Without Cancer: High Volume, All Prostatitis | 8 | 0.65 | 0.19 | 0.72 | 0.003 | 1.19 | 0.68 | 1.32 | 0.713 |
| Without Cancer, High Volume, No Prostatitis | 9 | 0.67 | 0.44 | 0.40 | 0.061 | 0.65 | 0.53 | 0.54 | 0.736 |
| With Cancer, Low Volume | 6 | 0.66 | 0.29 | 0.67 | | 1.33 | 1.00 | 1.19 | |

TABLE V-continued

| | | CXCL5 | | | | CXCL12 | | | |
|---|---|---|---|---|---|---|---|---|---|
| Comparison | N | Mean | SD | Median | p value | Mean | SD | Median | p value |
| Compared to: | | | | | | | | | |
| Without Cancer: Low Volume, All Prostatitis | 3 | 0.81 | 0.36 | 1.00 | 0.699 | 0.87 | 0.46 | 0.91 | 0.519 |
| Without Cancer: Low Volume, No Prostatitis | 17 | 1.39 | 0.86 | 1.24 | 0.06 | 0.55 | 0.38 | 0.39 | 0.050 |

When evaluated according to prostate volume, serum CXCL12 levels were found to be lowest among men without BPH, cancer, or histological evidence of prostatitis. Moreover, serum CXCL12 levels were significantly different between men with no evidence of prostatic disease and men with biopsy-verified cancer (p=0.047) (Table V and FIG. 27A, B, C). Thus, serum CXCL12 clearly distinguished men without prostatic disease from those with cancer, and this predictive value was most significant among men without BPH.

When analyzed without regard to prostate volume, total serum CXCL5 levels were unable to definitively distinguish between men with or without biopsy-diagnosed cancer (Table V and FIG. 27A, B, C). However, total serum CXCL5 levels were clearly inversely associated with prostate volume, with median values almost three-fold higher in men with low volume prostates compared to men with BPH but no other evidence of prostatic disease (Table V and FIG. 27A, B, C). Among men with BPH who were biopsy-negative for cancer, total serum CXCL5 levels were significantly higher in men with concomitant histological prostatitis compared to those without other evidence of disease (p<0.003) (Table V and FIG. 27A, B, C). Thus, serum CXCL5 levels were progressively elevated in, and predictive for, prostatitis and prostate cancer concurrent with BPH.

Seven additional patients who were diagnosed with prostate cancer upon needle biopsy and subsequently underwent laparoscopic removal of the prostate were assessed for CXCL5 and CXCL12 levels in serums drawn at the time of prostate biopsy and at least six month postprostatectomy. All of these patients were characterized by stage T1c or T2a localized Gleason Score 6 or 7 tumors. In 5/7 (71%) patients (cases 3-7), post-prostatectomy serum CXCL12 values were reduced to half or less of those obtained at the time of prostate biopsy. Moreover, post-prostatectomy serum CXCL12 was undetectable in cases 4 and 6. Cases 1 and 2 demonstrated post-prostatectomy serum CXCL12 values that were identical to or higher than those obtained from serum drawn at the time of needle biopsy (FIG. 27D). It should be noted that the post-prostatectomy serums used for cases 1 and 2 was drawn at 7 and 8 months, respectively, post-prostatectomy, whereas those for cases 3-7 were drawn 9 months or more post-prostatectomy. Total serum CXCL5 levels were not significantly different in biopsycollected and post-prostatectomy samples. These data suggest that the elevated serum CXCL12 levels observed in men with biopsy-positive prostate cancer were directly related to carcinoma of the prostate.

EXAMPLE XXVIII

This example provides a comparison of chemokine measurements in serum or plasma. Because CXCR4 (the receptor for CXCL12) is expressed on platelets, and CXCL5 can be released from activated platelets, the CXCL12 and CXCL5 levels were measured by ELISA (as described above) and compared in both serum and platelet-free plasma from 6 of the 51 patients examined in this study. These assays showed that ELISA-derived values for CXCL12 were almost an order of magnitude lower, but parallel, in serum compared to plasma samples from the same patients (FIG. 28). With the exception of values for one patient (patient "B" in FIG. 27D), ELISA derived values for CXCL5 were in good agreement between serum and plasma samples from the same patients. For both CXCL5 and CXCL12, however, the majority of ELISA-derived values were higher in plasma compared to serum samples, suggesting that plasma may provide a more sensitive means for the quantitation of these chemokines than serum.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A method for characterizing prostate tissue in a subject, comprising:
    a) providing a sample from a subject suspected of having a prostatic disease, wherein said subject has a PSA level at or less than 10 ng/ml, wherein said sample is selected from the group consisting of prostate tissue, serum, plasma, mucus, blood, and urine;
    b) detecting and comparing the amount of expression of CXCL5 and CXCL12 in said prostate tissue sample; and
    c) characterizing said prostate tissue sample as indicative of prostate cancer or benign prostatic hyperplasia based upon said comparing, wherein a higher amount of detected CXCL12 expression than CXCL5 expression is indicative of prostate cancer, wherein a higher amount of detected CXCL12 expression than CXCL5 expression is indicative of prostate cancer.

2. The method of claim 1, wherein said detecting the amount of expression of CXCL5 and CXCL12 comprises detecting the amount of CXCL5 and CXCL12 polypeptide.

3. The method of claim 2, wherein said detecting the amount of expression of a CXCL5 and CXCL12 polypeptide comprises exposing said CXCL5 and CXCL12 polypeptide to an antibody specific to said CXCL5 and CXCL12 polypeptide and detecting the amount of binding of said antibody to said CXCL5 and CXCL12 polypeptide.

4. The method of claim 1, wherein said subject comprises a human subject.

5. The method of claim 1, wherein said sample comprises tumor tissue.

6. The method of claim 1, further comprising the step of c) providing a prognosis to said subject.

* * * * *

UNITED STATES PATENT AND TRADEMARK OFFICE
CERTIFICATE OF CORRECTION

PATENT NO.        : 7,598,028 B2
APPLICATION NO. : 11/946676
DATED             : October 6, 2009
INVENTOR(S)       : Jill A. Macoska It is certified that error appears in the above-identified patent and that said Letters Patent is hereby corrected as shown below:

Please replace TABLE II which starts in Column 69, Line 51, and ends in Column 70, Line 49, with the attached TABLE II.

Signed and Sealed this

First Day of December, 2009

David J. Kappos
*Director of the United States Patent and Trademark Office*

TABLE II

Genes Commonly Transcriptionally Regulated by CXCL12 in N15C6 and LNCaP Cells

| DOWN-REGULATED GENES | PROMOTING EFFECT ON CELLULAR PROLIFERATION/TUMOR METASTASIS |
|---|---|
| CDH1 | impairs cell-cell adhesion |
| CTNNB1 | impairs cell-cell adhesion |
| CPSF1 | impairs cell-cell adhesion |
| EXOSC6 | impairs cell-cell adhesion |
| ITGB4 | impairs cell-cell adhesion |
| LOXL2 | impairs cell-cell adhesion |
| SORBS3 | impairs cell-cell adhesion |
| GSR | Impairs response to oxidative stress |
| RANGAP1 | Impairs formation of mitotic spindle, disrupts normal cell division? |
| NUMA1 | Impairs formation of mitotic spindle, disrupts normal cell division? |
| RBM14 | Impairs DNA repair, facilitates mutation? |
| BMP1 | Impairs basement membrane assembly |
| ERBB2 | Expression is associated with apoptosis in prostate and colon tumors |
| MAPRE3 | Facilitates cell motility |
| DOCK9 | Facilitates (?) cell motility |
| ARPC4 | Facilitates (?) cell motility |
| MARCKS | Facilitates (?) cell motility |
| TP53 | Promotes progression through cell cycle |
| MAFK | Promotes progression through cell cycle |
| CUGBP1 | Promotes progression through cell cycle |
| CDK2 | Promotes progression through cell cycle |
| CDK9 | Promotes progression through cell cycle |
| HIPK3 | Promotes resistance to apoptosis? |
| MAPK8IP2 | Promotes resistance to apoptosis |
| CANX | Promotes resistance to apoptosis |
| NR2F6 | Impairs transcriptional repression |
| UNCLEAR | STAT2, LAMP1, AP3D1, PEX5, SLC16A3, TNPO2, EHMT1, IPO8, MTMR1, PTBPI, THOC4, ARS2, DNAJC14, BNS, LSS, NADK, GLT25D1, UNC13D, REPIN1 |
| UNKNOWN | TM9SF4, CDCP1, FLJ20273, FNDC5, WDR6, WDR76, UBE3B |
| | |
| UP-REGULATED GENES | PROMOTING EFFECT ON CELLULAR REGULATED PROLIFERATION/TUMOR METASTASIS |
| EGFR | Potentially up-regulates cell proliferation |
| CD44 | Promotes resistance to apoptosis metastasis repressor in prostate cancer |
| ANKRD12 | Amplified in some retinoblastomas |
| SSBP1 | Associated with transcriptional up-regulation |
| CCNT1 | Controls HIV transcript elongation (with CDK9) |
| JMJD1C | Family members amplified in some cancers |
| HNRPD | Involved in post-transcriptional regulation of early response genes |

| | |
|---|---|
| GOPC | May up-regulate Rho GTPase activity |
| STRAP | Overexpression activates mitogen-activated protein kinase, promotes anchorage-independent growth of the cells frequently overexpressed in human breast tumors |
| DYX1C1 | Transcriptionally regulated by ELK-1 |
| UNCLEAR | FNBP4, PRPS2, EIF3S8, RPL38, LMO7 |
| UNKNOWN | RPM27, CRBN, NUPL2, ANF638, PIK3C2A, ZNF567, FLJ22028, PITPNB, BAT2D1, CEP350, FAM44A, KIAA0256, KLHL8, LOC554203, NFKBIZ, THAP6, TM2D1 |
| | |